(12) United States Patent
Buck et al.

(10) Patent No.: US 11,207,335 B2
(45) Date of Patent: *Dec. 28, 2021

(54) METHODS OF USING HUMAN MILK OLIGOSACCHARIDES FOR IMPROVING AIRWAY RESPIRATORY HEALTH

(71) Applicant: ABBOTT LABORATORIES, Abbott Park, IL (US)

(72) Inventors: Rachael Buck, Gahanna, OH (US); Geralyn O. Duska-McEwen, Columbus, OH (US); Steven R. Davis, Columbus, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/456,221

(22) Filed: Aug. 11, 2014

(65) Prior Publication Data

US 2015/0031645 A1   Jan. 29, 2015

Related U.S. Application Data

(63) Continuation of application No. 13/335,433, filed on Dec. 22, 2011, now Pat. No. 8,802,650.

(60) Provisional application No. 61/428,860, filed on Dec. 31, 2010, provisional application No. 61/527,851, filed on Aug. 26, 2011.

(51) Int. Cl.
| | | |
|---|---|---|
| *A01N 43/04* | (2006.01) | |
| *A61K 31/70* | (2006.01) | |
| *A61K 31/702* | (2006.01) | |
| *A23L 33/00* | (2016.01) | |
| *A61K 31/716* | (2006.01) | |
| *A23C 9/20* | (2006.01) | |
| *A61K 31/05* | (2006.01) | |

(52) U.S. Cl.
CPC ............ *A61K 31/702* (2013.01); *A23C 9/206* (2013.01); *A23L 33/40* (2016.08); *A61K 31/05* (2013.01); *A61K 31/716* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,762,822 A | 8/1988 | Ettinger | |
| 5,096,982 A | 3/1992 | Hesse et al. | |
| 5,260,280 A | 11/1993 | Isoda et al. | |
| 5,492,899 A | 2/1996 | Masor et al. | |
| 5,700,671 A | 12/1997 | Prieto et al. | |
| 5,834,423 A | 11/1998 | Koketsu et al. | |
| 5,906,982 A | 5/1999 | Prieto et al. | |
| 6,036,992 A | 3/2000 | Borror et al. | |
| 6,045,854 A | 4/2000 | Prieto et al. | |
| 6,080,787 A | 6/2000 | Carlson et al. | |
| 6,083,934 A | 7/2000 | Prieto et al. | |
| 6,146,670 A | 11/2000 | Prieto et al. | |
| 6,306,908 B1 | 10/2001 | Carlson et al. | |
| 6,365,218 B1 | 4/2002 | Borschel et al. | |
| 6,497,908 B1 | 12/2002 | Oshiro | |
| 6,511,696 B2 | 1/2003 | Gohman | |
| 6,576,251 B1 | 6/2003 | Stahl et al. | |
| 6,630,452 B2 | 10/2003 | Wilson | |
| 6,946,451 B2 | 9/2005 | Takada et al. | |
| 7,090,862 B2 | 8/2006 | Barrett-Reis et al. | |
| 7,090,879 B2 * | 8/2006 | Albrecht | A23L 2/39 426/262 |
| 7,122,315 B2 | 10/2006 | Ley Vega De Seoane et al. | |
| 7,416,752 B2 | 8/2008 | Holub et al. | |
| 8,580,316 B2 | 11/2013 | Boehm et al. | |
| 8,703,737 B2 | 4/2014 | Buck et al. | |
| 8,754,064 B2 | 6/2014 | Rabet | |
| 8,802,650 B2 | 8/2014 | Buck et al. | |
| 8,999,924 B2 | 4/2015 | Georgi et al. | |
| 9,078,466 B2 | 7/2015 | Boehm et al. | |
| 9,131,710 B2 | 9/2015 | Boursier et al. | |
| 2002/0019991 A1 | 2/2002 | Prieto et al. | |
| 2003/0060445 A1 | 3/2003 | Wilson | |
| 2004/0001817 A1 | 1/2004 | Giampapa | |
| 2004/0047866 A1 | 3/2004 | Harn et al. | |
| 2004/0191295 A1 | 9/2004 | Locniskar | |
| 2004/0202765 A1 | 10/2004 | McMahon et al. | |
| 2004/0265462 A1 | 12/2004 | Carlson | |
| 2005/0004070 A1 | 1/2005 | Stahl et al. | |
| 2005/0070464 A1 | 3/2005 | Stahl et al. | |
| 2005/0096295 A1 | 5/2005 | McMahon et al. | |

(Continued)

FOREIGN PATENT DOCUMENTS

| | | |
|---|---|---|
| CA | 2285066 | 10/1998 |
| CA | 2577698 | 2/2006 |

(Continued)

OTHER PUBLICATIONS

Bendich Annals New York Academy of Sciences (1993), vol. 691, pp. 61-67.*
Vivier et al. Nature Immunology (2008), vol. 9, pp. 503-510.*
Response in U.S. Appl. No. 13/335,018 dated Mar. 20, 2015.
Final office action with Examiner-Initiated Interview Summary in U.S. Appl. No. 13/335,404 dated May 4, 2015.
Non-final office action in U.S. Appl. No. 14/195,938 dated May 1, 2015.
English translation of Second Office Action in CN 201180068364.8 dated Feb. 9, 2015.
Search Report and Written Opinion in SG 2013050745 dated Jan. 26, 2015.
Search Report and Written Opinion in SG 201305084.4 dated Jan. 26, 2015.
Agostini, C., "Role of Long-Chain Polyunsaturated Fatty Acids in the First Year of Life," J. Pediatr. Gastroenterol. Nutr., vol. 47, No. Suppl. 2, pp. S41-S44.

(Continued)

*Primary Examiner* — Patrick T Lewis
(74) *Attorney, Agent, or Firm* — Calfee, Halter & Griswold LLP

(57) ABSTRACT

Disclosed are nutritional compositions including human milk oligosaccharides that can be administered to preterm infants, term infants, toddlers, and children for improving airway defense mechanisms.

15 Claims, 24 Drawing Sheets

(56) References Cited

U.S. PATENT DOCUMENTS

| | | | |
|---|---|---|---|
| 2005/0208179 A1 | 9/2005 | Albrecht et al. | |
| 2005/0239814 A1 | 10/2005 | Simoneau et al. | |
| 2005/0271641 A1 | 12/2005 | Bjorksten et al. | |
| 2006/0039954 A1 | 2/2006 | Gierhart et al. | |
| 2006/0088574 A1 | 4/2006 | Manning et al. | |
| 2006/0246146 A1 | 11/2006 | McMahon et al. | |
| 2006/0247153 A1 | 11/2006 | McMahon et al. | |
| 2006/0270739 A1 | 11/2006 | Johnson et al. | |
| 2007/0048405 A1 | 3/2007 | DeWille et al. | |
| 2007/0098849 A1 | 5/2007 | Barrett-Reis et al. | |
| 2007/0104700 A1 | 5/2007 | Garcia-Rodenas et al. | |
| 2007/0104843 A1 | 5/2007 | Holst et al. | |
| 2007/0173480 A1 | 7/2007 | Clandinin et al. | |
| 2007/0274983 A1 | 11/2007 | Gerardu et al. | |
| 2008/0003329 A1 | 1/2008 | Rueda et al. | |
| 2008/0003330 A1 | 1/2008 | Rueda et al. | |
| 2008/0057178 A1 | 3/2008 | Rueda et al. | |
| 2008/0064635 A1 | 3/2008 | Rueda et al. | |
| 2008/0089981 A1 | 4/2008 | Butler et al. | |
| 2008/0124323 A1 | 5/2008 | Boehm et al. | |
| 2008/0125346 A1 | 5/2008 | Beermann et al. | |
| 2009/0082249 A1 | 3/2009 | Garssen et al. | |
| 2009/0092590 A1 | 4/2009 | Rangavajla et al. | |
| 2009/0098240 A1 | 4/2009 | Mills et al. | |
| 2009/0118229 A1 | 5/2009 | Zeina | |
| 2009/0143301 A1 | 6/2009 | Olson et al. | |
| 2009/0191151 A1 | 7/2009 | Gai et al. | |
| 2009/0305996 A1 | 12/2009 | Beermann et al. | |
| 2010/0047393 A1 | 2/2010 | Glas et al. | |
| 2010/0063002 A1 | 3/2010 | Stahl et al. | |
| 2010/0233129 A1* | 9/2010 | Fichot | A61K 31/351 424/93.4 |
| 2010/0233198 A1 | 9/2010 | Fichot et al. | |
| 2010/0260720 A1 | 10/2010 | Sprenger | |
| 2010/0298244 A1 | 11/2010 | Yang et al. | |
| 2012/0172330 A1 | 7/2012 | Buck | |
| 2012/0172331 A1 | 7/2012 | Buck | |
| 2012/0177691 A1* | 7/2012 | Stahl | A23L 1/09 424/278.1 |
| 2014/0256674 A1 | 9/2014 | Buck | |

FOREIGN PATENT DOCUMENTS

| | | | |
|---|---|---|---|
| CN | 101233874 | 8/2008 | |
| CN | 101449708 | 6/2009 | |
| EP | 1487469 | 12/2004 | |
| EP | 1634599 | 3/2006 | |
| EP | 2127661 | 2/2009 | |
| EP | 2060257 | 5/2009 | |
| EP | 2060257 A1 * | 5/2009 | ........... A61K 31/351 |
| EP | 0975235 B2 * | 1/2014 | ............. A23L 29/30 |
| GN | 1407857 A | 4/2003 | |
| GN | 101330838 A | 12/2008 | |
| JP | 8266255 | 10/1996 | |
| JP | 10099048 | 4/1998 | |
| JP | 10327804 | 12/1998 | |
| MX | MX/a/2013/005727 | 7/2013 | |
| WO | 1997048388 | 12/1997 | |
| WO | 19980043494 | 10/1998 | |
| WO | 2003003981 | 1/2001 | |
| WO | 2001042263 | 6/2001 | |
| WO | 2001060346 | 8/2001 | |
| WO | 200178748 A2 | 10/2001 | |
| WO | 2004032639 | 4/2004 | |
| WO | 2004/093885 A1 | 11/2004 | |
| WO | 2004112509 | 12/2004 | |
| WO | 2005055944 | 6/2005 | |
| WO | 2006022543 | 3/2006 | |
| WO | 2007046697 | 4/2007 | |
| WO | 2007046699 | 4/2007 | |
| WO | 2007087468 | 8/2007 | |
| WO | 2007101675 | 9/2007 | |
| WO | 2007114683 | 10/2007 | |
| WO | 2007114696 | 10/2007 | |
| WO | 2007136428 | 11/2007 | |
| WO | 2008016306 | 2/2008 | |
| WO | 2008056983 | 5/2008 | |
| WO | 2008108651 | 9/2008 | |
| WO | 2008127104 | 10/2008 | |
| WO | 2008139984 | 11/2008 | |
| WO | 2008153391 | 12/2008 | |
| WO | 2009033011 | 3/2009 | |
| WO | 2009059996 | 5/2009 | |
| WO | 2009060073 | 5/2009 | |
| WO | 2009067000 | 5/2009 | |
| WO | 2009077352 | 6/2009 | |
| WO | 2009102193 | 8/2009 | |
| WO | 2009/112361 A2 | 9/2009 | |
| WO | 20090113861 | 9/2009 | |
| WO | 2010003803 | 1/2010 | |
| WO | 2010023178 | 3/2010 | |
| WO | 20100070104 | 6/2010 | |
| WO | 2010/092153 A1 | 8/2010 | |
| WO | 20100115934 | 10/2010 | |
| WO | 2011005681 | 1/2011 | |
| WO | 2011008087 | 1/2011 | |
| WO | 2011012655 | 2/2011 | |
| WO | 2011090926 | 7/2011 | |
| WO | 2011096809 | 8/2011 | |
| WO | 2011136636 | 11/2011 | |
| WO | 2011136647 | 11/2011 | |
| WO | 2012/009315 A2 | 1/2012 | |
| WO | 2012009315 | 1/2012 | |
| WO | 2012076323 | 6/2012 | |
| WO | 2012092153 | 7/2012 | |
| WO | 2012/156273 A1 | 11/2012 | |

OTHER PUBLICATIONS

Office Action in U.S. Appl. No. 13/335,018 dated Jun. 29, 2015.
Applicant-Initiated Interview Summary for U.S. Appl. No. 13/335,404 dated Aug. 10, 2015.
Amendment with RCE for U.S. Appl. No. 13/335,404 dated Sep. 4, 2015.
Request for Reconsideration in U.S. Appl. No. 14/195,938 dated Jul. 31, 2015.
Final Office Action in U.S. Appl. No. 14/195,938 dated Sep. 3, 2015.
Third Office Action in CN 201180068364 dated Sep. 1, 2015.
Second Office Action in CN 201180068365.2 dated May 14, 2015.
Second Office Action in CN 201180068714.0 dated May 25, 2015.
Second Office Action in CN 201180068711.7 dated Jun. 26, 2015.
Search and Examination Report in SG 2013050109 dated Jun. 11, 2015.
Search Report and Written Opinion in SG 201305081.0 dated Nov. 27, 2014.
Written Opinion in SG 201305081.0 dated May 18, 2015.
Office Action in VN 1-2013-01903 dated May 25, 2015.
Office Action in VN 1-2013-01949 dated May 25, 2015.
Kim, et al., "Vitamin A and Carotenoids in Human Milk," J. Agric. Food Chem, Oct. 1990, vol. 38, pp. 1930-1933.
Sumiyoshi, et al., "Determination of Each Neutral Oligosaccharide in the Milk of Japanese Women during the Course of Lactation," Brit. J. Nutr., vol. 89, pp. 61-69 (Jan. 2003).
Uauy et al., "Role of Nucleotides in Intestinal Development and Repair: Implications for Infant Nutrition," J. Nutr., Aug. 1994, vol. 124, 1436S-1441S.
Asakuma et al., "Sialyl oligosaccharides of human colostrum: Changes in concentration during the first three days of lactation," Biosci. Biotechnol. Biochem., vol. 71(6), pp. 1447-1451 (2007).
Ashida, et al., "Two distinct alpha-L-fucosidases from Bifidobacterium bifidum are essential for the utilization of fucosylated milk oligosaccharides and glycoconjugates," Glycobiology, Vo. 19(9), pp. 1010-1017 (2009).
Bakker-Zierikzee, et al., "Effects of infant formula containing a mixture of galacto- and fructo-oligosaccharides or viable Bifidobacterium animalis on the intestinal microflora during the first 4 months of life," Br. J. Nutr., vol. 94(5), pp. 783-790 (2005).

(56) References Cited

OTHER PUBLICATIONS

Bao, et al., "Simultaneous quantification of sialyloligosaccharides from human milk by capillary electrophoresis," Anal. Biochem. Vol. 370 (2), pp. 206-214 (2007).
Barker, et al., "The colorimetric determination of lactic acid in biological materials," J. Biol. Chem., vol. 138, pp. 535-554 (1941).
Barrangou, et al., "Functional and comparative genomic analysis of an operon involved in fructooligosaccharide utilization by Lactobacillus acidophilus," Proceedings of the National Academy of Sciences of the United States of America, vol. 100(15), pp. 8957-8962 (2003).
Barrat et al., "Supplementation with galactooligosaccharides and inulin increases bacterial translocation in artificially reared newborn rats," Pediatr. Res., vol. 64(1), pp. 34-39 (2008).
Bezkorovainy, A., "Probiotics: determination of survival growth in the gut," Am. J. Clin. Nutr., vol. 73(2 Suppl.), pp. 399S-405S (2001).
Bode, L., "Human milk oligosaccharides: prebiotics and beyond," Nutr. Rev., vol. 67, pp. S183-S191 (2009).
Bode, et al., "Human milk-oligosaccharides reduce platelet-neutrophil complex formation leading to a decrease in neutrophil beta-2 integrin expression," J. Leukocyte Bio. vol. 76, pp. 820-826 (2004).
Bode, et al., "Inhibition of monocyte, lymphocyte and neutrophil adhesion to endothelial cells by human milk oligosaccharides," Thrombosis and Haemostasis, vol. 92(6), pp. 1402-1410 (2004).
Bode, L., "Recent advances on structure, metabolism, and function of human milk oligosaccharides," J. Nutr., vol. 136, pp. 2127-2130 (2006).
Boehm, et al., "Oligosaccharides from milk," J. Nutr., vol. 137 (3 Suppl. 2) p. 847S-849S (2007).
Boehm et al., "Prebiotic carbohydrates in human milk and formulas," Acta Paediatr. Suppl., vol. 94 (449), pp. 18-21 (2005).
Boehm, et al., "Prebiotic concept for infant nutrition," Acta Paediatr. Suppl., vol. 91(441), pp. 64-67 (2003).
Boehm et al., "Prebiotics in infant formulas," J. Clin. Gastroenterol., vol. 38(6 Suppl.), pp. S76-S79 (2004).
Boehm et al., "Supplementation of a bovine milk formula with an oligosaccharide mixture increases counts of faecal bifidobacteria in preterm infants," Arch. Dis. Child Fetal Neonatal Ed., vol. 86(3), pp. F178-F181 (2002).
Bouhnik et al., "Short chain fructo-oligosaccharide administration dose dependently increases fecal bifidobacteria in healthy humans," J. Nutr. Vol. 129, pp. 113-116 (1999).
Bourquin, et al., "Vegetable fiber fermentation by human fecal bacteria: cell wall polysaccharide disappearance and short-chain fatty acid production during in vitro fermentation and water-holding capacity of unfermented residues," J. Nutr., vol. 123, pp. 860-869 (1993).
Bruzzese et al., "A formula containing galacto- and fructo-oligosaccharides prevents intestinal and extra-intestinal infections: an observation study," Clin. Nutr., vol. 28(2), pp. 156-161 (2009).
Bryant, et al., "Cultural methods and some characteristics of some of the more numerous groups of bacteria in the bovine rumen," J. Dairy Sci., vol. 36, pp. 205-217 (1953).
Buck, "Effect of Dietary Ribonucleotides on Infant Immune Status, Part 2: Immune Cell Development," Pediatric Research, vol. 56(6), pp. 891-900 (2004).
Campbell, et al., "Selected indigestible oliogsaccharides affect large bowel mass, cecal and fecal short-chain fatty acids, pH and microflora in rats," J. Nutr., vol. 127(1), pp. 130-136 (1997).
Castro, et al., "Cutting Edge: IFN-y regulates the induction and expansion of IL-17-producing CD4 T cells during mycobacterial infection," The Journal of Immunology, vol. 177(3), pp. 1416-1420 (2006).
Chaturvedi, "Fucosylated human milk oligosaccharides vary between individuals and over the course of lactation," Glycobiology, vol. 11, pp. 365-372 (2001).
Chen, et al., "Probiotics and prebiotics: role in clinical disease states," Adv. Pediatr., vol. 52, pp. 77-113 (2005).

Cherbut, et al., "The prebiotic characteristics of fructooligosaccharides are necessary for reduction of TNBS-Induced Colitis in Rats,", J. of Nutr., vol. 133, pp. 21-27 (2003).
Chierici et al., "Advances in the modulation of the microbial ecology of the gut in the early infancy," Acta Paediatr. Suppl., vol. 91(441), pp. 56-63 (2003).
Cinquin, et al., "Comparative effects of exopolysaccharides from lactic acid bacteria and fructo-oligosaccharides on infant gut microbiota tested in an in vitro colonic model with immobilized cells," FEMS Microbiol. Ecol., Vo. 57(2), pp. 226-238 (2006).
Coppa et al., "Characterization of oligosaccharides in milk and feces of breast-fed infants by high performance anion-exchange chromatography," Adv. Exp. Med. Biol., vol. 501, pp. 307-314 (2001).
Coppa et al., "The first prebiotics in humans: human mild oligosaccharides," J. Clin. Gastroenterol., vol. 38 (Suppl. 2), pp. S80-S83 (2004).
Cummings, et al., "Gastrointestinal effects of prebiotics," Br. J. Nutr., vol. 87 (Suppl.2), pp. S145-S151 (2002).
Daddaoua, et al., "Goat Milk Oligosaccharides are Anti-Inflammatory in Rats with Hapten-Induced Colitis," Journal of Nutrition, vol. 136(3), pp. 672-676 (2006).
De la Fuente, et al., "Anti-oxidants as modulators of immune function," Immunology and Cell Biology, vol. 78, pp. 49-54 (2000).
De Vrese et al., "Probiotics, prebiotics and synbiotics,", Adv. Biochem. Eng. Biotechnol., vol. 111, pp. 1-66 (2008).
Douville, et al., "Human metapneumovirus elicits weak IFN-g memory responses compared with RSV," J. of Immun., vol. 176, pp. 5848-5855 (2006).
Dr. Bode presentation, "Human Milk Oligosaccharides, Only the Breast," T. Denny Sanford Pediatric Symposia, Apr. 24-26, 2009.
D'Sousa et al., "Effects of Probiotics, Prebiotics and Synbiotics on Messenger RNA Expression of Caveolin-1, NOS, and Genes Regulating Oxidative Stress in the Terminal Illeum of Formula-Fed Neonatal Rats," Pediatric Research, vol. 67, pp. 526-531 (2010).
Edwards et al., "Dietary fibre in infancy and childhood," Proc. Nutr. Soc., vol. 62(1), pp. 17-23 (2003).
Edwards, et al., "Intestinal flora during the first months of life: new perspectives," Br. J. Nutr., vol. 88 (Suppl. 1), pp. S11-S18 (2002).
Eiwegger, et al., "Human milk-derived oligosaccharides and plant-derived oligosaccharides stimulate cytokine production of cord blood t-cells in vitro," Pediatr. Res. vol. 56, pp. 536-540 (2004).
Eiwegger et al., "Prebiotic oligosaccharides: in vitro evidence for gastrointestinal epithilial transfer and immunomodulatory properties," Pediatric Allergy and Immunology, vol. 21(8), pp. 1179-1188 (2010).
Espinosa, et al., "Efforts to emulate human milk oligosaccharides," Br. J. of Nutr., vol. 98, pp. S74-S79 (2007).
Euler, et al., "Prebiotic effect on fructo-oligosaccharide supplemented term infant formula at two concentrations compared with unsupplemented formula and human milk," J. Pediatr. Gastroeneterol. Nutr., vol. 40, pp. 157-164 (2005).
Fanaro et al., "Acidic oligosaccharides from pectin hydrolysate as new component for infant formulae: effect on intestinal flora, stool characteristics and pH," J. Pediatr. Gastroenterol. Nutr., vol. 41(2), pp. 186-190 (2005).
Fanaro et al., "Galacto-oligosaccharides and long-chain fructo-oligosaccharides as prebiotics in infant formulas: a review," Acta Paediatr. Suppl. vol. 94 (449), pp. 22-26 (2005).
Fisberg et al., "Effect of oral nutritional supplementation with or without synbiotics on sickness and catch-up growth in pre-school children," Intern. Pediatr., vol. 17(4), pp. 216-222 (2002).
Flickinger, et al., "In vitro fermentation properties of selected frutoologisaccharide-containing vegetables and in vivo colonic microbial populations are affected by the diets of healthy human infants," J. Nutr., vol. 132(8), pp. 2188-2194 (2002).
Forsythe, et al., "Mood and gut feelings," Brain Behav. Immun., vol. 24(1), pp. 1-8 (2009).
Forsythe, et al., "Oral treatment with live Lactobacillus reuteri inhibits the allergic airway response in mice," Am. J. Respir. Crit. Care Med., vol. 175(6), pp. 561-569 (2007).

(56) References Cited

OTHER PUBLICATIONS

Forsythe, et al., "Probiotics in neurology and psychiatry," In Therapeutic Microbiology: Probiotics and Related Strategies, Versalovic, J., Wilson M., editor, Washington DC, ASM Press, pp. 285-298 (2008).
Friel, et al., "Milk from Mothers of Both Premature and Full-Term Infants Provides Better Antioxidant Protection than Does Infant Formula," Ped. Res., vol. 51(5), pp. 612-618 (2002).
Friesland Foods' Friso Gold Infant Formulas, http://www.friso.com/sg/products/frisogold2.php, last accessed Mar. 13, 2012.
German, et al., "Human milk oligosaccharides: evolution, structures and bioselectivity as substrates for intestinal bacteria," Nestle Nutr. Workshop Ser. Pediatr. Program, vol. 62, pp. 218-222 (2008).
Ghoddusi et al., "In vitro study on gas generation and prebiotic effects of some carbohydrates and their mixtures," Anaerobe, vol. 13, pp. 193-199 (2007).
Gibson, et al., "Dietary modulation of the human colonic microbiota: introducing the concept of prebiotics," J. Nutr., vol. 125(6), pp. 1401-1412 (1995).
Gill et al., "Development and application of a liquid chromatographic method for analysis of nucleotides and nucleosides in milk and infant formulas," Intern. Dairy Journal, vol. 17(6), pp. 596-605 (2007).
Gill, et al., "Differential recruitment of dendritic cells and monocytes to respiratory mucosal sites in children with Influenze Virus or Respiratory Syncytial Virus infection," J. of Infectious Disease, vol. 198, pp. 1667-1676 (2008).
Gonzalez et al., "Differential transcriptional response of Bifidobacterium longum to human milk, formula milk and galactooligosaccharide," Appl. Environ. Microbiol., vol. 74(15), pp. 4686-4694 (2008).
Grabitske et al., "Gastrointestinal effects of low-digestible carbohydrates," Crit. Rev. Food Sci. Nutr. vol. 49(4), pp. 327-360 (2009).
Gunnarsson, et al., "Sialic acid residues play a pivotal role in alpha 1-acid glycoprotein (AGP) induced generation of reactive oxygen species in chemotactic peptide pre-activated neutrophil granulocytes," Inflammation Research, vol. 59 (2), pp. 89-95 (2010).
Gutierez, et al., "Immune response to nucleotide-supplemented infant formulae: systematic review and meta-analysis," British Journal of Nutrition (2007), 98 (Suppl. 1), S64-S67 (2007).
Grazioso, "Antiinflammatory Effects of Human Milk on Chemically Induced Colitis in Rats," Pediatric Research, vol. 42 (5), pp. 639-643 (1997).
Grulee et al., "Breast and artificial feeding: influence of morbidity and mortality of twenty thousand infants," J. Am. Med. Assoc., vol. 103, pp. 735-738 (1934).
Hernot, et al., "In vitro fermentation profiles, gas production rates, and microbiota modulation as affected by certain fructans, galactooliogosaccharides, and polydextrose," J. Agr. Food Chem., vol. 57, pp. 1354-1361 (2009).
Hidaka, et al., "Effects of fructooligosaccharides on intestinal flora and human health," Bifidobacteria Microflora, vol. 5 (1), pp. 37-50 (1986).
"Human Breast Milk," Wikipedia, last accessed Feb. 2, 2012.
Idota et al., "Growth promoting effects of N-Acetylneuraminic acid-containing substances on bifidobacteria," Biosci. Biotech. Biochem. vol. 58, pp. 1720-1722 (1994).
Isaacs, "Human milk inactivates pathogens individually, additively, and synergistically," J. Nutr., vol. 135(5), pp. 1286-1288 (2005).
Jantscher-Krenn, et al., "Human milk oligosaccharides and their potential benefits for the breast-fed neonate," Minerva Pediatr., vol. 64, pp. 83-99 (2012).
Jyonouchi, et al., "Dietary ribonucleotides increase antigen-specific type 1 T-helper cells in the regional draining lymph nodes in young BALB/cJ mice," Nutrition, vol. 19(1), pp. 41-46 (2003).
Karimi, et al., "Lactobacillus reuteri induced regulatory T-cells protect against an allergic airway response in mice," Am. J. Resp. Crit. Care Med., vol. 179(3), pp. 186-193 (2009).
Kashyap et al., "Growth Nutrient Retention and Metabolic Response of Low birth-weight infants fed Supplemented and Unsupplemented Preterm Human Milk," American Journal of Clinical Nutrition, American Society for Nutrition, US, vol. 52(2), pp. 254-262 (1990).
Kasson, et al., "Structural basis for influence of viral glycanss on ligand binding by influenze hemagglutinin," Biophysical Journal, vol. 95(7), pp. L48-L50 (2008).
Kauth, et al., "Synergistically upregulated IL-10 production in cocultures of monocytes and T cells after stimulation with RSV," International Archives of Allergy and Immunology, vol. 142, pp. 116-126 (2007).
Kay, et al., "Mechanisms of T lymphocyte activation," Immunology Letters, vol. 29, pp. 51-54 (1991).
Khachik, et al., "Identification, Quantification, and Relative Concentrations of Carotenoids and their Metabolites in Human Milk and Serum," Analytical Chemistry, American Chemical Society, US, vol. 69(10), pp. 1873-1881 (1997).
Kien, "Digestion, absorption, and fermentation of carbohydrates in the newborn," Clin. Perinatol., vol. 23(2), pp. 211-228 (1996).
Kitaoka et al., "Novel putative galactose operon involving lacto-N-blose phosphorylase in Bifidobacterium longum," Appl. Environ. Microbiol., vol. 71(6), pp. 3158-3162 (2005).
Kiyohara et al., "An exo-{alpha}-sialidase from bifidobacteria involved in the degradation of sialyloliogsaccharides in human milk and intestinal glycoconjungates, "Glycobiology, vol. 21(4), pp. 437-447 (2011).
Kiyohara, et al., "Prebiotic effect of lacto-N-biose 1 on bifidobacterial growth," Biosci. Biotechnol. Biochem. vol. 73(5), pp. 1175-1179 (2009).
Knol, et al., "Colon microflora in infants fed formula with galacto- and fructo-oligosaccharides: more like breast-fed infants," J. Pediatr. Gastroenterol. Nutr., vol. 40(1), pp. 36-42 (2005).
Kobata, "Structures and application of oligosaccharides in human milk," Proc. Jpn. Acad. Ser. B. Phys. Biol. Sci., vol. 86(7), pp. 731-747 (2010).
Kulkarni et al., "Influence of dietary nucleotide restriction on bacterial sepsis and phagocytic cell function in mice," Arch. Surg., vol. 121(2), pp. 169-172 (1986).
Kuntz, et al., "Oligosaccharides from human milk induce growth arrest via G2/M by influencing growth-related cell cycle genes in intestinal epithelial cells," Br. J. Nutr. vol. 101, pp. 1306-1315 (2009).
Kuntz, et al., "Oligosaccharides from human milk influence growth-related characteristics of intestinally transformed and non-transformed intestinal cells," Br. J. Nutr. vol. 99, pp. 462-471 (2008).
Kunz, et al., "Biological functions of oligosaccharides in human milk," Acta paediatr., vol. 82(11), pp. 903-912 (1993).
Kunz, "Komplexe Oligosaccharides in der Saeuglingsernaehrung," Monatsschrift Fuer Kinderheilkunde, Springer Verlag, DE, vol. 146(1), pp. 49-56 (1998).
Kunz, et al., "Oligosaccharides in human milk: structural, functional and metabolic aspects," Annu. Rev. Nutr. vol. 20, pp. 699-722 (2000).
Kunz, et al., "Potential anti-inflammatory and anti-infectious effects of Human Milk Oligosaccharides," from Bioactive Components of Milk, Springer, pp. 455-465 (2008).
Kunze, et al., "Lactobacillus reuteri enhances excitability of colonic AH neurons by inhibiting calcium dependent potassium channel opening," J. Cell. Mol. Med., vol. 13(8B), pp. 2261-2270 (2009).
Kurokawa et al., "Comparative metagenomics revealed commonly enriched gene sets in human gut microbiomes," DAN Res., vol. 14, pp. 169-181 (2007).
Lara-Villoslada, "Oligosacccharides isolated from goat milk reduce intestinal inflammation in a rat model of dextran sodium sulfate-induced colitis," Clin. Nutr. vol. 25(3), pp. 477-488 (2006).
Leach, et al., "Total potentially available nucleosides of human milk by stage of lactation," Am. J. Clin. Nutr., vol. 61(6), pp. 1224-1230 (1995).
Lee et al., "Genomic insights into bifidobacteria," Microbiol. Mol. Biol. Rev., vol. 74(3), pp. 378-416 (2010).
Leyer, et al., "Probiotic effects on cold and influenza-like symptom incidence and duration in children," Pediatrics, vol. 124(2), pp. e172-e179 (2009).

(56) References Cited

OTHER PUBLICATIONS

LoCascio, et al., "A versatile and scalable strategy for glycoprofiling bifidobacterial consumption of human milk oligosaccharides," Microb. Biotechnol., vol. 2, pp. 333-342 (2009).
LoCascio, et al., "Broad conservation of milk utilization genes in bifidobacterium longum subsp. Infantis as revealed by comparative genomic hybridization," Appl. Environ. Microbiol., vol. 76(22), pp. 7373-7381 (2010).
LoCascio, et al., "Glycoprofiling of bifidobacterial consumption of human milk oligosaccharides demonstrates strain specific, preferential consumption of small chain glycans secreted in early human lactation," J. Agric. Food Chem., vol. 55(22), pp. 8914-8919 (2007).
Ma, et al., "Live lactobacillus reuteri is essential for the inhibitory effect of tumor necrosis factor alpha-induced interleukin-8 expression," Infect. Immun., vol. 72, pp. 5308-5314 (2004).
Maaheimo, "Synthesis of a divalent sialyl Lewis X O-glycan, a potent inhibitor of lymphocyte-endothelium adhesion. Evidence that multivalency enhances the saccharide binding to selectins," European Journal of Biochemistry, vol. 234, pp. 616-625 (1995).
Macfarlane, et al., "Bacterial metabolism and health-related effects of galacto-oligosaccharides and other prebiotics," J. Appl. Microbiol., vol. 104(2), pp. 305-344 (2008).
MacIver, et al., "Glucose metabolism in lymphocytes is a regulated process with significant effects on immune cell function and survival," J. Leukoc. Biol., vol. 84, pp. 949-957 (2008).
Magne, et al., "Effects on faecal microbiota of dietary and acidic oligosaccharides in children during partial formula feeding," J. Pediatr. Gastroenterol. Nutr., vol. 46(5), pp. 580-588 (2008).
Malhotra, et al, "Isolation and characterisation of potential respiratory syncytial virus receptor(s) on epithelial cells," Microbes and Infection, vol. 5, pp. 123-133 (2003).
Marcobal, et al., "Consumption of human milk oligosaccharides by gut-related microbes," J. Agric. Food Chem., vol. 58, pp. 5334-5340 (2010).
Mariat, "The Firmicutes/Bacteroidetes ratio of the human microbiota changes with age," BMC Microbiol., vol. 9, p. 123 (2009).
Marlett et al., "American Dietetic Association, Position of the American Dietetic Association: health implications of dietary fiber," J. Am. Diet. Assoc., vol. 102(7), pp. 993-1000 (2002).
Martin-Sosa et al., "Sialyloligosaccharides in human and bovine milk and in infant formulas: variations with the progression of lactation," J. Dairy Sci., vol. 86, pp. 52-59 (2003).
Martinez-Ferez, et al., "Goats' milk as a natural source of lactose-derived oligosaccharides: Isolation by membrane technology," Intern. Dairy J., vol. 16(2), pp. 173-181 (2006).
Masuko, et al., "Carbohydrate analysis by a phenol-sulfuric acid method in microplate format," Anal. Biochem. vol. 339, pp. 69-72 (2005).
McVeagh et al., "Human milk oligosaccharides: only the breast," J. Paediatr. Child Health, vol. 33(4), pp. 281-286 (1997).
McKellar, et al., "Metabolism of fructo-oligosaccharides by *bifidobacterium* spp.," Appl. Microbiol. Biotechnol., vol. 31, pp. 537-541 (1989).
Meinzen-Derr, "Role of human milk in extremely low birth weight infants' risk of necrotizing enterocolitis or death," J. Perinatology, vol. 29, pp. 57-62 (2009).
Michalek, et al., "Cutting Edge: Distinct Glycolytic and Lipid Oxidative Metabolic Programs are Essential for Effector and Regulatory CD4+ T Cell Subsets," J. of Immunology, vol. 186, pp. 3299-3303 (2011).
Miniello, et al., "Prebiotics in infant mild formulas: new perspectives," Acta Paediatr. Suppl., vol. 91 (441), pp. 68-76 (2003).
Miwa, et al., "Cooperation of beta-galactosidase and beta-N-acetylhexosamminidase from bifidobacteria in assimilation of human milk oligosaccharaides with type 2 structure," Glycobiology, vol. 20(11), pp. 1402-1409 (2010).
Monaco, et al., "The addition of the polydextrose and galactooliogossaccharide to formula does not affect barrier function or bacterial translocation in neonatal piglets," FASEB J., Meeting Abstract Supplement, vol. 23 LB479 (2009).

Moro, et al., "Dosage-related bifidogenic effects of galacto-and fructo-oligosaccharides in formula-fed term infants," J. Pediatr. Gastroenterol. Nutr., vol. 34 (3), pp. 291-295 (2002).
Moro, et al., "Effects of a new mixture of prebiotics on faecal flora and stools in term infants," Acta Paediatr. Suppl., vol. 91(441), pp. 77-79 (2003).
Moro et al., "Reproducing the bifidogenic effect of human milk in formula-fed infants: why and how ?", Acta Paediatr. Suppl. vol. 94(449), pp. 14-17 (2005).
Morrow, et al., "Human milk oligosaccharides are associated with protection against diarrhea in breast-fed infants," J. Pediatr., pp. 297-303 (2004).
Morrow, et al., "Novel salivary and genetic biomarkers of risk for NEC or death in premature infants," FASEB, vol. 23, (Meeting Abstract Supplement), LB270 (2009).
Morrow, et al., "Secretor phenotype and genotype are novel predictors of severe outcomes in premature infants," FASEB, vol. 24 (Meeting Abstract Supplement), p. 480.6 (2010).
Mountzouris et al., "Intestinal microflora of human infants and current trends for its nutritional modulation," Br. J. Nutr., vol. 87(5), pp. 405-420 (2002).
Nakamura et al., "Concentrations of sialyloligosaccharides in bovine colostrum and milk during the prepartum and early lactation," J. Dairy Sci., vol. 86, pp. 1315-1320 (2003).
Nakamura, et al., "Molecular ecological analysis of fecal bacterial populations from term infants fed formula supplemented with selected blends of prebiotics," Appl. Environ. Microbiol., vol. 75, pp. 1121-1128 (2009).
Nakhla, et al., "Neutral oligosaccharide content of preterm human milk," Br. J. Nutr. vol. 82, pp. 361-367 (1999).
Nakano, et al., "Sialicacid in human milk," Acta paediatrica taiwanica, vol. 42(1), pp. 11-17 (2001).
Navarro et al., "Influence of Dietary Nucleotides on Plasma Immunoglobulin Levels and Lymphocyte Subsets of Preterm Infants," Biofactors, vol. 10(1), pp. 67-76 (1999).
Newburg, et al., "Human milk glycans protect infants against enteri pathogens," Annu. Rev. Nutr., vol. 25, pp. 37-58 (2005).
Newburg, et al., "Innate protection conferred by fucosylated oligosaccharides of human milk against diarrhea in breastfed infants," Glycobiology, vol. 14(3), pp. 253-263 (2004).
Newburg, DS, "Neonatal protection by an innate immune system of human milk consisting of oligosaccharides and glycans," J. Anim. Sci., vol. 87 (13 Suppl.), pp. 26-34 (2009).
Newburg, DS, "Oligosaccharides in human milk and bacterial colonization," J. Pediatr. Gasterenterol. Nutr., vol. 30, pp. S8-S17 (2000).
Newburg, et al., "Protection of the neonate by the innate immune system of developing gut and of human milk," Ped. Res., vol. 61(1), pp. 2-8 (2007).
Nicholls et al., "Evolving complexities of influenza virus and its receptors," Trends in Microbiology, vol. 16(4), pp. 149-157 (2008).
Ninonuevo et al., "A strategy for annotating the human milk glycome," J. Agric. Food Chem., vol. 54, pp. 7471-7480 (2006).
Ninonuevo et al., "Mass spectrometric methods for analysis of oligosaccharides in human milk," Nutr. Rev., vol. 67 (Suppl. 2), pp. S216-S226 (2009).
Nwachuku, et al., "Health Risks of Enteric Viral Infections in Children," Reviews of Enivironmental Contamination and Toxicology (pp. 1-56), Springer New York (2006).
Palmer, et al., "Development of the human infant intestinal microbiota," PLoS Biol., vol. 5, p.e. 177, pp. 1556-1573 (2007).
Parrett et al., "In vitro fermentation of carbohydrated by breast fed and formula fed infants," Arch. Dis. Childhood, vol. 76, pp. 249-253 (1997).
Petschow, et al., "Response of bifidobacterium species to growth promoters in human and cow milk," Pediatr. Res., vol. 29(2), pp. 208-213 (1991).
Pickering, et al., "Modulation of the Immune System by Human Milk and Infant Formula Containing Nucleotides," Pediatrics, vol. 101(2), pp. 242-249 (1998).
Portelli, et al., "Effect of compounds with antibacterial activities in human milk on respiratory syncytial virus and cytomegalovirus in vitro," J. Med. Microbiol., vol. 47, pp. 1015-1018 (1998).

(56) References Cited

OTHER PUBLICATIONS

"Prevention" in Glossary of Medical Education Terms: Parts 1-7, Wojtczak, A. Ed. Medical Teacher, vol. 24 Nos. 2-6 and vol. 25, Nos. 1-2 (2002).
Probert, et al., "Polydextrose, lactitol, and fructo-oligosaccharide fermentation by colonic bacteria in a three-stage continuous culture system," Appl. Environ. Microbiol., vol. 70(8), pp. 4505-4511 (2004).
Rinne et al., "Similar bifidogenic effects of prebiotic-supplemented partially hydrolyzed infant formula and breastfeeding on infant gut microbia," Fems Immunology and Medical Microbiology, Elsevier Science BV, Amsterdam, vol. 43(1), pp. 59-65 (2005).
IPRP for PCT/US2011/067004 dated Jul. 2, 2013.
ISR and WO for PCT/US2011/067008 dated Mar. 29, 2012.
IPRP for PCT/US2011/067008 dated Jul. 2, 2013.
Invitation to Pay Additional Fees for PCT/US2011/067031 dated May 29, 2012.
ISR and WO for PCT/US2011/067012 dated May 24, 2012.
ISR and WO for PCT/US2011/067018 dated Mar. 27, 2012.
ISR and WO for PCT/US2011/067022 dated Jun. 11, 2012.
IPRP for PCT/US2011/067022 dated Jul. 2, 2013.
Invitation to Pay Additional Fees for PCT/US2011/067027 dated Mar. 27, 2012.
ISR and WO for PCT/US2011/067027 dated Jun. 11, 2012.
IPRP for PCT/US2011/067027 dated Jul. 2, 2013.
ISR and WO for PCT/US2011/067028 dated Mar. 27, 2012.
Office action for U.S. Appl. No. 13/334,995 dated Apr. 22, 2013.
Final office action for U.S. Appl. No. 13/334,995 dated Sep. 17, 2013.
Response after final office action for U.S. Appl. No. 13/334,995 dated Dec. 11, 2013.
Advisory Action in U.S. Appl. No. 13/334,995 dated Jan. 22, 2014.
Response to Final Office Action in U.S. Appl. No. 13/334,995 dated Feb. 7, 2014.
Applicant-Initiated Interview Summary for U.S. Appl. No. 13/334,995 dated Feb. 11, 2014.
Notice of Allowance for U.S. Appl. No. 13/334,995 dated Feb. 19, 2014.
Restriction Requirement for U.S. Appl. No. 13/335,018 dated Jun. 3, 2013.
Response to Restriction Requirement for U.S. Appl. No. 13/335,018 dated Jul. 3, 2013.
Office Action in U.S. Appl. No. 13/335,018 dated Aug. 14, 2013.
Response to Office Action in U.S. Appl. No. 13/335,018 dated Dec. 4, 2013.
Final Office Action in U.S. Appl. No. 13/335,018 dated Apr. 4, 2014.
Office Action in U.S. Appl. No. 13/335,433 dated Apr. 22, 2013.
Response to Office Action in U.S. Appl. No. 13/335,433 dated Jul. 18, 2013.
Final Office Action in U.S. Appl. No. 13/335,433 dated Sep. 6, 2013.
Response to Final Office Action in U.S. Appl. No. 13/335,433 dated Nov. 5, 2013.
Advisory Action in U.S. Appl. No. 13/335,433 dated Nov. 20, 2013.
Letter requesting interview with Examiner for U.S. Appl. No. 13/335,433 dated Nov. 21, 2013.
Applicant-Initiated Interview Summary for U.S. Appl. No. 13/335,433 dated Dec. 6, 2013.
Response with RCE to Final Office Action for U.S. Appl. No. 13/335,433 dated Jan. 2, 2014.
Office Action for U.S. Appl. No. 13/335,433 dated Mar. 14, 2014.
Office Action for U.S. Appl. No. 13/335,404 dated Aug. 19, 2013.
Response to Office Action for U.S. Appl. No. 13/335,404 dated Nov. 19, 2013.
Final Office Action for U.S. Appl. No. 13/335,404 dated Mar. 13, 2014.
Response to Final Office Action for U.S. Appl. No. 13/335,404 dated May 12, 2014.
Advisory Action Before the Filing of an Appeal Brief for U.S. Appl. No. 13/335,404 dated May 22, 2014.

First Exam Report in NZ Application 612,105 dated Dec. 24, 2013.
Exam report in NZ Application 612,472 dated Dec. 19, 2013.
First Exam Report in NZ Application 613,165 dated Dec. 20, 2013.
First Exam Report in NZ Application 613,180 dated Dec. 20, 2013.
Abbott's Gain with Immunity Ingredients, available at http://www.abbott.com.sg/family products/children/gain.asp, last accessed Mar. 13, 2012.
Abbott's Similac with Immunity Ingredients, available at http://www.abbott.com.sg/family/products/children/similac_follow_on.asp, last accessed Mar. 13, 2012.
Albermann et al., "Synthesis of the milk oligosaccharide 2-fucosyllactose using recombinant bacterial enzymes," Carbohydrate Research, vol. 334(2), pp. 97-103 (2001).
Aggett et al., "Nondigestible carbohydrates in the diets of infants and young children: a commentary by the ESPGHAN Committee on Nutrition," vol. 36(3), pp. 329-337 (2003).
Armogida, "Identification and quantification of innate immune system mediators in human breast milk," Allergy and Asthma Proceedings, vol. 25(5), pp. 297-304 (2004).
Arslanoglu et al., "Early dietary intervention with a mixture of prebiotic oligosaccharides reduces the incidence of allergic manifestations and infections during the first two years of life," J. Nutr., vol. 138(6), pp. 1091-1095 (2008).
Arslanoglu et al., "Early supplementation of prebiotic oligosaccharides protects formula-fed infants against infections during the first 6 months of life," J. Nutr., vol. 137(11), pp. 2420-2424 (2007).
ISR for PCT/US2011/043644 dated Feb. 17, 2012.
ISR and WO for PCT/US2011/067004 dated Jun. 11, 2012.
Wu, et al., "Development of an Annotated Library of Neutral Human Milk Oligosaccharides," J. Proteome Res., vol. 9, pp. 4138-4151 (2010).
Xiao, et al., "Distribution of in vitro fermentation ability of lacto-N-biose I, a major building block of human milk oligosaccharides, in bifidobacterial strains," Appl. Environ. Microbiol., vol. 76(1), pp. 54-59 (2010).
Yamada, et al., "Lactotriaose-containing carbosilane dendrimers: Synthesis and lectin-binding activities," Bioorganic & Medicinal Chemistry, vol. 15(4), pp. 1606-1614 (2007).
Yamazaki, et al., "Measurement of growth of bifidobacteria on inulofructosaccharides," Let. Appl. Microbiol., vol. 10, pp. 229-232 (1990).
Yau, et al., "Effect of nucleotides on diarrhea and immune responses in healthy term infants in Taiwan," J. Pediatr. Gastro. Nutr., vol. 36(1), pp. 37-43 (2003).
Yoshida et al., "Role of N-3 polyunsaturated fatty acids and sialic acid in learning performance of rats," J. of Neurochemistry, vol. 65 (Suppl.), p. S173 (1995).
Yu, et al., "Improved extraction of PCR-quality community DNA from digesta and fecal samples," BioTechniques, vol. 36, pp. 808-812 (2004).
Yuhas, et al., "Human milk fatty acid composition from nine countries varies most in DHA," Lipids, vol. 41(9), pp. 851-858 (2006).
Ziegler et al., "Term infants fed formula supplemented with selected blends of prebiotics grow normally and have soft stools similar to those reported for breast-fed infants," J. Pediatr. Gastroenterol. Nutr., vol. 44, pp. 359-364 (2007).
Zivkovic et al., "Microbes and health sackler colloquium: Human mild glycobiome and its impact on the infant gastrointestinal microbiota," Proc. Natl. Acad. Sci. USA (2010).
Response in U.S. Appl. No. 13/335,433 dated May 30, 2014.
Response in U.S. Appl. No. 13/335,995 dated Aug. 22, 2013.
Amendment in U.S. Appl. No. 13/335,018 dated Jun. 20, 2014.
Notice of Allowance for U.S. Appl. No. 13/335,433 dated Jun. 24, 2014.
Response with RCE to Final Office Action for U.S. Appl. No. 13/335,404 dated Jun. 10, 2014.
English translation of First Office Action in CN 201180068364.8 dated May 26, 2014.
English translation of First Office Action in CN 201180066365.9 dated Jun. 26, 2014.
English translation of First Office Action in CN 201180068714.0 dated Jul. 8, 2014.

(56) References Cited

OTHER PUBLICATIONS

Communication for EP Application No. 11811267.1 dated Aug. 14, 2014.
Communication for EP Application No. 11810764.8 dated Aug. 8, 2014.
First Office Action in CN 201180068711.7 dated Aug. 12, 2014.
Office Action in U.S. Appl. No. 13/335,018 dated Nov. 24, 2014.
Office Action in U.S. Appl. No. 13/335,404 dated Oct. 15, 2014.
Downham, et al., "Breast-feeding protects against respiratory sycytial virus infections," British Medical Journal, 2 (6030), pp. 274-276(1976).
Mastretta et al., "Effect of Lactobacillus GG and breast-feeding in the prevention of rotavirus nosocomial infection," Journal of Pediatric Gastroenterology and Nutrition, vol. 35(4), pp. 527-531 (2002).
Pullan et al., "Breast-feeding and respiratory syncytial virus infection," British Medical Journal, 281 (6247), pp. 1034-1036.(1980).
Schlimme, et al., "Nucleosides and nucleotides: natural bioactive substances in milk and colostrum," British Journal of Nutrition, vol. 84(S1), ppl. 59-68 (2000).
Sheeran, et al., "Elevated cytokine concentrations in the nasopharyngeal and tracheal secretions of children with respiratory syncytial virus disease," The Pediatric Infectious Disease Journal, vol. 18(2), pp. 115-122 (Feb. 1999).
Terrazas, et al., "The schistosome oligosaccharide lacto-N-neotetraose expands Gr1+ cells that secrete anti-inflammatory cytokines and inhibit proliferation of naive CD4+ cells: a potential mechanism for immune polarization in helminth infections," The Journal of Immunology, 167(9), 2001, pp. 5294-5303.
Response to Office Action in U.S. Appl. No. 13/335,404 dated Jan. 12, 2015.
Rivero-Urgell, et al., "Oligosaccharides: application in infant food," Early Hum. Dev., vol. 65 (Suppl.), pp. S43-S52 (2001).
Roberfroid, "Prebiotics: the concept revisited," J. Nutr., vol. 137, p. 830S-837S (2007).
Rueda et al., "Influence of dietary compounds on intestinal immunity," Microbiol. Ecol. Health Diseases, vol. 2, p. 146S-156S (2000).
Rumessen, JJ, "Fructose and related food carbohydrates. Sources, intake, absorption, and clinical implications," Scand. J. Gastroenterol., vol. 27(10), pp. 819-828 (1992).
Rycroft et al., "A comparative in vitro evaluation of the fermentation properties of prebiotic oligosaccharides," J. Appl. Microbiol., vol. 91, pp. 878-887 (2001).
Saedisomeolia et al., "Lycopene enrichment of cultured epithelial cells decreases the inflammation induced by rhinovirus infection and lipopolysaccharide", J. Nutritional Biochemistry, vol. 20, p. 577-585 (2009).
Salminen, et al., "Microbial-host interactions: selecting the right probiotics and prebiotics for infants," Nestle Nutr. Workshop Ser. Pediatr. Program, vol. 64, pp. 201-213 (2009).
Schaffer, et al., "Ammonia saturation constants for predominant species of rumen bacteria," J. Dairy Sci., vol. 63(8), pp. 1248-1263 (1980).
Schaller, et al., "Effect of Dietary Ribonucleotides on Infant Immune Status Part 1: Humoral Responses," Pediatric Research, vol. 56(6), pp. 883-890 (2004).
Schmelzle et al., "Randomized double-blind study of the nutritional efficacy and bifidogenicity of a new infant formula containing partially hydrolozed protein, a high beta-palmitic acid level, and non-digestible oligosaccharides," J. Pediatr. Gastroenterol. Nutr. vol. 36(3), pp. 343-351 (2003).
Schnabl et al., "Gangliosides protect bowel in an infant model of necrotizing enterocolitis by suppressing proinflammatory signals," J. Pediatr. Gastroenter. Nutr., vol. 49, pp. 382-392 (2009).
Scholtens, et al., "Bifidogenic effects of solid weaning foods with added prebiotic oligosaccharides: a randomised controlled clinical trial," J. Pediatr. Gastroenterol. Nutr., vol. 42(5), pp. 553-559 (2006).
Schrezenmeir, et al., "Benefits of oral supplementation with and without synbiotics in young children with acute bacterial infections," Clin. Pediatr. vol. 43(3), pp. 239-249 (2004).
Sela, et al., "The genome sequence of *Bifidobacterium longum* subsp. Infantis reveals adaptations for milk utilization within the infant microbiome," Proc. Natl. Acad. Sci., USA, vol. 105 (48), p. 18964-18969 (2008).
Sela et al., "Nursing our microbiota: molecular linkages between bifidobacteria and milk oligosaccharides," Trends Microb., vol. 18(7), pp. 298-307 (2010).
Sherman, et al., "Potential roles and clinical utility of prebiotics in newborns, infants and children," Proceedings from a global prebiotic summit meeting, New York City, Jun. 27-28, 2008, J. Pediatr., vol. 155(5), pp. S61-S70 (2009).
Sotgiu, et al., "Immunomodulation of fucosyl-lactose and lacto-N-fucopentaose on mononuclear cells from multiple sclerosis and healthy subjects," Inter. J. Biomedical Sci., vol. 2(2), pp. 114-120 (2006).
Soukup, et al., "Role of monocytes and eosinophils in human RSV infection in vitro," Clinical Immunology, vol. 107, pp. 178-185 (2003).
Spurell, et al., "Human airway epithelial cells produce IP-10 (CXCL 10) in vitro and in vivo upon rhinovirus infection," Am. J. Physiol. Lung Cell Mol. Physiol., vol. 289, pp. L85-L95 (2005).
Stevens, et al., "Glycan microarray analysis of the hemagglutinins from modern and pandemic influenza viruses reveals different receptor specificities," Journal of Molecular Biology, vol. 355, pp. 1143-1155 (2006).
Stevens, et al., "Structure and receptor specificity of the Hemagglutinin fron an H5N1 influenza virus," Science, vol. 312, pp. 404-410 (2006).
Stewart, et al., "Fructooligosaccharides exhibit more rapid fermentation than long-chain inulin in an in vitro fermentation system," Nutr. Res., vol. 28, pp. 329-334 (2008).
Sun, X., "Recent anti-influenza strategies in multivalent sialyloligosaccharides and sialylmimetics approaches," Current Medicinal Chemistry, vol. 14, pp. 2304-2313 (2007).
Suzuki et al., "Receptor specificities of human respiroviruses," J. of Virol., vol. 75(10), pp. 4604-4613 (2001).
Szylit et al., "Physiological and pathophysiological effects of carbohydrate fermentation," World Rev. Nutr. Diet, vol. 74, pp. 88-122 (1993).
Teneberg, et al., "Inhibition of nonopsonic Heliobacter pylori-induced activation of human neutrophils by sialylated oligosaccharides," Glycobiology, vol. 10(11), pp. 1171-1181 (2000).
Thurl, et al., "Variation of human milk oligosaccharides in relation to milk groups and lactational periods," Br. J. of Nutr., vol. 104(9), pp. 1261-1271 (2010).
Thurl, et al., "Variation of neutral oligosaccharides and lactose in human milk during the feeding," Zeitschrift fuer Ernaehrungswissenschaft, Steinkopf Verlag, Darmstadt, DE vol. 32(41), pp. 262-269 (1993).
Thymann, et al., "Formula feeding reduces lactose digestive capacity in neonatal pigs," British Journal of Nutrition, vol. 95, pp. 1075-1081 (2006).
Tijerina-Saenz, "Antioxidant capacity of human milk and its association with vitamins A and E and fatty acid composition," Acta Paediatrica, vol. 98(11), pp. 1793-1798 (2009).
Tsopmo et al., "Human milk has anti-oxidant properties to protect premature infants," Current Pediatric Reviews, vol. 3, pp. 45-51 (2007).
Vandenplas, Y., "Oligosaccharides in infant formula," Br. J. Nutr., vol. 87 (Suppl. 2), pp. S293-S296 (2002).
Varki, "Biological roles of oligosaccharides: all of the theories are correct," Glycobiology, vol. 3(2), pp. 97-130 (1993).
Veereman, G., "Pediatric applications of inulin and oligofructose," J. Nutr., vol. 137 (11 Suppl.), p. 2585S-2589S (2007).
Veereman-Wauters, G., "Application of prebiotics in infant foods," Br. J. Nutr., vol. 93 (Suppl. 1), pp. S57-S60 (2005).
Vester Boler, et al., "Carbohydrates blended with polydextrose lower gas production and short-chain fatty acid production in an in vitro system," Nutr. Res. vol. 29, pp. 631-639 (2009).

(56) References Cited

OTHER PUBLICATIONS

Videla, et al., "Dietary inulin improves distal colitis induced by dextran sodium sulfate in the ratinul in in dextran sodium sulfate colitis," Am J. of Gastro., vol. 96, pp. 1486-1493 (2001).
Von Nicolai, et al., "Partial purification and properties of neuraminidase from Bifidobacterium lacentis," Hoppe Seylers Z Physiol. Chem., vol. 362(2), pp. 153-162 (1981).
Vos, et al., "Dietary supplementation of neutral and acidic oligosaccharides enhances Th1-dependent vaccination responses in mice," Pediatr. Allergy Immunol., vol. 18(4), pp. 304-312 (2007).
Wada, et al., "Bifidobacterium bifidum lacto-N-biosidase, a critical enzyme for the degradation of human milk oliogosaccharides with a type 1 structure," Appl. Environ. Microbiol., vol. 74(13), pp. 3996-4004 (2008).
Walker, A., "Milk and two oligosaccharides," Nat. Rev. Microbiol., vol. 7(7), p. 483 (2009).
Wang et al., "Effects of the in vitro fermentation of oligofructose and inulin by bacteria growing in the human large intestine," J. Appl. Bacteriol., vol. 75, pp. 373-380 (1993).
Wang et al., "The role and potential of sialic acid in human nutrition," European Journal of Clinical Nutrition, vol. 57 (11), pp. 1351-1369 (2003).
Ward, "In vitro fermentation of breast milk oligosaccharides by Bifodobacterium infantis and Lactobacillus gasseri", Appl. Environ. Microbiol. vol. 72, pp. 4497-4499 (2006).
Ward, "In vitro fermentability of human milk oligosaccharides by several strains of bifidobacteria," Mol. Nutr. Food Res., vol. 51, pp. 1398-1405 (2007).
Westerbeek, et al., "Design of a randomised controlled trial on immune effects of acidic and neutral oligosaccharides in the nutrition of preterm infants: carrot study," BMC Pediatr., vol. 23, pp. 8-46 (2008).
Westerbeek, et al., "The effect of enteral supplementation of a prebiotic mixture of non-human milk galacto, fructo- and acidic oligosaccharides on intestinal permeability in preterm infants," Br. J. Nutr. vol. 105, pp. 268-274 (2011).
Wilson, M., "The gastrointestinal tract and its indigenous microbiota", Microbial Inhabitants of Humans: their ecology and role in health and disease, Cambridge University Press, pp. 283-287 (2005).
Wong, et al., "Colonic health: fermentation and short chain fatty acids," J. Clin. Gastroenterol., vol. 40(3), pp. 235-243 (2006).
Response and Request for Reconsideration in U.S. Appl. No. 13/335,018 dated Sep. 25, 2015.
Notice of Allowance and Examiner-Initiated Interview Summary for U.S. Appl. No. 13/335,018 dated Oct. 30, 2015.
Amendment with RCE for U.S. Appl. No. 14/195,938 dated Dec. 2, 2015.
Non final Office Action in U.S. Appl. No. 14/195,938 dated Jan. 29, 2016.
English translation of Third Office Action in CN 201180068365.2 dated Nov. 30, 2015.
English translation of Third Office Action in CN 201180068714.0 dated Dec. 4, 2015.
English translation of Third Office Action in CN 201180068711.7 dated Jan. 6, 2016.
Written Opinion for SG 201305074.5 dated Oct. 16, 2015.
Written Opinion in SG 201305084.4 dated Oct. 19, 2015.
English translation of Search Report in TW Application No. 100149998 dated Oct. 19, 2015.
English translation of Office Action in TW Application No. 100149998 dated Oct. 22, 2015.
English translation of Search Report in TW Application No. 100150002 dated Dec. 15, 2015.
Yuquan, LV et al., "Biological Functions of Human Milk Oligosaccharide," Food Science, No. 9, vol. 23, (Dec. 31, 2002), pp. 144-147 (abstract can be found in office action).
Office Action in U.S. Appl. No. 13/335,404 dated Apr. 21, 2016.
Amendment for U.S. Appl. No. 13/335,404 dated Sep. 21, 2016.
Office Action in U.S. Appl. No. 13/335,404 dated Dec. 12, 2016.
Final Office Action in U.S. Appl. No. 14/195,938 dated Aug. 31, 2016.
Fourth Office Action in CN 201180068364.8 dated May 6, 2016.
Decision on Rejection in CN 201180068365.2 dated Jun. 20, 2016.
Fourth Office Action in CN 201180068714.0 dated Jun. 8, 2016.
Third Office Action in CN 201180068711.7 dated Jan. 6, 2016.
Fourth Office Action in CN 201180068711.7 dated Sep. 18, 2016.
Communication for EP Application No. 11810764.8 dated May 4, 2016.
Communication for EP Application No. 11809048.9 dated Jul. 21, 2016.
Exam Report in Indonesian Application No. W00201302792 dated Jan. 29, 2016.
Office Action in MX/a/2013/007676 dated May 31, 2016.
Office Action in MX/a/2013/007679 dated Oct. 4, 2016.
Office Action in MX/a/2013/007684 dated Jul. 12, 2016.
Final Examination Report for SG 2013050745 dated May 19, 2016.
Final Examination Report for SG 201305081-0 dated Aug. 29, 2016.
Office Action in U.S. Appl. No. 15/804,751 dated Jan. 30, 2018.
Office Action in U.S. Appl. No. 15/844,294 dated Jan. 31, 2018.
Office Action from Canadian Application No. 2,822,222 dated Dec. 13, 2017.
Office Action from Canadian Application No. 2,822,495 dated Dec. 11, 2017.
Reexamination Notice in CN 201180068714.0 dated Jan. 8, 2018.
English translation of Decision on Rejection in CN 201180068714.0 dated Jan. 13, 2017.
English Summary of Office Action in MX/a/2013/007706 dated Mar. 21, 2017 (reported Mar. 23, 2017).
English Summary of Office Action in MX/a/2013/007706 dated Jun. 20, 2017 (reported Jun. 26, 2017).
English Summary of Office Action in MX/a/2013/007706 dated Oct. 10, 2017 (reported Oct. 16, 17).
Emmett et al., "Properties of Human Milk and Their Relationship with Maternal Nutrition," Early Human Development, 49 Suppl. (1997) pp. S7-S28.
Office Action in U.S. Appl. No. 15/019,496 dated Jul. 10, 2019.
Response to Office Action in U.S. Appl. No. 15/844,294 dated Aug. 19, 2019.
Response to Office Action from U.S. Appl. No. 15/818,374 dated May 31, 2019.
Office Action from U.S. Appl. No. 15/818,374 dated Jul. 5, 2019.
Response to Office Action from U.S. Appl. No. 15/892,234 dated Aug. 19, 2019.
Office Action from U.S. Appl. No. 15/707,477 dated May 23, 2019.
Office Action in MX/a/2017/001953 dated Jun. 25, 2019 with English Summary.
Office Action in MX/a/2018/002900 dated Jul. 19, 2019 with English Summary.
Amendment in U.S. Appl. No. 15/019,496 dated Apr. 29, 2019.
Office Action in U.S. Appl. No. 15/804,751 dated Mar. 19, 2019.
Examiner Initiated Interview Summary from U.S. Appl. No. 15/844,294 dated Mar. 19, 2019.
Response to Office Action from U.S. Appl. No. 15/844,294 dated Mar. 20, 2019.
Office Action from U.S. Appl. No. 15/844,294 dated Apr. 19, 2019.
Office Action in U.S. Appl. No. 15/866,322 dated Apr. 3, 2018.
Examiner Interview Summary from U.S. Appl. No. 15/866,322 dated Mar. 19, 2019.
Office Action from U.S. Appl. No. 15/866,322 dated Mar. 25, 2019.
Examiner Interview Summary from U.S. Appl. No. 15/836,552 dated Mar. 19, 2019.
Response to Office Action from U.S. Appl. No. 15/836,552 dated Apr. 15, 2019.
Office Action from U.S. Appl. No. 15/836,552 dated Apr. 25, 2019.
Response to Office Action from U.S. Appl. No. 15/874,604 dated Apr. 19, 2019.
Notice of Allowance from U.S. Appl. No. 15/874,604 dated May 6, 2019.
Examiner Initiated Interview Summary from U.S. Appl. No. 15/892,169 dated Mar. 19, 2019.

(56) References Cited

OTHER PUBLICATIONS

Response to Office Action from U.S. Appl. No. 15/892,169 dated Apr. 1, 2019.
Office Action from U.S. Appl. No. 15/892,169 dated Apr. 25, 2019.
Office Action from U.S. Appl. No. 15/892,234 dated Mar. 19, 2019.
Office Action from U.S. Appl. No. 15/893,112 dated Apr. 4, 2019.
Examiner Initiated Interview Summary from U.S. Appl. No. 15/893,286 dated Mar. 19, 2019.
Office Action from U.S. Appl. No. 15/893,286 dated Mar. 25, 2019.
Office Action from Canadian Application No. 2,822,495 dated Feb. 18, 2019.
Extended Search Report from European Patent Application No. 18210271.5 dated Mar. 19, 2019.
Search Report from EP Application No. 19159471.2 dated Apr. 4, 2019.
Birch et al., "The Diamond (DHA Intake and Measurement of Neural Development) Study: a Double-Masked, Randomized Controlled Clinical Trial of the Maturation of Infant Visual Acuity as Function of the Dietary Level of Docosahexaenoic Acid 1-3", Am J Clin Nutr 2010; pp. 848-859.
Hoffman et al., "Soy-Based Infant Formula Supplemented with DHA and ARA Supports Growth and Increases Circulating Levels of these Fatty Acids in Infants," Lipids (2008); 43; pp. 29-35.
Liquid—Definition for English-Language Learners from Merriam-Webster's Learner's Dictionary (http://www.learnersdictionary.com/ definition/liquid) viewed Apr. 4, 2019.
Miller et al., Erythrocyte Membrane Fatty Acid Content in Infants Consuming Formulas Supplemented with Docasahexaenoic Acid (DHA) and Arachidonic Acid (ARA) "an Observational Study", Maternal & Child Nutrition (2010), vol. 6, pp. 338-346.
Noah et al., Nasal Cytokine Production in Viral Acute Upper Respiratory Infection of Childhood, Journal of Infectious Diseases, Mar. 1995, pp. 584-592.
Powder—Definition for English-Language Learners from Merriam-Webster's Learner's Dictionary (http://www.learnersdictionary.com /definition/powder) viewed Apr. 4, 2019.
Response to Office Action in U.S. Appl. No. 15/019,496 dated Mar. 19, 2018.
Office Action in U.S. Appl. No. 15/019,496 dated Jul. 5, 2018.
Response to Office Action in U.S. Appl. No. 15/019,496 dated Oct. 5, 2018.
Office Action in U.S. Appl. No. 15/019,496 dated Dec. 27, 2018.
Office Action with Applicant Initiated Interview Summary in U.S. Appl. No. 15/804,751 dated Apr. 3, 2018.
Response to Office Action in U.S. Appl. No. 15/804,751 dated Jul. 3, 2018.
Office Action in U.S. Appl. No. 15/804,751 dated Oct. 30, 2018.
Response Office Action in U.S. Appl. No. 15/804,751 dated Feb. 28, 2019.
Response to Office Action in U.S. Appl. No. 15/844,294 dated Apr. 30, 2018.
Office Action in U.S. Appl. No. 15/844,294 dated Aug. 8, 2018.
Response to Office Action in U.S. Appl. No. 15/844,294 dated Nov. 8, 2018.
Applicant Interview Summary in U.S. Appl. No. 15/844,294 dated Nov. 29, 2018.
Office Action in U.S. Appl. No. 15/844,294 dated Dec. 20, 2018.
Response to Office Action in U.S. Appl. No. 15/866,322 dated Aug. 3, 2018.
Office Action in U.S. Appl. No. 15/866,322 dated Dec. 10, 2018.
Response to Office Action in U.S. Appl. No. 15/866,322 dated Mar. 11, 2019.
Office Action from U.S. Appl. No. 15/818,374 dated Mar. 29, 2018.
Response to Office Action from U.S. Appl. No. 15/818,374 dated Jun. 29, 2018.
Office Action from U.S. Appl. No. 15/818,374 dated Sep. 21, 2018.
Response to Office Action from U.S. Appl. No. 15/818,374 dated Dec. 21, 2018.
Office Action from U.S. Appl. No. 15/818,374 dated Jan. 31, 2019.
Office Action from U.S. Appl. No. 15/836,552 dated Apr. 19, 2018.
Response to Office Action from U.S. Appl. No. 15/836,552 dated Jul. 19, 2018.
Office Action from U.S. Appl. No. 15/836,552 dated Nov. 14, 2018.
Office Action form U.S. Appl. No. 15/874,604 dated Mar. 29, 2018.
Response to Office Action form U.S. Appl. No. 15/874,604 dated Jun. 29, 2018.
Office Action from U.S. Appl. No. 15/874,604 dated Aug. 7, 2018.
Response to Office Action form U.S. Appl. No. 15/874,604 dated Oct. 9, 2018.
Notice of Allowance from U.S. Appl. No. 15/874,604 dated Oct. 26, 2018.
Notice of Allowance from U.S. Appl. No. 15/874,604 dated Nov. 8, 2018.
Office Action from U.S. Appl. No. 15/874,604 dated Mar. 8, 2019.
Office Action from U.S. Appl. No. 15/892,169 dated Apr. 6, 2018.
Response to Office Action from U.S. Appl. No. 15/892,169 dated Jul. 6, 2018.
Office Action from U.S. Appl. No. 15/892,169 dated Oct. 30, 2018.
Office Action from U.S. Appl. No. 15/892,234 dated Apr. 2, 2018.
Response to Office Action from U.S. Appl. No. 15/892,234 dated Jul. 2, 2018.
Office Action from U.S. Appl. No. 15/892,234 dated Oct. 30, 2018.
Response to Office Action from U.S. Appl. No. 15/892,234 dated Feb. 28, 2019.
Office Action from U.S. Appl. No. 15/893,112 dated Apr. 10, 2018.
Response to Office Action from U.S. Appl. No. 15/893,112 dated Jun. 8, 2018.
Office Action from U.S. Appl. No. 15/893,112 dated Jul. 19, 2018.
Response to Office Action from U.S. Appl. No. 15/893,112 dated Oct. 19, 2018.
Office Action from U.S. Appl. No. 15/893,112 dated Nov. 29, 2018.
Response to Office Action from U.S. Appl. No. 15/893,112 dated Feb. 28, 2019.
Office Action from U.S. Appl. No. 15/893,286 dated Apr. 6, 2018.
Response to Office Action from U.S. Appl. No. 15/893,286 dated Aug. 6, 2018.
Final Office Action from U.S. Appl. No. 15/893,286 dated Dec. 11, 2018.
Response to Office Action from U.S. Appl. No. 15/893,286 dated Mar. 11, 2019.
Office Action from U.S. Appl. No. 15/707,477 dated Oct. 3, 2018.
Response to Office Action from U.S. Application No. 15/707,477 Feb. 4, 2019.
Office Action from Canadian Application No. 2,822,495 dated Jul. 24, 2018.
Office Action from Canadian Application No. 2,822,490 dated Nov. 21, 2017.
Office Action from Canadian Application No. 2,822,490 dated Dec. 21, 2018.
Office Action from Canadian Application No. 2,822,664 dated Nov. 20, 2017.
English translation of Decision on Rejection in CN 201180068714.0 dated Aug. 2, 2018.
Notice of Reexamination in CN 201180068711.7 and English Translation dated Jul. 12, 2018.
Reexamination in CN 201180068711.7 and English Translation dated Nov. 21, 2018.
Extended Search Report from EP Application No. 18157361.9 dated May 8, 2018.
Office Action from Indian Application No. 5653/DELNP/2013 dated Mar. 15, 2018.
Examination Report in Indonesian Application No. W00201302748 dated Feb. 26, 2018.
Examination Report in Indonesian Application No. W00201302800 dated Feb. 3, 2018.
Substantive Examination Report from PH Application No. 1-2013-501358 dated Jan. 5, 2018.
Office Action in Vietnamese Application 1-2013-01903 dated Nov. 19, 2018.
Office Action for Vietnamese Application 1-2013-01949 dated Nov. 19, 2018.
Office Action in Vietnamese Application No. 1-2013-02041 dated Aug. 31, 2018.

(56) References Cited

OTHER PUBLICATIONS

Barbosa-Canovas et al. "Food Powders: Physical Properties, Proessing, and Functionaity," Kluwer Academic/Plenum Publishers, NY, Chapter 3, 2005.
Ben "Nutritional Management of Newborn Infants: Practical Guidelines" Gastroentrol (2008), vol. 14, pp. 6133-6139.
Celestino et al., "The Effects of Refrigerated Storage of Raw Milk on the Quality of Whole Milk Powder Stored for Different Periods," Int'l Dairy Journal, 1997, vol. 7, pp. 119-127.
Food Standards Australia New Zealand, DHASCO and ARASCO Oils as Sources of Long Chain Polyunsaturated Fatty Acids in Infant Formula, Jun. 2003.
Friend et al., "Evaluation of Freeze-Drying Pasteurization, High-Temperature Heating and Storage on Selected Enzymes, B-Vitamins and Lipids of Mature Human Milk," J. Food Protect, vol. 46, No. 4, pp. 330-334, 1983.
Coassage et al., Carotenoid Composition of Human Milk During the First Month Postpartum and the Response to B-Carotene Supplementation, Am J Clin Nutr 2002, vol. 76, pp. 193-197.
Merritt et al., "Safety Evaluation of Sources of Docosahexaenoic Acid and Arachidonic Acid for Use in Infant Formulas n Newborn Piglets," Food and Chemical Toxicology 41 (2003), pp. 897-904.
Rudloff et al. "Protein and Nonprotein Nitrogen Components in Human Milk, Bovine Milk, and Infant Formula: Quantitative and Qualitative Aspects in Infant Nutrition," Journal of Pediatric Gastroenterology and Nutrition, Mar. 1997, vol. 24, Issue 3, pp. 328-344.
U.S. Appl. No. 61/428,866, filed Dec. 31, 2010 Buck et al.
Response to Office Action in U.S. Appl. No. 15/804,751 dated Aug. 19, 2019.
Applicant Initiated Interview Summary in U.S. Appl. No. 15/804,751 dated Aug. 27, 2019.
Response to Office Action in U.S. Appl. No. 15/866,322 dated Aug. 26, 2019.
Response to Office Action from U.S. Appl. No. 15/836,552 dated Aug. 26, 2019.
Response to Office Action from U.S. Appl. No. 15/892,169 dated Aug. 26, 2019.
Response to Office Action from U.S. Appl. No. 15/893,286 dated Aug. 26, 2019.
Notice of Opposition for EP Patent No. 2658546 B1 dated Sep. 11, 2019.
Substantive Examination Adverse Report in MY Application No. PI2013002513 dated Jul. 31, 2019.
Abbott Nutrition, "Pediatric Nutrition Product Guide," 2011, https://web.archive.org/web/20111120614153/http://abbottnutrition.com, 5 pages, downloaded Jul. 15, 2019.
Canfield, et al., "Multinational Study of Major Breast Milk Carotenoids of Healthy Mothers," European Journal of Nutrition, 42(3), pp. 133-141, 2003.
Deckelbaum et al., Infant Formula: Evaluating the Safety of New Ingredients, Washington D.C.,: The National Academies Press, Chapter 3, Comparing Infant Formulas with Human Milk, 2004, pp. Cover and 41-54.
Edge, et al., "The Carotenoids as anti-oxidants—a review," Journal of Photochemistry and Photobiology B: Biology, vol. 41(3), pp. 189-200.
Jewell et al., "A Comparison of Lutein and Zeaxanthin Concentrations in Formula and Human Milk Samples from Northern Ireland Mothers," European Journal of Clinical Nutrition, vol. 58, 2004, pp. 90-97.
Amendment in U.S. Appl. No. 15/019,496 dated Jan. 10, 2020.
Notice of Allowance in U.S. Appl. No. 15/019,496 dated Mar. 4, 2020.
Office Action in U.S. Appl. No. 15/804,751 dated Nov. 15, 2019.
Office Action from U.S. Appl. No. 15/844,294 dated Nov. 15, 2019.
Office Action from U.S. Appl. No. 15/866,322 dated Nov. 21, 2019.
Response to Office Action from U.S. Appl. No. 15/818,374 dated Nov. 5, 2019.
Office Action from U.S. Appl. No. 15/818,374 dated Nov. 21, 2019.
Response to Office Action from U.S. Appl. No. 15/893,112 dated Apr. 7, 2020.
Office Action from U.S. Appl. No. 15/836,552 dated Nov. 21, 2019.
Office Action from U.S. Appl. No. 15/892,169 dated Nov. 21, 2019.
Office Action from U.S. Appl. No. 15/892,234 dated Nov. 21, 2019.
Response to Office Action from U.S. Appl. No. 15/893,112 dated Oct. 4, 2019.
Office Action from U.S. Appl. No. 15/893,112 dated Jan. 7, 2020.
Office Action from U.S. Appl. No. 15/893,286 dated Nov. 21, 2019.
Response to Office Action from U.S. Appl. No. 15/707,477 dated Oct. 23, 2019.
Office Action from U.S. Appl. No. 15/707,477 dated Dec. 10, 2019.
Office Action from U.S. Appl. No. 16/531,849 dated Mar. 23, 2020.
Office Action from Canadian Application No. 2,822,495 dated Nov. 15, 2019.
Office Action from Canadian Application No. 2,822,664 dated Oct. 18, 2019.
Office Action in MX/a/2017/001953 dated Nov. 5, 2019 with English Summary.
Office Action in Vietnamese Application No. 1-2013-01947 dated Sep. 23, 2019.
Johnson, "The Role of Carotenoids in Human Health," Nutr Clin Care, Mar.-Apr. 2002; pp. 56-65 Abstract.
Mead Johnston Nutrition, "New Study Shows Infants Fed Formula with DHA and ARA Demonstrate Positive Long-Term Immune Outcomes", May 27, 2010 https://www.meadjohnson.com/news/press-releases/new-study-shows-infants-fed-formula-dha-and-ara-demonstrate-positive-long-term 2 page.
Yu, "The Role of Dietary Nucleotides in Neonatal and Infant Nutrition," Singapore Medical Journal, vol. 39 (4); 1998, pp. 145-150.
Response to Office Action in U.S. Appl. No. 15/804,751 dated Apr. 15, 2020.
Response to Office Action in U.S. Appl. No. 15/844,294 dated Apr. 15, 2020.
Office Action from U.S. Appl. No. 15/804,751 dated May 15, 2020.
Office Action from U.S. Appl. No. 15/844,294 dated May 14, 2020.
Office Action from U.S. Appl. No. 15/866,322 dated May 29, 2020.
Office Action from U.S. Appl. No. 15/836,552 dated May 29, 2020.
Office Action from U.S. Appl. No. 15/892,169 dated May 29, 2020.
Office Action from U.S. Appl. No. 15/892,234 dated May 29, 2020.
Notice of Allowance from U.S. Application No. 15/707,477 dated Jun. 11, 2020.
Office Action from Canadian Application No. 3,038,073 dated Jun. 1, 2020.
Communication pursuant to Article 101(1) and Rule 81 (2) to (3) EPC from EP Patent No. 2658546 B1 dated May 12, 2020.
Office Action from U.S. Appl. No. 15/893,286 dated May 29, 2020.
Response to Office Action in U.S. Appl. No. 15/866,322 dated Apr. 21, 2020.
Response to Office Action from U.S. Appl. No. 15/818,374 dated Apr. 21, 2020.
Response to Office Action from U.S. Appl. No. 15/836,552 dated Apr. 21, 2020.
Response to Office Action from U.S. Appl. No. 15/892,169 dated Apr. 21, 2020.
Interview Summary from U.S. Appl. No. 15/892,169 dated Apr. 22, 2020.
Response to Office Action from U.S. Appl. No. 15/892,234 dated Apr. 21, 2020.
Response to Office Action from U.S. Appl. No. 15/893,286 dated Apr. 21, 2020.
Response to Office Action from U.S. Appl. No. 15/707,477 dated Mar. 10, 2020.
Office Action from Chinese Application No. 201710680132.7 dated Mar. 25, 2020.
Search Report and Written Opinion from Singapore Application No. 10201606878Q dated Mar. 23, 2020.
Interview Summary from U.S. Appl. No. 16/531,849 dated Apr. 2, 2020.
Applicant Interview Summary from U.S. Appl. No. 15/844,294 dated Sep. 3, 2020.

(56) References Cited

OTHER PUBLICATIONS

Response to Office Action in U.S. Appl. No. 15/844,294 dated Sep. 14, 2020.
Office Action from U.S. Appl. No. 15/818,374 dated Jul. 7, 2020.
Response to Office Action from U.S. Appl. No. 15/836,552 dated Aug. 31, 2020.
Response to Office Action in U.S. Appl. No. 15/866,322 dated Aug. 31, 2020.
Response to Office Action from U.S. Appl. No. 15/892,234 dated Aug. 31, 2020.
Office Action from U.S. Appl. No. 15/893,112 dated Jun. 26, 2020.
Response to Office Action from U.S. Appl. No. 15/892,169 dated Aug. 31, 2020.
Response to Office Action from U.S. Appl. No. 16/531,849 dated Jul. 23, 2020.
Office Action from U.S. Appl. No. 16/531,849 dated Sep. 2, 2020.
Office Action from Chinese Application No. 201811294626.2 dated Jun. 22, 2020.
Communication for EP Application No. 11811267.1 dated Jul. 10, 2020.
Office Action in MX/a/2018/002900 received by associate on Jul. 14, 2020 with English Summary.
Substantive Examination Adverse Report in Malaysian Application No. PI 2017001831 dated Jul. 6, 2020.
Aderem et al., "Toll-Like Receptors in the Induction of the Innate Immune Response," Nature, vol. 406, Aug. 2000, p. 782.
Bautista et al., "IL-8 Regulates Mucin Gene Expression at the Posttranscriptional Level in Lung Epithelial Cells," J Immunol 2009; 183, pp. 2159-2166.
Modulate, Dictionary Definition, 1 page.
Mukaida, "Pathophysiological roles of interieukin-8/CXCLS 1n pulmonary diseases," Am J Physiol Lung Cell Mol Physiol 284 pp: L566-L577, 2003.
Muselet-Charlier et al., Enhanced IL-1Beta-induced IL-8 production in cystic fibrosis lung epithelial cells is dependent of both mitogen-activated protein kinases and NF-Kb signaling, Biochemical and Biophysical Research Communications 357 (2007) pp. 402-407.
Schneider et al., "Increased Cytokine Response of Rhinovirus-infected Airway Epithelial Cells in Chronic Obstructive Pulmonary Disease," Am J Respir Crit Care Med., vol. 182, pp. 333-340, 2010.
Sumiyoshi, et al., "Sialyl Oligosaccharides in the Milk of Japanese Women Changes in Concentration during the Course of Lactation," J. A.pp. Glyoci, 50, pp. 461-467.
Van Deventer, "Review article: Chemokine production by intestinal epithelial cells: a therapeutic target in inflammatory bowel disease?" AllmentPharmacolTher 1997:11 (Suppl 3): pp. 116-121.
Yu et al., "Intestinal Epithelial Cell Regulation of Mucosal Inflammation," Immunologic Research 2004, pp. 55-67.
Zorn et al., "Vertebrate Endoderm Development and Organ Formation" Annu Rev Cell Dev Biol 2009 ; 25, pp. 221-251.
Response to Office Action from U.S. Appl. No. 15/893,286 dated Aug. 31, 2020.
Response to Office Action in U.S. Appl. No. 15/804,751 dated Sep. 15, 2020.
Singhal et al., "Dietary Nucleotides and Fecal Microbiota in Formula-Fed Infants; a Randomized Controlled Trial," American Journal Clin Nutr, 2008; 87, pp. 1785-1792.
Office Action in U.S. Appl. No. 15/804,751 dated Dec. 9, 2020.
Office Action In U.S. Appl. No. 15/866,322 dated Dec. 8, 2020.
Response to Office Action from U.S. Appl. No. 15/818,374 dated Nov. 9, 2020.
Miscellaneous Communication from U.S. Appl. No. 15/818,374 dated Nov. 10, 2020.
Office Action from U.S. Appl. No. 15/818,374 dated Dec. 16, 2020.
Office Action from U.S. Appl. No. 15/836,552 dated Dec. 3, 2020.
Office Action from U.S. Appl. No. 15/892,169 dated Dec. 16, 2020.
Office Action from U.S. Appl. No. 15/892,234 dated Dec. 16, 2020.
Response to Office Action from U.S. Appl. No. 15/893,112 dated Sep. 28, 2020.
Response to Office Action from U.S. Appl. No. 16/531,849 dated Dec. 2, 2020.
Notice of Allowance from U.S. Appl. No. 16/531,849 dated Dec. 14, 2020.
Office Action from Canadian Application No. 2,822,664 dated Nov. 18, 2020.
Second Office Action in CN 201710680132.7 dated Oct. 12, 2020.
Summons to Attend Oral Proceedings for EP Application No. 11809048.9 dated Oct. 5, 2020.
Search Report from EP Application No. 20186779.3 dated Nov. 27, 2020.
Office Action from U.S. Appl. No. 15/844,294 dated Dec. 24, 2020.
Response to Office Action from U.S. Appl. No. 15/892,234 dated Apr. 16, 2021.
Office Action from U.S. Appl. No. 15/893,112 dated Dec. 28, 2020.
Response to Office Action from U.S. Appl. No. 15/893,112 dated Mar. 29, 2021.
Office Action from U.S. Appl. No. 15/893,112 dated May 12, 2021.
Office Action from U.S. Appl. No. 15/893,286 dated Dec. 23, 2020.
Response to Office Action from U.S. Appl. No. 15/893,286 dated Apr. 23, 2021.
Office Action from Chinese Application No. 201811294626.2 dated Feb. 19, 2021.
Office Action from Chinese Application No. 201810264161.X dated Dec. 9, 2020.
Summons to Attend Oral Proceedings for EP Application No. 11810764.8 dated Jan. 12, 2021.
Communication Pursuant to Article 94(3) EPC from European Application No. 18210271.5 dated Oct. 26, 2020.
Office Action in MX/a/2018/002900 dated Jan. 8, 2021 with English Summary.
Non-Final Office Action in U.S. Appl. No. 14/195,938 dated Jan. 26, 2017.
Decision on Rejection in CN 201180068364.8 dated Oct. 17, 2016.
Notice of Reexamination in CN 201180068365.2 dated Feb. 3, 2017.
Decision on Rejection in CN 201180068714.0 dated Jan. 13, 2017.
Decision on Rejection in CN 201180068711.7 dated Apr. 7, 2017.
Communication for EP Application No. 11810764.8 dated Aug. 2, 2017.
Examination Report in ID Application No. W00201302964 dated Jan. 21, 2017.
Office Action in MX/a/2013/007676 dated Feb. 7, 2017.
Office Action in MX/a/2013/007676 dated Jul. 28, 2017.
Office Action in MX/a/2013/007679 dated May 23, 2017.
Office Action in MX/a/2013/007684 dated Dec. 6, 2016.
Office Action in MX/a/2013/007684 dated Jun. 13, 2017.
Office Action in MX/a/2013/007706 dated Dec. 13, 2016.
Office Action in MX/a/2013/007706 dated Mar. 21, 2017.
Office Action in MX/a/2013/007706 dated Jun. 20, 2017.
Substantive Examination Adverse Report in MY Application No. PI2013002505 dated Jan. 13, 2017.
Substantive Examination Adverse Report in MY Application No. PI2013002505 dated Aug. 15, 2017.
Substantive Examination Adverse Report in MY Application No. PI2013002470 dated Dec. 30, 2016.
Substantive Examination Adverse Report in MY Application No. PI2013002506 dated Jan. 13, 2017.
Substantive Examination Report in PH Application No. 1-2013-501361 dated Mar. 10, 2017.
Substantive Examination Report in PH Application No. 1-2013-501415 dated Mar. 10, 2017.
Substantive Examination Report in PH Application No. 1-2013-501388 dated Mar. 15, 2017.
Brunser et al. "Effect of dietary nucleotide supplementation on diarrhoeal disease in infants," Acta Pediatrica, vol. 83, No. 2, 1994, pp. 188-191.
Office Action in U.S. Appl. No. 15/019,496 dated Oct. 17, 2017.
Reexamination Notice in CN 201180068364.8 dated Aug. 31, 2017.
Office Action in MX/a/2013/007684 dated Oct. 17, 2017.
Office Action in MX/a/2013/007706 dated Oct. 10, 2017.
Completion of Final Requirements in PH Application No. 1-2013-501388 dated Aug. 11, 2017.

(56) References Cited

OTHER PUBLICATIONS

U.S. Appl. No. 61/428,860, filed Dec. 31, 2010 Buck et al.
Notice of Allowance from U.S. Appl. No. 15/893,286 dated Jul. 21, 2021.
Notice of Opposition for EP Patent No. 3338784 dated Apr. 22, 2021.
Notice of Opposition for EP Patent No. 3338784 dated Apr. 30, 2021.
Notice of Further Opposition for EP Patent No. 3338784 dated May 6, 2021.
Gil, Angel et al. "Interaction of early diet and the development of the immune system", Nutrition Research Reviews, 2002 pp. 263-292.
Ruan et al. Suppressive effect of locally produced interleukin-IO on respiratory syncytial virus infection, Immunology 2001, 104, pp. 355-360.
Idanpaan-Heikkila , I. et al., "Oligosaccharides Interfere with the Establishment and Progression of Experimental Pneumococcal Pneumonia" The Journal of Infectious Diseases, vol. 176, 1997, pp. 704-712.
Kunz et al. "Sialyllactose suppress TNF-a stimulated IL-8 secretion in vitro" Published Online Apr. 1, 2009, 1 page.
Prieto, Foods Food Ingredients J. Jpn 2005 210(11): pp. 1018-1030,, No. 11, 2005.
Response to Office Action in U.S. Appl. No. 15/844,294 dated May 24, 2021.
Office Action from U.S. Appl. No. 15/844,294 dated Jul. 14, 2021.
Response to Office Action from U.S. Appl. No. 15/818,374 dated May 17, 2021.
Office Action from U.S. Appl. No. 15/818,374 dated Jul. 7, 2021.
Office Action from U.S. Appl. No. 15/892,234 dated Jul. 8, 2021.
Decision of Rejection in CN 201710680132.7 dated Mar. 1, 2021.
English Translation of Office Action from Chinese Application No. 201811294626.2 dated Jul. 23, 2021.
English Translation of Office Action from Chinese Application No. 201910150810.8 dated Jul. 9, 2021.
Communication Pursuant to Article 94(3) EPC from European Application No. 20186779.3 dated Aug. 12, 2021.

\* cited by examiner

FIG. 1

Effect of various HMOs on H1N1 influenza Virus infectivity on MDCK cells (canine kidney)

Legend: 10mg/ml, 1mg/ml, 0.1mg/ml, 0.01mg/ml

Y-axis: FFU (0–60)
X-axis: 2-FL, 3-FL, 3-SL, 6-SL, LNT, SA Positive control

Infectious virus control = ~52-55 FFU

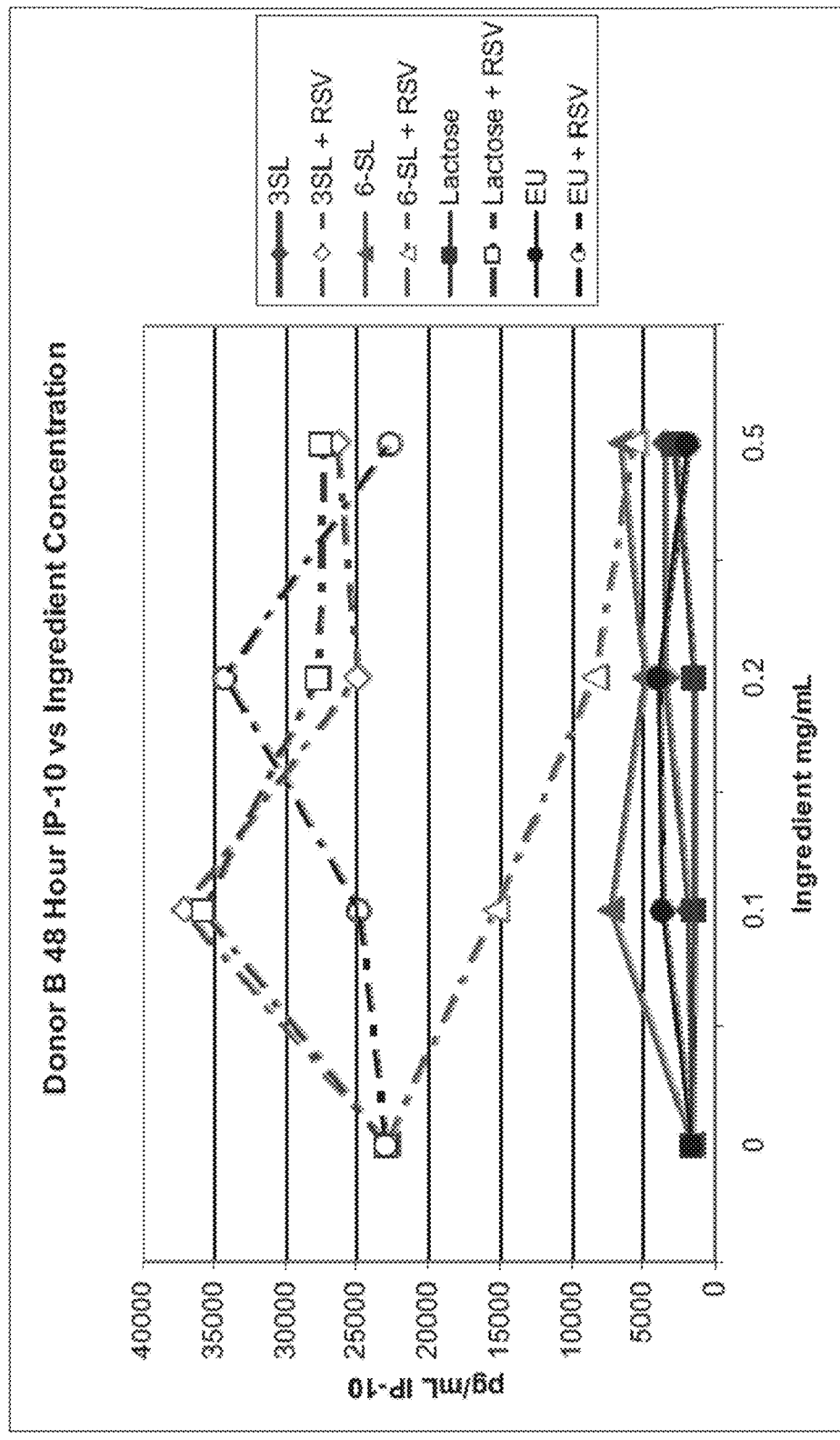

METHODS OF USING HUMAN MILK OLIGOSACCHARIDES FOR IMPROVING AIRWAY RESPIRATORY HEALTH

CROSS REFERENCE TO RELATED APPLICATIONS

This application is a continuation of U.S. patent application Ser. No. 13/335,433, filed on Dec. 22, 2011, which claims the benefit of U.S. Provisional Application No. 61/428,860 filed on Dec. 31, 2010; and U.S. Provisional Application No. 61/527,851 filed on Aug. 26, 2011, which disclosures are incorporated by reference in their entirety.

FIELD OF THE DISCLOSURE

The present disclosure relates to human milk oligosaccharides (HMOs) for improving airway respiratory health in an infant, toddler, or child. More particularly, the present disclosure relates to human milk fortifiers, preterm and term infant formulas and pediatric formulas comprising HMOs that can reduce inflammation and thereby improve airway defense mechanisms and overall airway respiratory health in an infant, toddler or child.

BACKGROUND OF THE DISCLOSURE

The inflammatory response is an attempt by the body to restore and maintain homeostasis after invasion by an infectious agent, antigen challenge, or physical, chemical or traumatic damage. While the inflammatory response is generally considered a healthy response to injury, the immune system can present an undesirable physiological response if it is not appropriately regulated. Specifically, unregulated oxidation and associated inflammation are major causes of tissue damage and clinically significant disease in preterm and term infants. This is due in large part to the immaturity in function of the natural immune system of infants, and especially preterm infants.

Breastfeeding has been associated with enhanced development and balanced growth and maturation of the infant's respiratory, gastrointestinal and immune systems, thereby providing protection of the infant to infection and inflammatory diseases. Breast milk appears to contain endogenous antioxidants, such as superoxide dismutase, glutathione peroxidase and catalase, or other non-enzymatic antioxidants such as glutathione, lactoferrin and polyphenols, in addition to exogenous antioxidants, such as vitamins A, C, E and selenium. Further, breast milk includes HMOs that not only act as pathogen receptor analogues, but activate immune factors by infant intestinal epithelial cells and/or associated immune cell populations. The function of these breast milk components, functioning as antioxidants and as immune modulators, includes not only the protection of breast milk lipids by peroxidation, but may also assist in the regulation of inflammatory responses to infection or other injury.

Not all infants receive human breast milk. Further, no vaccines are currently available for the prevention of inflammatory diseases. Therefore, development of safe and efficacious preventative or therapeutic methods would be beneficial, especially for infants.

It would therefore be desirable to provide nutritional compositions, and synthetic infant formulas in particular, that can produce nutritional benefits including improved immune system growth and development, improved airway defense mechanisms, and improved overall airway respiratory health. It would additionally be beneficial if the nutritional compositions could modulate inflammation and enhance immunity against microbial infections, including bacterial and viral infections, and other inflammatory diseases.

SUMMARY OF THE DISCLOSURE

The present disclosure is directed to nutritional compositions, including synthetic infant formulas, synthetic pediatric formulas, and synthetic child formulas, including at least one HMO, alone or in combination with one or more of long chain polyunsaturated fatty acids (LCPUFAs), antioxidants, and/or nucleotides, for improving airway respirator health and/or airway defense mechanisms in an infant, toddler, or child, as well as methods of using the compositions.

One embodiment is a method of improving airway respiratory health in an infant, toddler, or child. The method includes identifying an infant, toddler, or child in need of improved respiratory health and administering to the infant, toddler, or child a composition comprising a human milk oligosaccharide selected from the group consisting of 3'-sialyllactose, 6'-sialyllactose, 2'-fucosyllactose, and lacto-N-neotetraose in a concentration of from about 0.001 mg/mL to about 0.2 mg/mL and a carotenoid.

Another embodiment is a method of improving airway defense mechanisms in an infant, toddler, or child. The method includes identifying an infant, toddler, or child in need of improved airway defense mechanisms and administering to the infant, toddler, or child a composition comprising a human milk oligosaccharide selected from the group consisting of 3'-sialyllactose, 6'-sialyllactose, 2'-fucosyllactose, and lacto-N-neotetraose in a concentration of from about 0.001 mg/mL to about 0.2 mg/mL and a carotenoid.

It has been discovered that specific HMOs, such as 3'-sialyllactose, 6'-sialyllactose and others as noted herein, are highly effective in dampening inflammation generally in infants, toddlers, and children, and specifically in dampening virus-induced inflammation, including respiratory syncytial virus, human parainfluenza, and influenza A, in infants, toddlers, and children by reducing the production of some key cytokines from human immune cells without increasing viral load, which may lead to faster recovery from infections. Surprisingly, it was determined that the HMOs demonstrate the desirable dampening effects even at very low concentrations, including concentrations lower than those found in breast milk. Also, it was unexpectedly found that 6'-sialyllactose is immunomodulatory even in the absence of a virus, and induces the production of monocyte-derived cytokines. It has further been discovered that although biological reactions often occur within a 30 to 60 minute period, and thus a 30 to 60 minute incubation is generally used for in vitro procedures, a 24 hour pre-treatment of cells provides a closer reflection of the daily pre-exposure to HMOs that a breast-fed infant would receive from breast milk.

Additionally, it has been found that fucosylated HMOs, including 3'-fucosyllactose, alone or in combination with sialic acid, are highly effective in inhibiting respiratory viruses. Even at low concentrations, the 3'-fucosyllactose and sialic acid are effective.

Moreover, it has been discovered that specific HMOs act in a synergistic manner against respiratory viruses, including RSV, when combined with a long chain polyunsaturated fatty acid and/or a carotenoid. These synergistic actions dampen virus-induced inflammatory cytokines, and specifically interferon-inducible protein 10 (IP-10). Additional components including antioxidants, such as vitamin A and vitamin E, or nucleotides, may also be added to the HMO and long chain polyunsaturated fatty acid and/or carotenoid combinations.

It has further been found that a combination of HMOs including acidic/sialylated (e.g., 6'-sialyllactose) and/or neutral/fucosylated (e.g., 2'-fucosyllactose) and/or n-acetylglucosylated (e.g., LNnT) prevents the development of necrotizing entercolitis. Also, these HMOs have been found to decrease the oxidative stress in infants.

BRIEF DESCRIPTION OF THE DRAWINGS

FIG. 1 is a graph depicting H1N1 virus infectivity of MDCK cells in the presence of various HMOs as tested in Example 37.

FIG. 3 is a graph depicting IP-10 levels resulting from administration of 3'SL and 6'SL as measured in Example 39.

DETAILED DESCRIPTION OF THE DISCLOSURE

Figure 2:
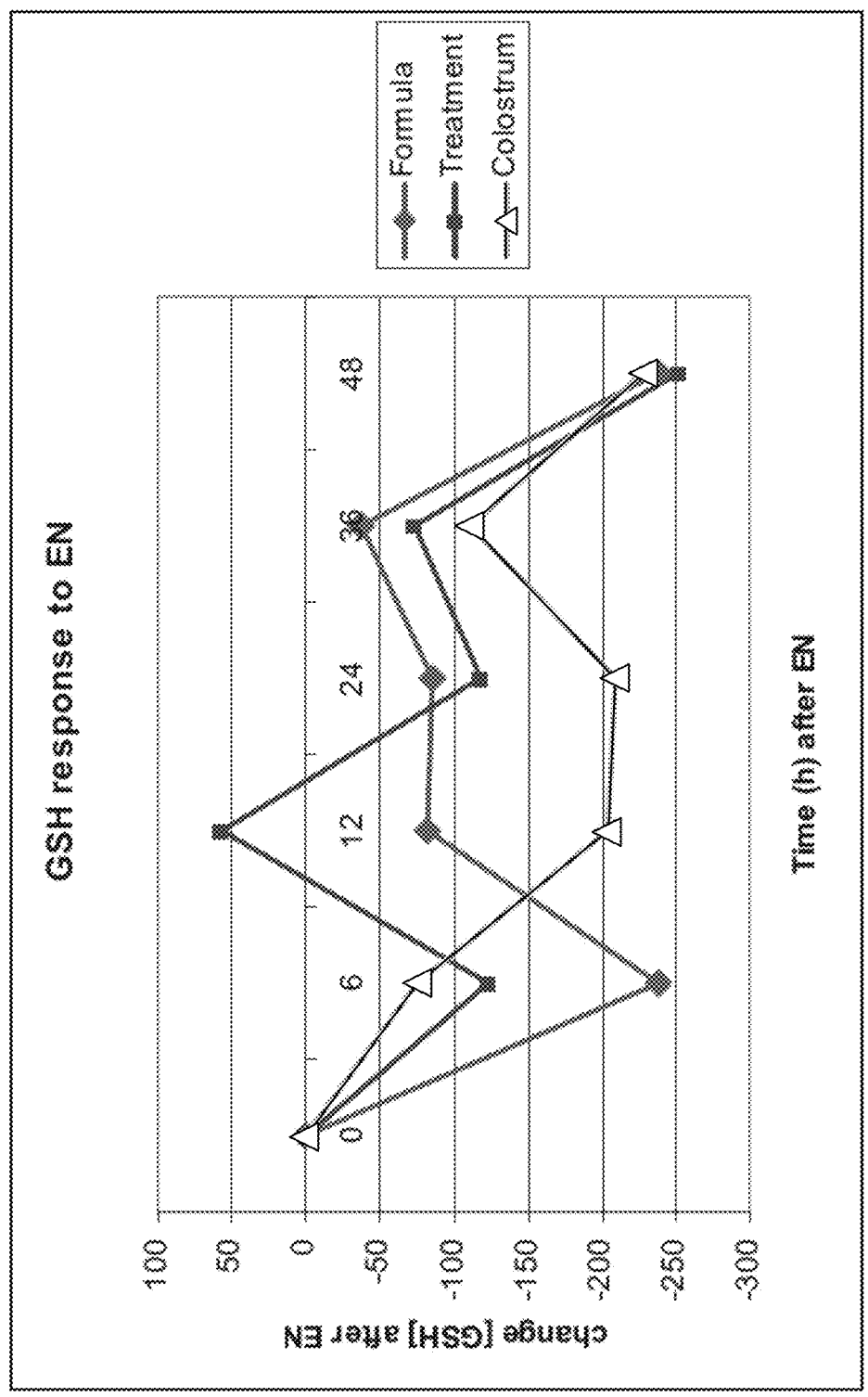
FIG. 2 is a graph depicting blood plasma levels of glutathione from piglets as measured in Example 38.

The nutritional compositions and methods described herein utilize HMOs alone or in combination with long chain polyunsaturated fatty acids, and/or antioxidants, and in particular carotenoids, and/or nucleotides for controlling and reducing a number of diseases and conditions related to inflammation. The nutritional compositions are particularly effective in improving airway respiratory health and airway defense mechanisms. These and other features of the nutritional compositions and methods, as well as some of the many optional variations and additions, are described in detail hereafter.

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", as used herein, unless otherwise specified, refers generally to a number of complex carbohydrates found in human breast milk that can be in acidic or neutral form, and to precursors thereof. Exemplary non-limiting human milk oligosaccharides include 3'-sialyllactose, 6'-sialyllactose, 3'-fucosyllactose, 2'-fucosyllactose, and lacto-N-neo-tetraose. Exemplary human milk oligosaccharide precursors includes sialic acid and/or fucose.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional solids, nutritional semi-solids, nutritional semi-liquids, nutritional powders, nutritional supplements, and any other nutritional food product as known in the art. The nutritional powders may be reconstituted to form a nutritional liquid, all of which comprise one or more of fat, protein and carbohydrate and are suitable for oral consumption by a human. The terms "nutritional formulation" or "nutritional composition" do not include human breast milk.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spraydried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "infant" as used herein, unless otherwise specified, refers to a person 12 months or younger. The term "preterm infant" as used herein, refers to a person born prior to 36 weeks of gestation.

The term "toddler" as used herein, unless otherwise specified, refers to a person greater than one year of age up to three years of age.

The term "child" as used herein, unless otherwise specified, refers to a person greater than three years of age up to twelve years of age.

The term "newborn" as used herein, unless otherwise specified, refers to a person from birth up to four weeks of age.

The terms "infant formula" or "synthetic infant formula" as used herein, unless otherwise specified, are used interchangeably and refer to liquid, solid, semi-solid, and semi-liquid human milk replacements or substitutes that are suitable for consumption by an infant. The synthetic formulas include components that are of semi-purified or purified origin. As used herein, unless otherwise specified, the terms "semi-purified" or "purified" refer to a material that has been prepared by purification of a natural material or by synthesis. The terms "infant formula" or "synthetic infant formula" do not include human breast milk.

The term "synthetic pediatric formula" as used herein, unless otherwise specified, refers to liquid, solid, semi-liquid, and semi-solid human milk replacements or substitutes that are suitable for consumption by an infant or toddler up to the age of 36 months (3 years). The synthetic formulas include components that are of semi-purified or purified origin. As used herein, unless otherwise specified, the terms "semi-purified" or "purified" refer to a material that has been prepared by purification of a natural material or by synthesis. The term "synthetic pediatric nutritional formula" does not include human breast milk.

The term "synthetic child formula" as used herein, unless otherwise specified, refers to liquid, solid, semi-solid, and semi-liquid human milk replacements or substitutes that are suitable for consumption by a child up to the age of 12 years. The synthetic formulas include components that are of semi-purified or purified origin. As used herein, unless otherwise specified, the terms "semi-purified" or "purified" refer to a material that has been prepared by purification of a natural material or by synthesis. The term "synthetic child nutritional formula" does not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

The terms "absence of a virus" or "absent a virus" as used herein with respect to inducing production of monocyte-derived cytokines, unless otherwise specified, refer to an individual (e.g., an infant) without the virus or having the virus in an amount less than the amount required to illicit an immune response; that is, an amount that is less than required for the body's natural immune response to increase the production of cytokines and other immune factors.

The terms "inflammatory disease" or "inflammatory condition" as used herein, unless otherwise specified, refer to any disease, disorder, or condition characterized by inflammation. The term "infection-mediated inflammatory disease" as used herein, unless otherwise specified, refers to an inflammatory disease associated or induced by microbial infection, including viral and bacterial infection.

The terms "susceptible" and "at risk" as used herein, unless otherwise specified, mean having little resistance to a certain condition or disease, including being genetically predisposed, having a family history of, and/or having symptoms of the condition or disease.

The terms "modulating" or "modulation" or "modulate" as used herein, unless otherwise specified, refer to the targeted movement of a selected characteristic.

The terms "growth of a virus" or "growth of bacteria" as used herein, unless otherwise specified, refer to the production, proliferation, or replication of a virus or bacteria.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional compositions and methods may comprise, consist of, or consist essentially of the essential elements of the compositions and methods as described herein, as well as any additional or optional element described herein or otherwise useful in nutritional product applications.

Product Form

The nutritional compositions of the present disclosure may be formulated and administered in any known or otherwise suitable oral product form. Any solid, liquid, semi-solid, semi-liquid or powder product form, including combinations or variations thereof, are suitable for use herein, provided that such forms allow for safe and effective oral delivery to the individual of the essential ingredients as also defined herein.

The nutritional compositions of the present disclosure include one or more HMOs as described herein. The compositions may include one or more HMOs alone or in combination with other immune enhancing factors including, but not limited, to long chain polyunsaturated acids (LCPUFAs), nucleotides, and antioxidants, such as carotenoids and vitamins, as discussed below.

The nutritional compositions may be in any product form comprising the ingredients described herein, and which is safe and effective for oral administration. The nutritional compositions may be formulated to include only the ingredients described herein, or may be modified with optional ingredients to form a number of different product forms.

The nutritional compositions of the present disclosure are desirably formulated as dietary product forms, which are defined herein as those embodiments comprising the ingredients of the present disclosure in a product form that then contains at least one of fat, protein, and carbohydrate, and preferably also contains vitamins, minerals, or combinations thereof. The nutritional compositions will comprise at least HMOs, desirably in combination with at least one of protein, fat, vitamins, and minerals, to produce a nutritional composition.

The nutritional compositions may be formulated with sufficient kinds and amounts of nutrients to provide a sole, primary, or supplemental source of nutrition, or to provide a specialized nutritional product for use in individuals afflicted with specific diseases or conditions or with a targeted nutritional benefit as described below.

Specific non-limiting examples of product forms suitable for use with the HMO-containing compositions as disclosed herein include, for example, liquid and powdered dietary supplements, liquid and powdered human milk fortifiers, liquid and powdered preterm infant formulas, liquid and powdered infant formulas, liquid and powdered elemental and semi-elemental formulas, liquid and powdered pediatric formulas, liquid and powdered toddler formulas, and liquid and powdered follow-on formulas suitable for use with infants and children.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 85%, of water by weight of the nutritional emulsions. The nutritional emulsions may have a variety of product densities, but most typically have a density greater than about 1.03 g/mL, including greater than about 1.04 g/mL, including greater than about 1.055 g/mL, including from about 1.06 g/ml to about 1.12 g/mL, and also including from about 1.085 g/ml to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least about 1 mL, or even at least about 2 mL, or even at least about 5 mL, or even at least about 10 mL, or even at least about 25 mL, including ranges from about 1 mL to about 300 mL, including from about 4 mL to about 250 mL, and including from about 10 mL to about 240 mL.

Nutritional Solids

The nutritional solids may be in any solid form but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

Human Milk Oligosaccharides (HMOs)

The nutritional compositions of the present disclosure include at least one HMO, and in many embodiments, a combination of two or more HMOs. Oligosaccharides are one of the main components of human breast milk, which contains, on average, 10 grams per liter of neutral oligosaccharides and 1 gram per liter of acidic oligosaccharides. The composition of human milk oligosaccharides is very complex and more than 200 different oligosaccharide-like structures are known.

The HMOs may be included in the nutritional compositions alone, or in some embodiments, in combination with other immune enhancing factors (e.g., LCPUFAs, antioxidants, nucleotides, etc.) as described herein. The HMO or HMOs may be isolated or enriched from milk(s) secreted by mammals including, but not limited to: human, bovine, ovine, porcine, or caprine species. The HMOs may also be produced via microbial fermentation, enzymatic processes, chemical synthesis, or combinations thereof.

Suitable HMOs for use in the nutritional compositions may include acidic oligosaccharides, neutral oligosaccharides, n-acetylglucosylated oligosaccharides, and HMO precursors. Specific non-limiting examples of HMOs that may be included individually or in combination in the compositions of the present disclosure include: sialic acid (i.e., free sialic acid, lipid-bound sialic acid, protein-bound sialic acid); D-glucose (Glc); D-galactose (Gal); N-acetylglucosamine (GlcNAc); L-fucose (Fuc); fucosyl oligosaccharides (i.e., Lacto-N-fucopentaose I; Lacto-N-fucopentaose II; 2'-Fucosyllactose; 3'-Fucosyllactose; Lacto-N-fucopentaose III; Lacto-N-difucohexaose I; and Lactodifucotetraose); non-fucosylated, non-sialylated oligosaccharides (i.e., Lacto-N-tetraose and Lacto-N-neotetraose); sialyl oligosaccharides (i.e., 3'-Sialyl-3-fucosyllactose; Disialomonofucosyllacto-N-neohexaose; Monofucosylmonosialyl-lacto-N-octaose (sialyl Lea); Sialyllacto-N-fucohexaose II; Disialyllacto-N-fucopentaose II; Monofucosyldisialyllacto-N-tetraose); and sialyl fucosyl oligosaccharides (i.e., 2'-Sialyllactose; 2-Sialyllactosamine; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyllacto-N-neohexaose II; Disialyllacto-N-neohexaose; Disialyllacto-N-tetraose; Disialyllacto-N-hexaose II; Sialyllacto-N-tetraose a; Disialyllacto-N-hexaose I; and Sialyllacto-N-tetraose b). Also useful are variants in which the glucose (Glc at the reducing end is replaced by N-acetylglucosamine (e.g., 2'-fucosyl-N-acetylglucosamine (2'-FLNac) is such a variant to 2'-fucosyllactose). These HMOs are described more fully in U.S. Patent Application No. 2009/0098240, which is herein incorporated by reference in its entirety. Other suitable examples of HMOs that may be included in the compositions of the present disclosure include lacto-N-fucopentaose V, lacto-N-hexaose, para-lacto-N-hexaose, lacto-N-neohexaose, para-lacto-N-neohexaose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaose, lacto-N-neoocataose, para-lacto-N-octanose, iso-lacto-N-octaose, lacto-N-octaose, monofucosyllacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-decaose, trifucosyllacto-N-neooctaose, trifucosyllacto-N-octaose, trifucosyl-iso-lacto-N-octaose, lacto-N-difuco-hexaose II, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, and disialyl-lacto-N-tetraose, and combinations thereof. Particularly suitable nutritional compositions include at least one of the following HMOs or HMO precursors: sialic acid (SA); 3'-Sialyllactose (3'SL); 6'-Sialyllactose (6'SL); 2'-Fucosyllactose (2'FL); 3'-Fucosyllactose (3'FL); Lacto-N-tetraose and Lacto-N-neotetraose (LNnT), and in particular, combinations of 6'SL and 3'SL; combinations of 3'FL and SA; combinations of 2'FL and 3'FL; combinations of 2'FL, 3'SL, and 6'SL; combinations of 3'SL, 3'FL, and LNnT; and combinations of 6'SL, 2'FL, and LNnT.

Other exemplary combinations include: SA, 3'SL, 6'SL, 3'FL, 2'FL, and LNnT; 3'SL, 6'SL, 3'FL, 2'FL, and LNnT; SA, 6'SL, 3'FL, 2'FL, and LNnT; SA, 3'SL, 3'FL, 2'FL, and LNnT; SA, 3'SL, 6'SL, 2'FL, and LNnT; SA, 3'SL, 6'SL, 3'FL, and LNnT; SA, 3'SL, 6'SL, 3'FL, and 2'FL; SA and 3'SL; SA and 6'SL; SA and 2'FL; SA and LNnT; SA, 3'SL, and 6'SL; SA, 3'SL and 3'FL; SA, 3'SL and 2'FL; SA, 3'SL and LNnT; SA, 6'SL and 3'FL; SA, 6'SL, and 2'FL; SA, 6'SL, and LNnT; SA, 3'FL, and 2'FL; SA, 3'FL, and LNnT; SA, 2'FL, and LNnT; SA, 3'SL, 6'SL, and 3'FL; SA, 3'SL, 6'SL and 2'FL; SA, 3'SL, 6'SL, and LNnT; SA, 3'SL, 3'FL, and 2'FL; SA, 3'SL, 3'FL, and LNnT; SA, 3'SL, 2'FL, and LNnT; SA, 6'SL, 3'FL, and 2'FL; SA, 6'SL, 2'FL, and LNnT; SA, 6'SL, 3'FL, and LNnT; SA, 3'FL, 2'FL, and LNnT; SA, 6'SL, 2'FL, and LNnT; SA, 3'FL, 2'FL, and LNnT; SA, 6'SL, 3'FL, 2'FL, and LNnT; SA, 3'SL, 6'SL, 3'FL, and LNnT; SA, 3'SL, 3'FL, 2'FL, and LNnT; SA, 3'SL, 6'SL, 2'FL, and LNnT; 3'SL, 6'SL, 3'FL, and 2'FL; 3'SL, 6'SL, 2'FL, and LNnT; 3'SL, 3'FL, 2'FL, and LNnT; 3'SL, 6'SL, 3'FL, and LNnT; 3'SL, 6'SL, and 3'FL; 3'SL, 3'FL, and 2'FL; 3'SL, 2'FL, and LNnT; 3'SL, 6'SL, and 2'FL; 3'SL, 6'SL, and LNnT; 3'SL and 3'FL; 3'SL and 2'FL; 3'SL and LNnT; 6'SL and 3'FL; 6'SL and 2'FL; 6'SL and LNnT; 6'SL, 3'FL, and LNnT; 6'SL, 3'FL, 2'FL, and LNnT; 3'FL, 2'FL, and LNnT; 3'FL and LNnT; and 2'FL and LNnT.

The HMOs are present in the nutritional compositions in total amounts of HMO in the composition (mg of HMO per mL of composition) of at least about 0.001 mg/mL, including at least about 0.01 mg/mL, including from about 0.001 mg/mL to about 20 mg/mL, including from about 0.01 mg/mL to about 20 mg/mL, including from about 0.01 mg/mL to about 10 mg/mL, including from about 0.01 mg/mL to about 5 mg/mL, including from about 0.001 mg/mL to about 1 mg/mL, including from about 0.001 mg/mL to about 0.23 mg/mL, including from about 0.01 mg/mL to about 0.23 mg/mL of total HMO in the nutritional composition. Typically, the amount of HMO in the nutritional composition will depend on the specific HMO or HMOs present and the amounts of other components in the nutritional compositions.

In one specific embodiment when the nutritional product is a nutritional powder, the total concentration of HMOs in the nutritional powder is from about 0.0005% to about 5%, including from about 0.01% to about 1% (by weight of the nutritional powder).

In another specific embodiment, when the nutritional product is a ready-to-feed nutritional liquid, the total concentration of HMOs in the ready-to-feed nutritional liquid is from about 0.0001% to about 0.50%, including from about 0.001% to about 0.15%, including from about 0.01% to about 0.10%, and further including from about 0.01% to about 0.03% (by weight of the ready-to-feed nutritional liquid).

In another specific embodiment when the nutritional product is a concentrated nutritional liquid, the total concentration of HMOs in the concentrated nutritional liquid is from about 0.0002% to about 0.60%, including from about 0.002% to about 0.30%, including from about 0.02% to about 0.20%, and further including from about 0.02% to about 0.06% (by weight of the concentrated nutritional liquid).

In one specific embodiment, the nutritional composition includes a neutral human milk oligosaccharide in an amount of from about 0.001 mg/mL to about 20 mg/mL, including from 0.01 mg/mL to about 20 mg/mL, including from about 0.001 mg/mL to less than 2 mg/mL, and including from about 0.01 mg/mL to less than 2 mg/mL.

In some embodiments, the HMOs are used in combination to provide the desired immune enhancing effect. For example, in one embodiment, the nutritional composition includes 6'SL in combination with 3'SL in a total amount of HMO of from about 0.001 mg/mL to about 20 mg/mL, including from about 0.01 mg/mL to about 20 mg/mL, including from about 0.001 mg/mL to less than 0.23 mg/mL, including from about 0.01 mg/mL to less than 0.23 mg/mL, including from about 0.001 mg/mL to less than 0.15 mg/mL, and including from 0.01 mg/mL to less than 0.15 mg/mL of the nutritional composition. In another embodiment, the nutritional composition includes 6'SL in combination with 3'SL in a total amount of HMO of from about 0.001 mg/mL to about 20 mg/mL, including from about 0.01 mg/mL to about 20 mg/mL and including greater than 0.65 mg/mL to about 20 mg/mL. In another embodiment, the nutritional composition includes 3'SL and 6'SL in a weight ratio of from about 1:20 to about 20:1, including from about 1:10 to about 10:1, and including from about 1:2 to about 2:1.

In one specific embodiment, the nutritional composition includes 6'SL, alone or in combination with other HMOs, in an amount of from about 0.001 mg/mL to about 20 mg/mL, including from about 0.01 mg/mL to about 20 mg/mL, including from about 0.001 mg/mL to less than 0.25 mg/mL, including from about 0.01 mg/mL to less than 0.25 mg/mL, including from greater than 0.4 mg/mL to about 20 mg/mL, and including from about 0.1 mg/mL to about 0.5 mg/mL.

In one embodiment, when the nutritional composition includes 6'SL, the total amount of HMOs in the nutritional composition includes at least about 88% (by total weight HMOs) 6'SL, including from about 88% (by total weight HMOs) to about 96% (by total weight HMOs), including from about 88% (by total weight HMOs) to about 100% (by total weight HMOs), and including about 100% (by total weight HMOs) 6'SL.

In another embodiment, the nutritional composition includes 3'SL, alone or in combination with other HMOs, in an amount of from about 0.001 mg/mL to about 20 mg/mL, including from about 0.01 mg/mL to about 20 mg/mL, including from about 0.001 mg/mL to less than 0.15 mg/mL, including from about 0.01 mg/mL to less than 0.15 mg/mL, and including from greater than 0.25 mg/mL to about 20 mg/mL.

In one embodiment, when the nutritional composition includes 3'SL, the total amount of HMOs in the nutritional composition includes at least about 85% (by total weight HMOs) 3'SL, including from about 85% (by total weight HMOs) to about 88% (by total weight HMOs), including from about 85% (by total weight HMOs) to about 100% (by total weight HMOs), and including about 100% (by total weight HMOs) 3'SL.

In one specific embodiment, the nutritional composition includes LNnT, alone or in combination with other HMOs, in an amount of from about 0.001 mg/mL to about 20 mg/mL, including from about 0.01 mg/mL to about 20 mg/mL, including from about 0.001 mg/mL to less than 0.2 mg/mL, including from about 0.01 mg/mL to less than 0.2 mg/mL, including from about 0.001 mg/mL to about 0.1 mg/mL, and including from greater than 0.32 mg/mL to about 20 mg/mL.

In another specific embodiment, the nutritional composition includes 3'FL, alone or in combination with other HMOs, in an amount of from about 0.001 mg/mL to about 20 mg/mL, including from about 0.01 mg/mL to about 20 mg/mL, including from about 0.001 mg/mL to less than 1 mg/mL, including from about 0.01 mg/mL to less than 1 mg/mL, and including from greater than 1.7 mg/mL to about 20 mg/mL.

In one specific embodiment, the nutritional composition includes 3'FL in combination with SA in a total amount of HMO of from about 0.001 mg/mL to about 20 mg/mL, including from about 0.01 mg/mL to about 20 mg/mL. In one embodiment, the nutritional composition includes 3'FL in an amount of from 0.001 mg/mL to less than 1 mg/mL, including from 0.01 mg/mL to less than 1 mg/mL and SA in an amount of about 1 mg/mL.

In another embodiment, the nutritional composition includes 2'FL, alone or in combination with other HMOs, in an amount of from about 0.001 mg/mL to about 20 mg/mL, including from about 0.01 mg/mL to about 20 mg/mL, including from about 0.001 mg/mL to less than 2 mg/mL, including from about 0.01 mg/mL to less than 2 mg/mL, including from about 0.001 mg/mL to about 1 mg/mL, and including from about 0.01 mg/mL to about 0.001 mg/mL. In another embodiment, the nutritional composition includes 2'FL, alone or in combination with other HMOs, in an amount of from about 0.001 mg/mL to about 20 mg/mL, including from about 0.01 mg/mL to about 20 mg/mL and including greater than 2.5 mg/mL to about 20 mg/mL.

In one specific embodiment, the nutritional composition includes 2'FL in combination with 3'FL in a total amount of HMO of from 0.001 mg/mL to about 20 mg/mL, including from about 0.01 mg/mL to about 20 mg/mL.

In yet another embodiment, the nutritional composition includes a combination of 6'SL, 2'FL, and LNnT in a total amount of HMO of from about 0.001 mg/mL to about 20 mg/mL, including from about 0.01 mg/mL to about 20 mg/mL.

Long Chain Polyunsaturated Fatty Acids (LCPUFAs)

In addition to the HMOs described above, the nutritional products of the present disclosure may include LCPUFAs. LCPUFAs are included in the nutritional compositions to provide nutritional support, as well as to reduce oxidative stress and enhance growth and functional development of the intestinal epithelium and associated immune cell populations. In some embodiments, the nutritional composition includes a combination of one or more HMOs and one or more LCPUFAs such that the composition provides a synergistic benefit to the end user, such as a synergistic benefit in modulating anti-viral immune responses and dampening inflammation. In some embodiments, the HMO or HMOs used in combination with the LCPUFAs to provide the synergistic effect are acidic HMOs.

Exemplary LCPUFAs for use in the nutritional compositions include, for example, ω-3 LCPUFAs and ω-6 LCPUFAs. Specific LCPUFAs include docosahexaenoic acid (DHA), eicosapentaenoic acid (EPA), docosapentaenoic acid (DPA), acidarachidonic acid (ARA), linoleic acid, linolenic acid (alpha linolenic acid) and gamma-linolenic acid derived from oil sources such as plant oils, marine plankton, fungal oils, and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the HMOs include DHA, ARA, EPA, DPA, and combinations thereof.

In order to reduce potential side effects of high dosages of LCPUFAs in the nutritional compositions, the content of LCPUFAs preferably does not exceed 3% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, in esterified form or as a mixture of one or more of the above, preferably in triglyceride form.

The nutritional compositions as described herein will typically comprise total concentrations of LCPUFA of from about 0.01 mM to about 10 mM and including from about 0.01 mM to about 1 mM. Alternatively, the nutritional compositions comprise total concentrations of LCPUFA of from about 0.001 g/L to about 1 g/L.

In one embodiment, the nutritional compositions include total long chain ω-6 fatty acids in a concentration of from about 100 to about 425 mg/L or from about 12 to about 53 mg per 100 kcals and/or further include total long chain ω-3 fatty acids in a concentration of from about 40 to about 185 mg/L or from about 5 to about 23 mg per 100 kcals. In one specific embodiment, the ratio of long chain ω-6 fatty acids to long chain ω-3 fatty acids in the nutritional compositions ranges from about 2:1 to about 3:1, preferably about 2.5:1.

In one specific embodiment, the nutritional compositions include DHA in a concentration of from about 0.025 mg/mL to about 0.130 mg/mL or from about 3 to about 16 mg per 100 kcals. In another embodiment, the nutritional compositions include ARA in a concentration of from about 0.080 mg/mL to about 0.250 mg/mL or from about 10 to about 31 mg per 100 kcals. In yet another embodiment, the nutritional compositions include combinations of DHA and ARA such that the ratio of DHA to ARA ranges from about 1:4 to about 1:2.

Antioxidants

Additionally, the nutritional compositions may comprise one or more antioxidants in combination with the HMOs (and optionally LCPUFAs and/or nucleotides also) to provide nutritional support, as well as to reduce oxidative stress. In some embodiments, the nutritional composition includes a combination of HMOs and antioxidants such that the composition provides a synergistic benefit to the end user, such as a synergistic benefit in modulating anti-viral immune responses and dampening inflammation. In some embodiments, the HMO or HMOs is used in combination with carotenoids (and specifically lutein, beta-carotene, zeaxanthin and/or lycopene) to provide the synergistic effect.

Any antioxidants suitable for oral administration may be included for use in the nutritional compositions of the present disclosure, including, for example, vitamin A, vitamin E, vitamin C, retinol, tocopherol, and carotenoids, including lutein, beta-carotene, zeaxanthin, and lycopene, and combinations thereof, for example.

As noted, the antioxidants for use in the nutritional compositions may be used with the HMOs alone or in combination with HMOs and LCPUFAs and/or nucleotides. In one specific embodiment, the antioxidants for use in the nutritional compositions include carotenoids, and particularly, combinations of the carotenoids lutein, lycopene, zeaxanthin and/or beta-carotene. Nutritional compositions containing these combinations, as selected and defined herein, can be used to modulate inflammation and/or levels of C-reactive protein in preterm and term infants.

It is generally preferable that the nutritional compositions comprise at least one of lutein, lycopene, zeaxanthin, and beta-carotene to provide a total amount of carotenoid of from about 0.001 μg/mL to about 10 μg/mL. More particularly, the nutritional compositions comprise lutein in an amount of from about 0.001 μg/mL to about 10 μg/mL, including from about 0.01 μg/mL to about 10 μg/mL, including from about 0.01 μg/mL to about 1.5 μg/mL, including from about 4 μg/mL to about 6 μg/mL, including from about 0.001 μg/mL to about 5 μg/mL, including from about 0.001 μg/mL to about 0.0190 μg/mL, including from about 0.001 μg/mL to about 0.0140 μg/L, and also including from about 0.044 μg/mL to about 5 μg/mL of lutein. It is also generally preferable that the nutritional compositions comprise from about 0.001 μg/mL to about 10 μg/mL, including from about 0.01 μg/mL to about 10 μg/mL, including from about 0.01 μg/mL to about 1.5 μg/mL, including from about 4 μg/mL to about 6 μg/mL, including from about 0.001 μg/mL to about 5 μg/mL, from about 0.001 μg/mL to about 0.0130 μg/mL, including from about 0.001 μg/mL to about 0.0075 μg/mL, and also including from about 0.0185 μg/mL to about 5 μg/mL of lycopene. It is also generally preferable that the nutritional compositions comprise from about 0.001 μg/mL to about 10 μg/mL, including from about 0.01 μg/mL to about 10 μg/mL, including from about 0.01 μg/mL to about 1.5 μg/mL, including from about 4 μg/mL to about 6 μg/mL, including from about 1 μg/mL to about 10 μg/mL, including from about 1 μg/mL to about 5 μg/mL, including from about 0.001 μg/mL to about 0.025 μg/mL, including from about 0.001 μg/mL to about 0.011 μg/mL, and also including from about 0.034 μg/mL to about 5 μg/mL of beta-carotene. It should be understood that any combination of these amounts of beta-carotene, lutein, zeaxanthin, and lycopene can be included in the nutritional compositions of the present disclosure. Other carotenoids may optionally be included in the nutritional compositions as described herein. Any one or all of the carotenoids included in the nutritional compositions described herein may be from a natural source, or artificially synthesized.

Each of the carotenoids in the selected combinations can be obtained from any known or otherwise suitable material source for use in nutritional compositions, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LycoVit® lycopene (available from BASF, Mount Olive, N.J.), Lyc-O-Mato® tomato extract in oil, powder, or bead form (available from LycoRed Corp., Orange, N.J.), beta-carotene, lutein, or lycopene (available from DSM Nutritional Products, Parsippany, N.J.), FloraGLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J.).

Nucleotides

In addition to the HMOs, the nutritional compositions of the present disclosure may additionally comprise nucleotides and/or nucleotide precursors selected from the group consisting of nucleosides, purine bases, pyrimidine bases, ribose and deoxyribose. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt. In some embodiments, the nutritional composition includes a combination of HMOs and nucleotides such that the composition provides a synergistic benefit to the end user, such as a synergistic benefit in modulating anti-viral immune responses and dampening inflammation and/or improving intestinal barrier integrity.

Incorporation of nucleotides in the nutritional compositions of the present disclosure improves intestinal barrier integrity and/or maturation, which is beneficial to preterm and term infants who have less developed intestinal flora and hence a slower maturing intestinal barrier.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, more preferably cytidine 5'-monophosphate, uridine 5'-monophosphate, adenosine 5'-monophosphate, guanosine 5'-monophosphate, and inosine 5'-monophosphate.

The nucleotides are present in the nutritional products in total amounts of nucleotides of at least about 5 mg/L, including at least about 10 mg/L, including from about 10 mg/L to about 200 mg/L, including from about 42 mg/L to about 102 mg/L, and including at least about 72 mg/L of the nutritional product.

In one specific embodiment when the nutritional composition is a nutritional powder, the nucleotide may be present at a level of at least about 0.007%, including from about 0.0078% to about 0.1556%, and including about 0.056% (by weight of the nutritional powder), or at least about 0.007 grams, including from about 0.0078 grams to about 0.1556 grams, and including about 0.056 grams of nucleotide per 100 grams of nutritional powder.

In another specific embodiment, when the nutritional composition is a ready-to-feed nutritional liquid, the nucleotide is present at a level of at least about 0.001%, including from about 0.001% to about 0.0197%, and including about 0.0071% (by weight of the nutritional liquid), or at least about 0.001 grams, including from about 0.001 grams to about 0.0197 grams, and including about 0.0071 grams of nucleotide per 100 grams of ready-to-feed nutritional liquid.

In another specific embodiment when the nutritional composition is a concentrated nutritional liquid, the nucleotide is present at a level of at least about 0.0019%, including from about 0.0019% to about 0.0382%, and including about 0.0138% (by weight of the nutritional liquid), or at least about 0.0019 grams, including from about 0.0019 grams to about 0.0382 grams, and including about 0.0138 grams of nucleotide per 100 grams of concentrated nutritional liquid.

Macronutrients

The nutritional compositions including the HMO or HMOs may be formulated to include at least one of protein, fat, and carbohydrate. In many embodiments, the nutritional compositions will include the HMO or HMOs with protein, carbohydrate and fat.

Although total concentrations or amounts of the fat, protein, and carbohydrates may vary depending upon the product type (i.e., human milk fortifier, preterm infant formula, infant formula, etc.), product form (i.e., nutritional solid, powder, ready-to-feed liquid, or concentrated liquid) and targeted dietary needs of the intended user, such concentrations or amounts most typically fall within one of the following embodied ranges, inclusive of any other essential fat, protein, and/or carbohydrate ingredients as described herein.

For the liquid preterm and term infant formulas, carbohydrate concentrations most typically range from about 5% to about 40%, including from about 7% to about 30%, including from about 10% to about 25%, by weight of the preterm or term infant formula; fat concentrations most typically range from about 1% to about 30%, including from about 2% to about 15%, and also including from about 3% to about 10%, by weight of the preterm or term infant formula; and protein concentrations most typically range from about 0.5% to about 30%, including from about 1% to about 15%, and also including from about 2% to about 10%, by weight of the preterm or term infant formula.

For the liquid human milk fortifiers, carbohydrate concentrations most typically range from about 10% to about 75%, including from about 10% to about 50%, including from about 20% to about 40%, by weight of the human milk fortifier; fat concentrations most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

The amount of carbohydrates, fats, and/or proteins in any of the liquid nutritional compositions described herein may also be characterized in addition to, or in the alternative, as a percentage of total calories in the liquid nutritional composition as set forth in the following table. These macronutrients for liquid nutritional compositions of the present disclosure are most typically formulated within any of the caloric ranges (embodiments A-F) described in the following table (each numerical value is preceded by the term "about").

| Nutrient % Total Cal. | Embodiment A | Embodiment B | Embodiment C |
|---|---|---|---|
| Carbohydrate | 0-98 | 2-96 | 10-75 |
| Protein | 0-98 | 2-96 | 5-70 |
| Fat | 0-98 | 2-96 | 20-85 |

| | Embodiment D | Embodiment E | Embodiment F |
|---|---|---|---|
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

| Nutrient % Total Cal. | Embodiment G | Embodiment H | Embodiment I |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional product is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component is present in an amount of from about 30% to about 85%, including from about 45% to about 60%, including from about 50% to about 55% by weight of the preterm or term infant formula.

For powdered human milk fortifiers the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component is present in an amount of from about 15% to about 75%, including from about 15% to about 60%, including from about 20% to about 50% by weight of the human milk fortifier.

The total amount or concentration of fat, carbohydrate, and protein, in the powdered nutritional compositions of the present disclosure can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered product. For powdered nutritional compositions, such total amounts or concentrations are most typically and preferably formulated within any of the embodied ranges described in the following table (each numerical value is preceded by the term "about").

| Nutrient % Total Cal. | Embodiment J | Embodiment K | Embodiment L |
|---|---|---|---|
| Carbohydrate | 1-85 | 30-60 | 35-55 |
| Fat | 5-70 | 20-60 | 25-50 |
| Protein | 2-75 | 5-50 | 7-40 |

Fat

The nutritional compositions of the present disclosure may, in addition to the LCPUFAs described above, comprise an additional source or sources of fat. Suitable additional sources of fat for use herein include any fat or fat source that is suitable for use in an oral nutritional product and is compatible with the essential elements and features of such products. For example, in one specific embodiment, the additional fat is derived from short chain fatty acids.

Additional non-limiting examples of suitable fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions of the present disclosure may optionally further comprise protein. Any protein source that is suitable for use in oral nutritional compositions and is compatible with the essential elements and features of such products is suitable for use in the nutritional compositions.

Non-limiting examples of suitable proteins or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

Carbohydrate

The nutritional products of the present disclosure may further optionally comprise any carbohydrates that are suitable for use in an oral nutritional product and are compatible with the essential elements and features of such products.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The nutritional compositions of the present disclosure may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, fructooligosaccharides, galactooligosaccharides, polydextrose, and other prebiotics, probiotics, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage.

Optional sugar alcohol concentrations in the nutritional product may range from at least 0.01%, including from about 0.1% to about 10%, and also including from about 1% to about 6%, by weight of the nutritional product. Optional artificial sweetener concentrations may range from about 0.01%, including from about 0.05% to about 5%, also including from about 0.1% to about 1.0%, by weight of the nutritional product.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional compositions may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective techniques, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional products are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application 20030118703 A1 (Nguyen, et al.), which descriptions are incorporated herein by reference to the extent that they are consistent herewith.

Methods of Use

The nutritional compositions as described herein can be used to address one or more of the diseases or conditions discussed herein, or can be used to provide one or more of the benefits described herein, to preterm infants, infants, toddlers, and children. The preterm infant, infant, toddler, or child utilizing the nutritional compositions described herein may actually have or be afflicted with the disease or condition described, or may be susceptible to, or at risk of, getting the disease or condition (that is, may not actually yet have the disease or condition, but is at elevated risk as compared to the general population for getting it due to certain conditions, family history, etc.) Whether the preterm infant, infant, toddler, or child actually has the disease or condition, or is at risk or susceptible to the disease or condition, the preterm infant, infant, toddler, or child is classified herein as "in need of" assistance in dealing with and combating the disease or condition. For example, the preterm infant, infant, toddler, or child may actually have respiratory inflammation or may be at risk of getting respiratory inflammation (susceptible to getting respiratory inflammation) due to family history or other medical conditions, for example. Whether the preterm infant, infant, toddler, or child actually has the disease or condition, or is only at risk or susceptible to getting the disease or condition, it is within the scope of the present disclosure to assist the preterm infant, infant, toddler, or child with the nutritional compositions described herein.

Based on the foregoing, because some of the method embodiments of the present disclosure are directed to specific subsets or subclasses of identified individuals (that is, the subset or subclass of individuals "in need" of assistance in addressing one or more specific diseases or specific conditions noted herein), not all preterm infants, infants, toddlers, and children will fall within the subset or subclass of preterm infants, infants, toddlers, and children as described herein for certain diseases or conditions.

The nutritional compositions as described herein comprise HMOs, alone or in combination with one or more additional components, to provide a nutritional source for reducing inflammation, such as respiratory inflammation (e.g., respiratory syncytial virus-induced inflammation), enteric inflammation, and nasopharyngeal inflammation. The nutritional compositions of the present disclosure comprising HMOs may also provide optimal development and balanced growth and maturation of the infant's gastrointestinal and immune systems, thereby enhancing the infant's ability to resist microbial infection and modulate inflammatory responses to infection (e.g., increased phagocytosis and increased production of reactive oxidative species).

The nutritional compositions also provide growth and maturation of the intestinal epithelial cells in an infant. In one specific embodiment, the administration of the nutritional compositions of the present disclosure including HMOs and nucleotides can further activate immune activity in or by the intestinal epithelial cells in a newborn.

Further, the use of HMOs in nutritional compositions can reduce the growth of respiratory viruses (e.g., RSV, human parainfluenza virus type 2, and influenza A virus), and thus, reduce viral-induced upper respiratory infections. As such, by utilizing HMOs, alone or in combination with other immune enhancing factors, in a nutritional product, such as an infant formula, it is now possible to provide infants with an alternative, or supplement, to breast milk that more closely mimics the benefits thereof.

Along with improved growth and maturation of the infant's immune system as described above, the use of the nutritional compositions of the present disclosure also functions as an immune modulator, thereby reducing inflammation induced by infection in infants, toddlers, and children such as respiratory virus-induced infection, and particularly, RSV-induced inflammation, and other infection-mediated inflammatory diseases. By improving the growth and maturation of the immune system and reducing inflammation, the airway defense mechanisms of an infant, toddler, or child can be improved, thus improving the overall respiratory health of the infant, toddler, or child. Specifically, in some embodiments of the present disclosure, the HMO-containing nutritional compositions of the present disclosure can be used by an infant, toddler, or child to improve airway defense mechanisms. In other embodiments of the present disclosure, the HMO-containing nutritional compositions can be used by an infant, toddler, or child to improve overall airway respiratory health.

The addition of HMOs can further increase glutathione levels in the body and blood of an infant, and in specific embodiments, of a preterm infant.

When used in combination with LCPUFAs and/or antioxidants, and particularly, with carotenoids, the HMOs can reduce oxidative stress, which is a metabolic condition in which there is an increased production and accumulation of oxidized biomolecules such as lipid peroxides and their catabolites, protein carbonyls, and oxidatively damaged DNA. The outcomes of oxidative stress range from unwanted changes in metabolism to inflammation and cell and tissue death. Accordingly, by reducing the incidence of unregulated inflammation and oxidation in the infant, damage to the tissue lining and cell death is reduced, further reducing the incidence of inflammatory diseases, such as necrotizing enterocolitis (NEC).

In addition to the benefits discussed above, it has been discovered that nutritional products including HMOs can modulate production of monocyte-derived cytokines in the infant, even in the absence of a virus. This production results in improved immunity to further prevent microbial infection and reduce the growth of viruses. In one specific embodiment, monocyte-derived cytokines produced by administration of the nutritional compositions of the present disclosure include, for example, interleukin-10, interleukin-8, interleukin-1α, interleukin-1β, interleukin-1ra, and combinations thereof.

Another benefit of utilizing HMOs in nutritional compositions is that it has been discovered that HMOs modulate the production of IP-10, which is a chemokine that plays an important role in the inflammatory response to viral infection. Specifically, a positive correlation exists between RSV clinical infection severity in children and serum IP-10 levels. Accordingly, a decrease in IP-10 signals a decrease in severity of RSV infection. In one specific embodiment, IP-10 production is reduced to the level found in uninfected controls.

Along with reducing IP-10, HMOs have been found to reduce platelet-neutrophil complex (PNC) formation, which is present in human blood and consists of up to 25% of unstimulated neutrophils. As PNCs are present in aggregates, they have a greater capacity to initiate inflammatory processes and can increase the production of reactive oxidative species. Accordingly, a decrease in PNC formation can lead to reduced oxidative stress and inflammation in the infant.

EXAMPLES

The following examples illustrate specific embodiments and/or features of the nutritional compositions of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

Examples 1-5

Examples 1-5 illustrate ready-to-feed nutritional emulsions of the present disclosure, the ingredients of which are listed in the table below. All ingredient amounts are listed as kilogram per 1000 kilogram batch of product, unless otherwise specified.

| Ingredient | Ex. 1 | Ex. 2 | Ex. 3 | Ex. 4 | Ex. 5 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 3' sialyllactose (3'SL) | 0.0948 | 0.090 | 0.085 | 9.479 | 9.005 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.4 g | 47.4 g | 47.4 g | 47.4 g | 47.4 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 6-10

Examples 6-10 illustrate ready-to-feed nutritional emulsions of the present disclosure, the ingredients of which are listed in the table below. All ingredient amounts are listed as kilogram per 1000 kilogram batch of product, unless otherwise specified.

| Ingredient | Ex. 6 | Ex. 7 | Ex. 8 | Ex. 9 | Ex. 10 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 6' sialyllactose (6'SL) | 0.0948 | 0.0901 | 0.0853 | 9.479 | 9.0047 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |

-continued

| Ingredient | Ex. 6 | Ex. 7 | Ex. 8 | Ex. 9 | Ex. 10 |
|---|---|---|---|---|---|
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 11-15

Examples 11-15 illustrate concentrated liquid emulsions of the present disclosure, the ingredients of which are listed in the table below. All ingredient amounts are listed as kilogram per 1000 kilogram batch of product, unless otherwise specified.

| Ingredient | Ex. 11 | Ex. 12 | Ex. 13 | Ex. 14 | Ex. 15 |
|---|---|---|---|---|---|
| Water | Q.S. | Q.S. | Q.S. | Q.S. | Q.S. |
| Condensed Skim Milk | 157.67 | 157.67 | 157.67 | 157.67 | 157.67 |
| Lactose | 108.66 | 108.66 | 108.66 | 108.66 | 108.66 |
| High oleic safflower oil | 26.82 | 26.82 | 26.82 | 26.82 | 26.82 |
| Soybean oil | 20.16 | 20.16 | 20.16 | 20.16 | 20.16 |
| Coconut oil | 19.24 | 19.24 | 19.24 | 19.24 | 19.24 |
| 3' sialyllactose (3'SL) | 0.1896 | 0.1802 | 0.1706 | 18.958 | 18.009 |
| Galactooligosaccharides (GOS) | 17.67 | 17.67 | 17.67 | 17.67 | 17.67 |
| Whey protein concentrate | 12.20 | 12.20 | 12.20 | 12.20 | 12.20 |
| Potassium citrate | 1.277 | 1.277 | 1.277 | 1.277 | 1.277 |
| Calcium carbonate | 996.1 g | 996.1 g | 996.1 g | 996.1 g | 996.1 g |
| Soy lecithin | 685.0 g | 685.0 g | 685.0 g | 685.0 g | 685.0 g |
| Monoglycerides | 685.0 g | 685.0 g | 685.0 g | 685.0 g | 685.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 429.7 g | 429.7 g | 429.7 g | 429.7 g | 429.7 g |
| Ascorbic acid | 293.8 g | 293.8 g | 293.8 g | 293.8 g | 293.8 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |
| Carrageenan | 200.0 g | 200.0 g | 200.0 g | 200.0 g | 200.0 g |
| Magnesium chloride | 173.3 g | 173.3 g | 173.3 g | 173.3 g | 173.3 g |
| Ferrous sulfate | 112.7 g | 112.7 g | 112.7 g | 112.7 g | 112.7 g |
| Choline chloride | 104.8 g | 104.8 g | 104.8 g | 104.8 g | 104.8 g |
| Vitamin A, $D_3$, E, $K_1$ premix | 86.90 g | 86.90 g | 86.90 g | 86.90 g | 86.90 g |
| Citric acid | 57.50 g | 57.50 g | 57.50 g | 57.50 g | 57.50 g |
| Mixed carotenoid premix | 41.90 g | 41.90 g | 41.90 g | 41.90 g | 41.90 g |
| Sodium chloride | 23.50 g | 23.50 g | 23.50 g | 23.50 g | 23.50 g |
| L-carnitine | 6.40 g | 6.40 g | 6.40 g | 6.40 g | 6.40 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 16-20

Examples 16-20 illustrate ready-to-feed nutritional emulsions of the present disclosure, the ingredients of which are listed in the table below. All ingredient amounts are listed as kilogram per 1000 kilogram batch of product, unless otherwise specified.

| Ingredient | Ex. 16 | Ex. 17 | Ex. 18 | Ex. 19 | Ex. 20 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| HMO Mixture | 0.0948 | 0.0901 | 0.0853 | 9.479 | 9.0047 |

-continued

| Ingredient | Ex. 16 | Ex. 17 | Ex. 18 | Ex. 19 | Ex. 20 |
|---|---|---|---|---|---|
| 6' sialyllactose (6'SL) | 0.0316 | 0.0300 | 0.0284 | 3.159 | 3.002 |
| 2'fucosyllactose (2'FL) | 0.0316 | 0.0300 | 0.0284 | 3.159 | 3.002 |
| Lacto-N-neotetraose (LNnT) | 0.0316 | 0.0300 | 0.0284 | 3.159 | 3.002 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 21-25

Examples 21-25 illustrate concentrated liquid emulsions of the present disclosure, the ingredients of which are listed in the table below. All ingredient amounts are listed as kilogram per 1000 kilogram batch of product, unless otherwise specified.

| Ingredient | Ex. 21 | Ex. 22 | Ex. 23 | Ex. 24 | Ex. 25 |
|---|---|---|---|---|---|
| Water | Q.S. | Q.S. | Q.S. | Q.S. | Q.S. |
| Condensed Skim Milk | 157.67 | 157.67 | 157.67 | 157.67 | 157.67 |
| Lactose | 108.66 | 108.66 | 108.66 | 108.66 | 108.66 |
| High oleic safflower oil | 26.82 | 26.82 | 26.82 | 26.82 | 26.82 |
| Soybean oil | 20.16 | 20.16 | 20.16 | 20.16 | 20.16 |
| Coconut oil | 19.24 | 19.24 | 19.24 | 19.24 | 19.24 |
| HMO Mixture | 18.957 | 18.009 | 17.061 | 19.905 | 20.853 |
| 6' sialyllactose (6'SL) | 6.319 | 6.003 | 5.687 | 6.635 | 6.951 |
| 2'fucosyllactose (2'FL) | 6.319 | 6.003 | 5.687 | 6.635 | 6.951 |
| Lacto-N-neotetraose (LNnT) | 6.319 | 6.003 | 5.687 | 6.635 | 6.951 |
| Galactooligosaccharides (GOS) | 17.67 | 17.67 | 17.67 | 17.67 | 17.67 |
| Whey protein concentrate | 12.20 | 12.20 | 12.20 | 12.20 | 12.20 |
| Potassium citrate | 1.277 | 1.277 | 1.277 | 1.277 | 1.277 |
| Calcium carbonate | 996.1 g | 996.1 g | 996.1 g | 996.1 g | 996.1 g |
| Soy lecithin | 685.0 g | 685.0 g | 685.0 g | 685.0 g | 685.0 g |
| Monoglycerides | 685.0 g | 685.0 g | 685.0 g | 685.0 g | 685.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 429.7 g | 429.7 g | 429.7 g | 429.7 g | 429.7 g |
| Ascorbic acid | 293.8 g | 293.8 g | 293.8 g | 293.8 g | 293.8 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |
| Carrageenan | 200.0 g | 200.0 g | 200.0 g | 200.0 g | 200.0 g |
| Magnesium chloride | 173.3 g | 173.3 g | 173.3 g | 173.3 g | 173.3 g |
| Ferrous sulfate | 112.7 g | 112.7 g | 112.7 g | 112.7 g | 112.7 g |
| Choline chloride | 104.8 g | 104.8 g | 104.8 g | 104.8 g | 104.8 g |
| Vitamin A, $D_3$, E, $K_1$ premix | 86.90 g | 86.90 g | 86.90 g | 86.90 g | 86.90 g |
| Citric acid | 57.50 g | 57.50 g | 57.50 g | 57.50 g | 57.50 g |
| Mixed carotenoid premix | 41.90 g | 41.90 g | 41.90 g | 41.90 g | 41.90 g |
| Sodium chloride | 23.50 g | 23.50 g | 23.50 g | 23.50 g | 23.50 g |
| L-carnitine | 6.40 g | 6.40 g | 6.40 g | 6.40 g | 6.40 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 26-30

Examples 26-30 illustrate human milk fortifier liquids of the present disclosure, the ingredients of which are listed in the table below. All ingredient amounts are listed as kilogram per 1000 kilogram batch of product, unless otherwise specified.

| Ingredient | Ex. 26 | Ex. 27 | Ex. 28 | Ex. 29 | Ex. 30 |
|---|---|---|---|---|---|
| Water | Q.S. | Q.S. | Q.S. | Q.S. | Q.S. |
| Non-fat milk | 353 | 353 | 353 | 353 | 353 |
| Corn Syrup Solids | 85.3 | 85.3 | 85.3 | 85.3 | 85.3 |
| Medium Chain Triglycerides | 53.2 | 53.2 | 53.2 | 53.2 | 53.2 |
| Whey Protein Concentrate | 47.2 | 47.2 | 47.2 | 47.2 | 47.2 |

| Ingredient | Ex. 26 | Ex. 27 | Ex. 28 | Ex. 29 | Ex. 30 |
| --- | --- | --- | --- | --- | --- |
| HMO Mixture | 18.957 | 18.009 | 17.061 | 19.905 | 20.853 |
| 6' sialyllactose (6'SL) | 6.319 | 6.003 | 5.687 | 6.635 | 6.951 |
| 2'fucosyllactose (2'FL) | 6.319 | 6.003 | 5.687 | 6.635 | 6.951 |
| Lacto-N-neotetraose (LNnT) | 6.319 | 6.003 | 5.687 | 6.635 | 6.951 |
| Calcium Phosphate | 25.5 | 25.5 | 25.5 | 25.5 | 25.5 |
| Ascorbic Acid | 5.6 | 5.6 | 5.6 | 5.6 | 5.6 |
| Potassium Citrate | 3.1 | 3.1 | 3.1 | 3.1 | 3.1 |
| Magnesium Chloride | 2.8 | 2.8 | 2.8 | 2.8 | 2.8 |
| Sodium Citrate | 1.4 | 1.4 | 1.4 | 1.4 | 1.4 |
| Sodium Chloride | 1.4 | 1.4 | 1.4 | 1.4 | 1.4 |
| Soy Lecithin | 609 g | 609 g | 609 g | 609 g | 609 g |
| M-Inositol | 500 g | 500 g | 500 g | 500 g | 500 g |
| Niacinamide | 400 g | 400 g | 400 g | 400 g | 400 g |
| ARA Oil | 313 g | 313 g | 313 g | 313 g | 313 g |
| Tocopherol Acetate | 310 g | 310 g | 310 g | 310 g | 310 g |
| Zinc Sulfate | 300 g | 300 g | 300 g | 300 g | 300 g |
| Calcium Pantothenate | 182 g | 182 g | 182 g | 182 g | 182 g |
| Ferrous Sulfate | 133 g | 133 g | 133 g | 133 g | 133 g |
| DHA Oil | 116 g | 116 g | 116 g | 116 g | 116 g |
| Vitamin A Palmitate | 100 g | 100 g | 100 g | 100 g | 100 g |
| Cupric Sulfate | 51.0 g | 51.0 g | 51.0 g | 51.0 g | 51.0 g |
| Thiamine Hydrochloride | 50.0 g | 50.0 g | 50.0 g | 50.0 g | 50.0 g |
| Riboflavin | 47.0 g | 47.0 g | 47.0 g | 47.0 g | 47.0 g |
| Pyridoxine Hydrochloride | 27.0 g | 27.0 g | 27.0 g | 27.0 g | 27.0 g |
| Vitamin $D_3$ | 20.0 g | 20.0 g | 20.0 g | 20.0 g | 20.0 g |
| Folic Acid | 3.5 g | 3.5 g | 3.5 g | 3.5 g | 3.5 g |
| Biotin | 3.4 g | 3.4 g | 3.4 g | 3.4 g | 3.4 g |
| Manganous Sulfate | 1.5 g | 1.5 g | 1.5 g | 1.5 g | 1.5 g |
| Phylloquinone | 1.2 g | 1.2 g | 1.2 g | 1.2 g | 1.2 g |
| Cyanocobalamin | 100 mg | 100 mg | 100 mg | 100 mg | 100 mg |
| Sodium Selenate | 43.0 mg | 43.0 mg | 43.0 mg | 43.0 mg | 43.0 mg |

Examples 31-35

Examples 31-35 illustrate spray dried nutritional powders of the present disclosure, the ingredients of which are listed in the table below. All ingredient amounts are listed as kilogram per 1000 kilogram batch of product, unless otherwise specified.

| Ingredient | Ex. 31 | Ex. 32 | Ex. 33 | Ex. 34 | Ex. 35 |
| --- | --- | --- | --- | --- | --- |
| Condensed Skim Milk | 698.5 | 698.5 | 698.5 | 698.5 | 698.5 |
| Lactose | 386.0 | 386.0 | 386.0 | 386.0 | 386.0 |
| High oleic safflower oil | 114.4 | 114.4 | 114.4 | 114.4 | 114.4 |
| Soybean oil | 85.51 | 85.51 | 85.51 | 85.51 | 85.51 |
| Coconut oil | 78.76 | 78.76 | 78.76 | 78.76 | 78.76 |
| 3' sialyllactose (3'SL) | 0.3792 | 0.3604 | 0.3412 | 37.916 | 36.0188 |
| Galactooligosaccharides (GOS) | 69.50 | 69.50 | 69.50 | 69.50 | 69.50 |
| Whey protein concentrate | 51.08 | 51.08 | 51.08 | 51.08 | 51.08 |
| Potassium citrate | 9.168 | 9.168 | 9.168 | 9.168 | 9.168 |
| Calcium carbonate | 4.054 | 4.054 | 4.054 | 4.054 | 4.054 |
| Soy lecithin | 1.120 | 1.120 | 1.120 | 1.120 | 1.120 |
| ARA oil | 2.949 | 2.949 | 2.949 | 2.949 | 2.949 |
| Nucleotide/chloride premix | 2.347 | 2.347 | 2.347 | 2.347 | 2.347 |
| Potassium chloride | 1.295 | 1.295 | 1.295 | 1.295 | 1.295 |
| Ascorbic acid | 1.275 | 1.275 | 1.275 | 1.275 | 1.275 |
| Vitamin mineral premix | 1.116 | 1.116 | 1.116 | 1.116 | 1.116 |
| DHA oil | 1.113 | 1.113 | 1.113 | 1.113 | 1.113 |
| Magnesium chloride | 1.038 | 1.038 | 1.038 | 1.038 | 1.038 |
| Sodium chloride | 579.4 g | 579.4 g | 579.4 g | 579.4 g | 579.4 g |
| Ferrous sulfate | 453.6 g | 453.6 g | 453.6 g | 453.6 g | 453.6 g |
| Choline chloride | 432.1 g | 432.1 g | 432.1 g | 432.1 g | 432.1 g |
| Vitamin A, $D_3$, E, $K_1$ premix | 377.2 g | 377.2 g | 377.2 g | 377.2 g | 377.2 g |
| Ascorbyl Palmitate | 361.3 g | 361.3 g | 361.3 g | 361.3 g | 361.3 g |
| Mixed carotenoid premix | 350.1 g | 350.1 g | 350.1 g | 350.1 g | 350.1 g |
| Mixed Tocopherols | 159.2 g | 159.2 g | 159.2 g | 159.2 g | 159.2 g |
| L-carnitine | 26.30 g | 26.30 g | 26.30 g | 26.30 g | 26.30 g |
| Riboflavin | 3.181 g | 3.181 g | 3.181 g | 3.181 g | 3.181 g |

-continued

| Ingredient | Ex. 31 | Ex. 32 | Ex. 33 | Ex. 34 | Ex. 35 |
|---|---|---|---|---|---|
| Tricalcium phosphate | 0-5.23 | 0-5.23 | 0-5.23 | 0-5.23 | 0-5.23 |
| Potassium phosphate monobasic | 0-5.23 | 0-5.23 | 0-5.23 | 0-5.23 | 0-5.23 |
| Potassium hydroxide | AN | AN | AN | AN | AN |

AN = as needed

Example 36

In this Example, the effect of purified human milk oligosaccharides (HMO) on in vitro inhibition of viral infectivity is analyzed.

Samples are prepared by co-incubation of a uniform virus dose of from about 500 units/mL to about 1,000 units/mL of one of three respiratory viruses: (1) respiratory syncytial virus (RSV); (2) human parainfluenza virus (HPIV3); or (3) H1N1 influenza virus with one of the following HMOs: (1) 3'-sialyllactose (3'SL); (2) 6'-sialyllactose (6'SL); (3) 3'-fucosyllactose (3'FL); (4) 2'-fucosyllactose (2'FL); (5) lacto-N-neotetraose (LNnT); or (6) sialic acid (SA). The HMOs are added at concentrations of either 1 mg/mL or 10 mg/mL. The antiviral activities of the various HMOs on the respiratory viruses are evaluated, and the results are shown in the table below:

| | IC50 (mg HMO/mL) | | |
|---|---|---|---|
| HMO | RSV | HPIV3 | H1N1 Influenza |
| 3'SL | >10 | >10 | ~5 |
| 6'SL | >10 | >10 | ~10 |
| 3'FL | ~5 | ~2 | ~5 |
| 2'FL | >10 | >10 | ~10 |
| LNnT | >10 | NT | >10 |
| SA | NT | ~2 | ~5 |

NT = Not Tested

The results show that 3'FL, at a concentration of 1 mg/ML (IC50~2-5 mg/ML), has anti-viral activity for all three respiratory viruses. This result is unexpected as previous published reports show only sialylated oligo forms providing antiviral activity. SA significantly inhibits HPIV3 and H1N1 viruses at a concentration of 1 mg/mL. H1N1 influenza virus is also inhibited by 3'SL at a concentration of 1 mg/mL.

Example 37

In this Example, the ability of various HMOs to block H1N1 influenza virus infectivity in vitro is analyzed.

Virus infectivity is assessed by observing cytopathic effect (CPE) and quantifying virus focus forming units. To create virus stocks, H1N1 influenza virus is purchased from ATCC (VR 1469) and expanded in Madin-Darby Canine Kidney (MDCK) epithelial cells (ATCC CCL-34). Cell-free supernatants are frozen in aliquots to maintain stock virus. During initial virus culture and expansion to create virus stocks, cell CPE is observed.

To quantify virus infectivity, an immunocytochemical focus forming unit (FFU) assay is developed using commercially purchased mouse monoclonal antibodies against the virus nucleoprotein coupled with a biotinylated anti-mouse IgG secondary antibody. To visualize virus-infected cell foci, color development is performed using Strepavidin HRP (ABC from Vector Laboratories, Inc.). Although the total number of virus foci appear proportional to the infecting virus concentration, the foci are quite large, disperse, and there are numerous individually infected cells that do not form foci, especially at higher virus concentrations. As this makes quantifying of virus infectivity difficult and time-consuming, the FFU assay is further refined by varying virus concentration and by applying an overlay medium of Tragacanth gum to help reduce Brownian movement spread of the virus throughout the cell layer.

The use of Tragacanth gum improves the assay by reducing the number of individually infected cells while still allowing for the formation of readily observable foci. While the foci vary in size, with some being quite large, they are still easily quantified and directly proportional to virus concentration or titer by using a grid technique during the enumeration.

Once verified, the assay is used with various HMOs for the ability to block H1N1 virus infectivity. Specifically, the HMOs are added, at concentrations of 0.01 mg/mL, 0.1 mg/mL, 1.0 mg/mL, and 10 mg/mL, to the inoculating virus suspension, incubated at 37° C. for one hour, and then added to MDCK monolayer cells. This mixture is allowed to bind to the cell layer for thirty minutes at 37° C. The cell layer is then washed, and the cells are further incubated for approximately 18-24 hours before fixing and processing for immunocytochemical staining. The results are shown in FIG. 1.

As shown in FIG. 1, 3'FL, 3'SL, and SA each inhibit virus infectivity by greater than 90% when used at a concentration of 10 mg/mL. 2'FL and 6'SL inhibit infectivity by approximately 60% at 10 mg/mL.

Example 38

In this Example, nutritional compositions including various HMOs are evaluated for their effects on reducing oxidative stress in preterm piglets.

Preterm piglets are harvested by caesarian section (CS) at 92% of gestation. Piglets receive total parenteral nutrition (TPN) for 48 hours. After 48 hours, TPN is ceased and the piglets are randomized into three groups: a formula group (n=7) that is fed Enfamil® Lacto-Free, commercially available from Mead Johnson, Evansville, Ind.; a treatment group (n=9) that is fed Enfamil® Lacto-Free with the addition of a combination of 400 mg/L 6'SL, 1500 mg/L 2'FL, and 200 mg/L LNnT; and a colostrum group (n=5) that is fed bovine colostrum. Piglets are fed their respective feeding enterally at a rate of 120 mL formula per kg body weight for the next 48 hours. Piglets are then euthanized after 48 hours of enteral nutrition (EN), or earlier if a piglet develops signs of necrotizing enterocolitis. Blood is collected via an umbilical artery catheter, and plasma is separated from the blood and stored at −70° C. until analyzed.

Glutathione (GSH) concentrations are measured in plasma taken from the piglets just prior to feeding time (time 0), and at 6 hours, 12 hours, 24 hours, 36 hours, and 48 hours after feeding using a commercially available assay (NWLSS Glutathione Assay #NWK-GSH01, Northwest Life Science Specialties, Vancouver, Wash.). The results are shown in FIG. 2.

As shown in FIG. 2, the concentration of GSH in blood plasma from the control group declines from time 0 to 6 hours after feeding. GSH remains lower in the control group 24 hours after EN. In contrast, piglets fed the composition with a combination of HMOs have a pattern of blood plasma GSH levels that are comparable to the colostrum piglets.

Example 39

In this Example, the abilities of 3'SL, 6'SL, and LNnT to reduce virus-induced inflammation in vitro are demonstrated.

Specifically, either 3'SL or 6'SL is added, at concentrations of 0.1 mg/mL, 0.2 mg/mL, or 0.5 mg/mL to fresh peripheral blood mononuclear cells and incubated at 37° C. in 5% $CO_2$ to pretreat the cells for approximately 24 hours. LNnT is added, at concentrations of 0.1 mg/mL, 0.2 mg/mL, or 1 mg/mL to fresh peripheral blood mononuclear cells and incubated at 37° C. in 5% $CO_2$ to pretreat the cells for approximately 24 hours. Lactose is included as a carbohydrate control. Matched endotoxin unit concentration controls are included to allow differentiation of ingredient effects from inherent low levels of endotoxin. Some variables are then incubated with RSV at a multiplicity of infection (MOI) of 0.1 for approximately 1 hour at 37° C. in 5% in $CO_2$. Uninfected control variables are incubated with medium for approximately 1 hour at 37° C. in 5% $CO_2$. After approximately one hour, fresh medium alone, or fresh medium containing the appropriate concentration of 3'SL, 6'SL, LNnT, lactose, or endotoxin is added to the appropriate tubes and the cells are incubated for 48 hours at 37° C. in 5% $CO_2$ Supernatants are collected at 24 and 48 hours post-infection.

Figure 4:
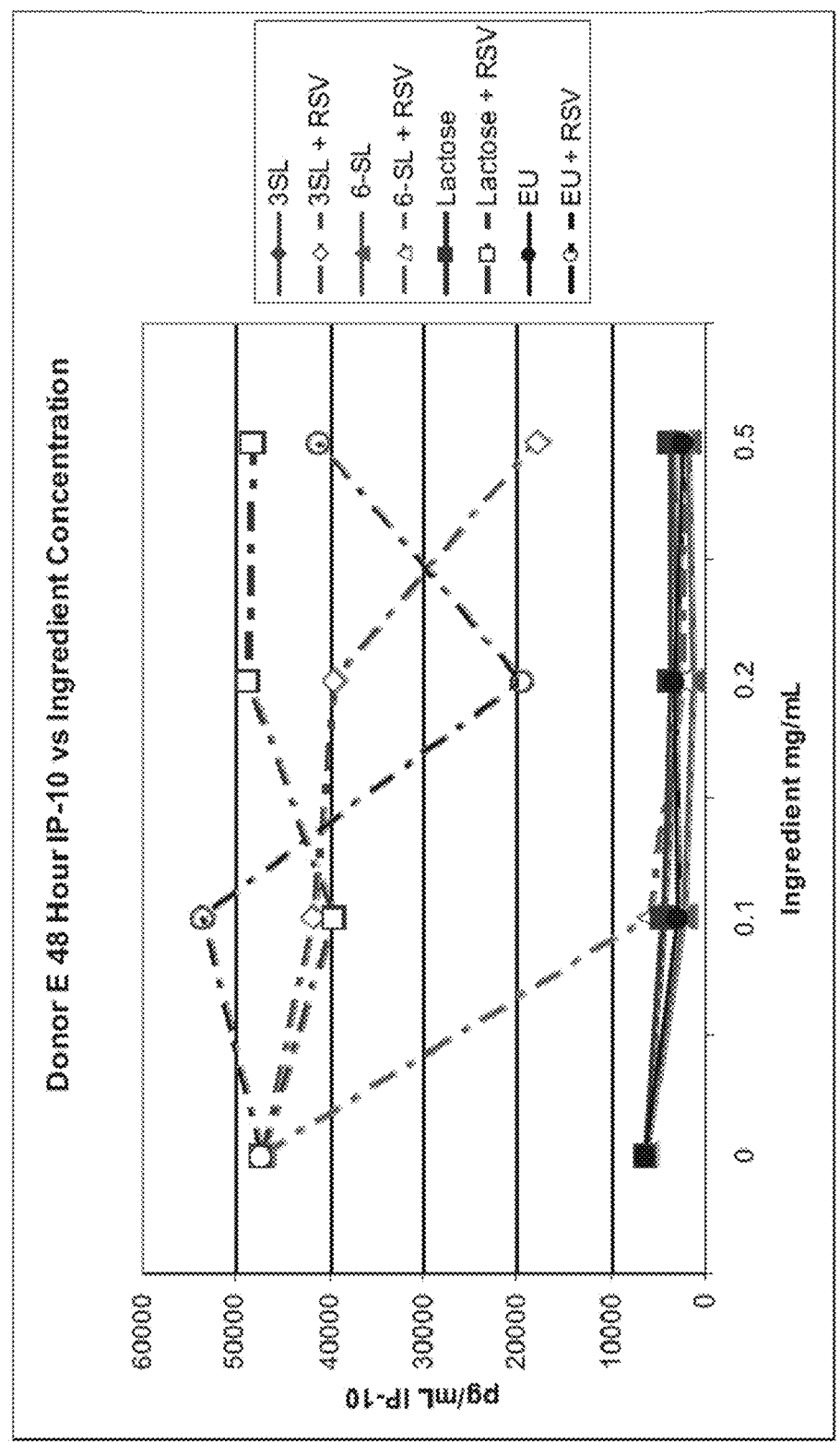
FIG. 4 is a graph depicting IP-10 levels resulting from administration of 3'SL and 6'SL as measured in Example 39.

Cytokines are measured in supernatants for each variable at 24 and 48 hours to assess the effects of HMOs on the early immune response to RSV. Cytokines are measured using custom Bio-Plex Human cytokine kits from Bio-Rad. Results for interferon-inducible protein 10 (IP-10, also known as CXCL 10) are shown in FIGS. 3 and 4 for 3'SL and 6'SL, and in FIGS. 5 and 6 for LNnT. IP-10 is a CXC chemokine that attracts, binds to and activates the CXCR3 receptor on natural killer cells and memory T cells. IP-10 is expressed by monocytes and a number of other cells, and is induced by interferon. A positive correlation exists between RSV clinical disease severity in children (as measured by: length of hospital stay, fever, and number of days supplemental $O_2$ is required) and serum IP-10. Therefore, a decrease in IP-10 signals a decrease in severity of RSV disease experienced.

IP-10 results for 3'SL and 6'SL are detailed in FIGS. 3 and 4 and show some variability in donor response, but surprisingly, 6'SL clearly down-regulates IP-10 in virus-infected variables in both donors. Note that 6'SL is able to reduce IP-10 to levels found in uninfected controls. 3'SL is not effective in Donor B, but downregulates RSV-induced IP-10 in Donor E. These data show both 3'SL and 6'SL dampen RSV-induced IP-10, but that 6'SL is more effective at downregulation of IP-10. Results also suggest that levels below 0.1 mg/mL of 6'SL as well as levels greater than 0.5 mg/mL may be effective at reducing IP-10 in some individuals.

Figure 5:
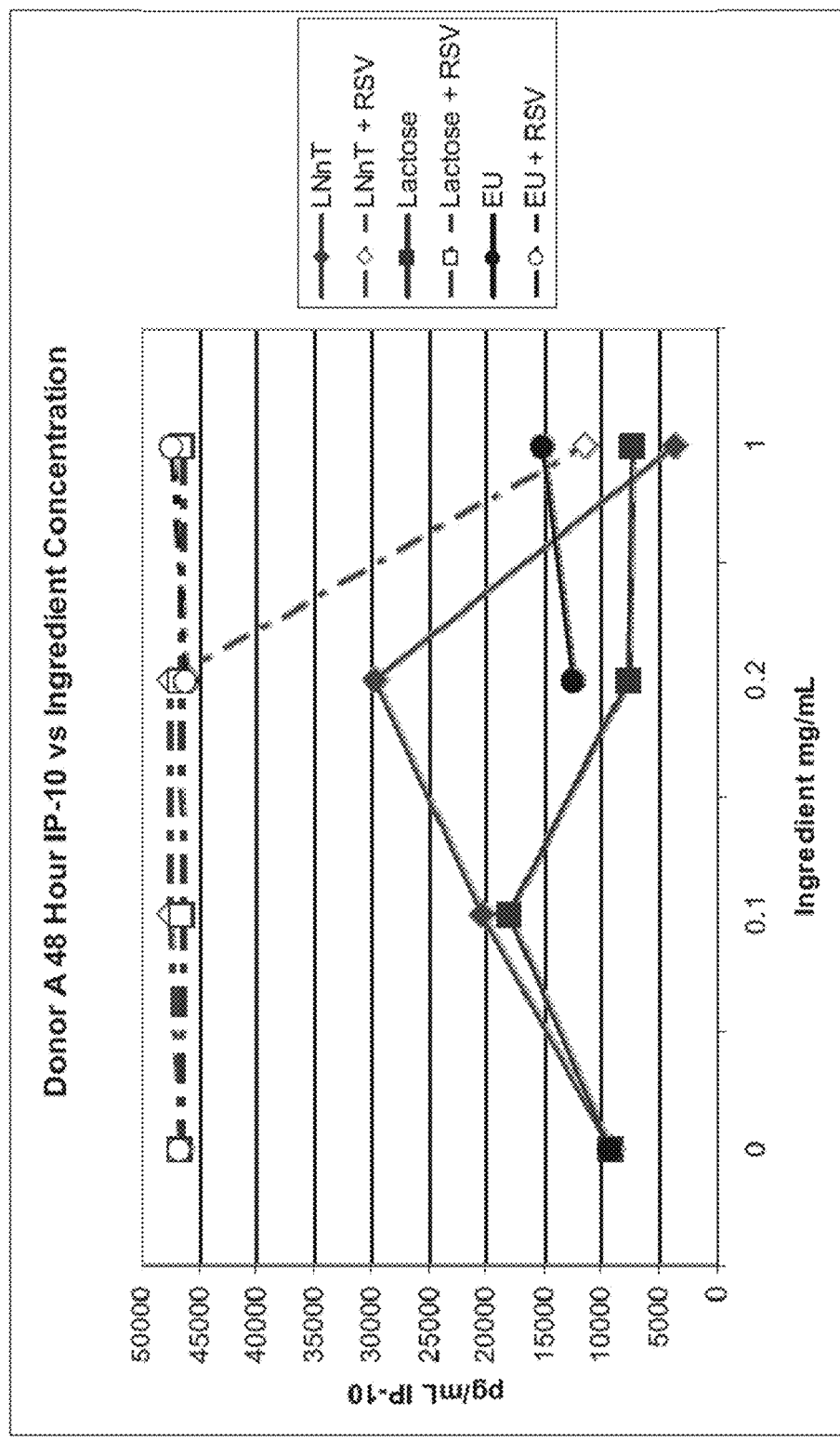
FIG. 5 is a graph depicting IP-10 levels resulting from administration of LNnT as measured in Example 39.
Figure 6:
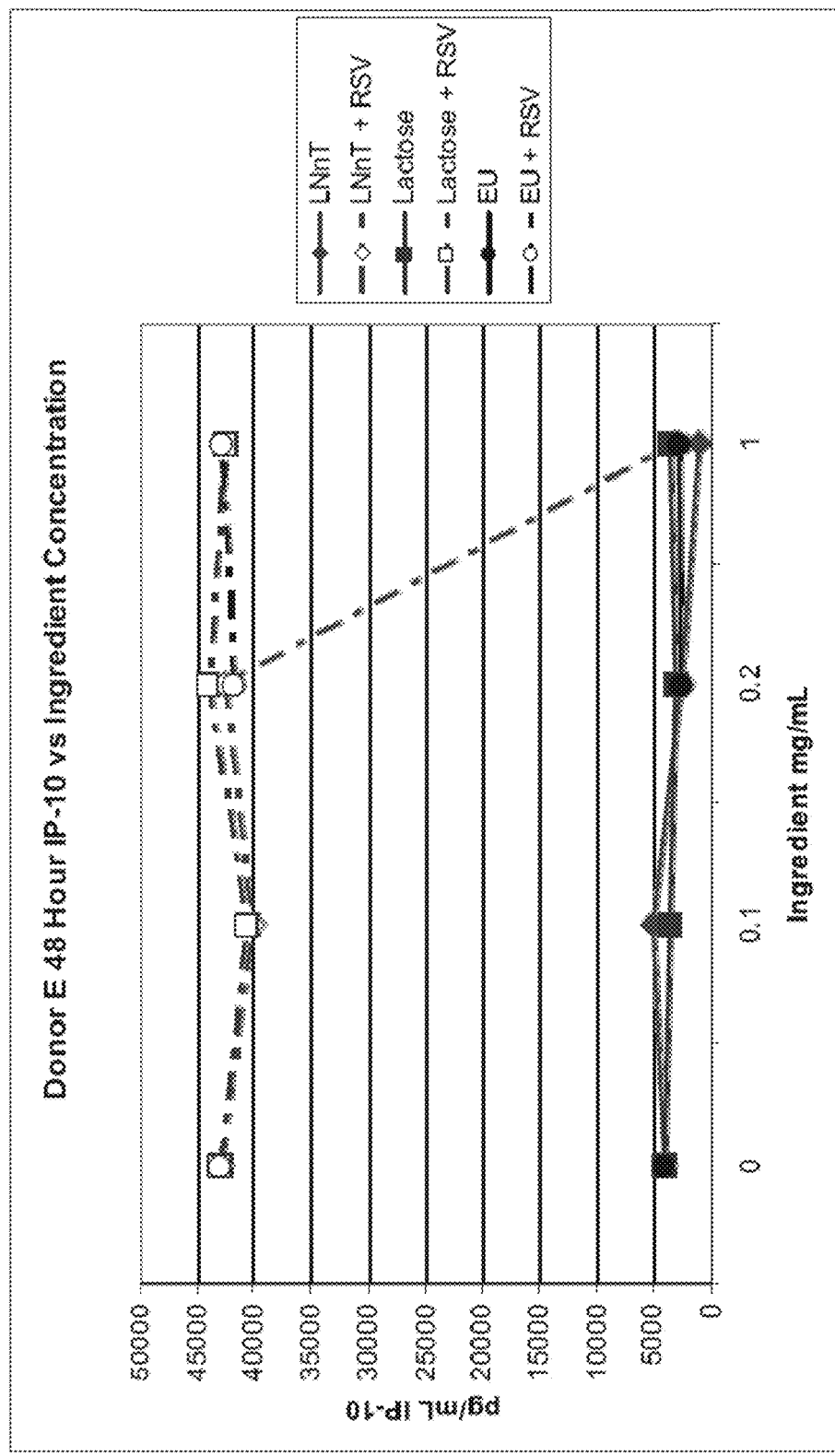
FIG. 6 is a graph depicting IP-10 levels resulting from administration of LNnT as measured in Example 39.

IP-10 results for LNnT are detailed in FIGS. 5 and 6 and show some variability in donor response, but surprisingly, LNnT clearly downregulates IP-10 in virus-infected variables in both donors. Note that LNnT is able to reduce IP-10 to levels found in uninfected controls. Results also suggest that levels between 0.2 and 1 mg LNnT/mL as well as greater than 1 mg/mL may be effective at reducing IP-10 in some individuals. Inclusion of matched endotoxin unit concentration controls clearly indicates that the decrease in IP-10 is not due to the presence of very low levels of endotoxin in the LNnT.

Figure 7:
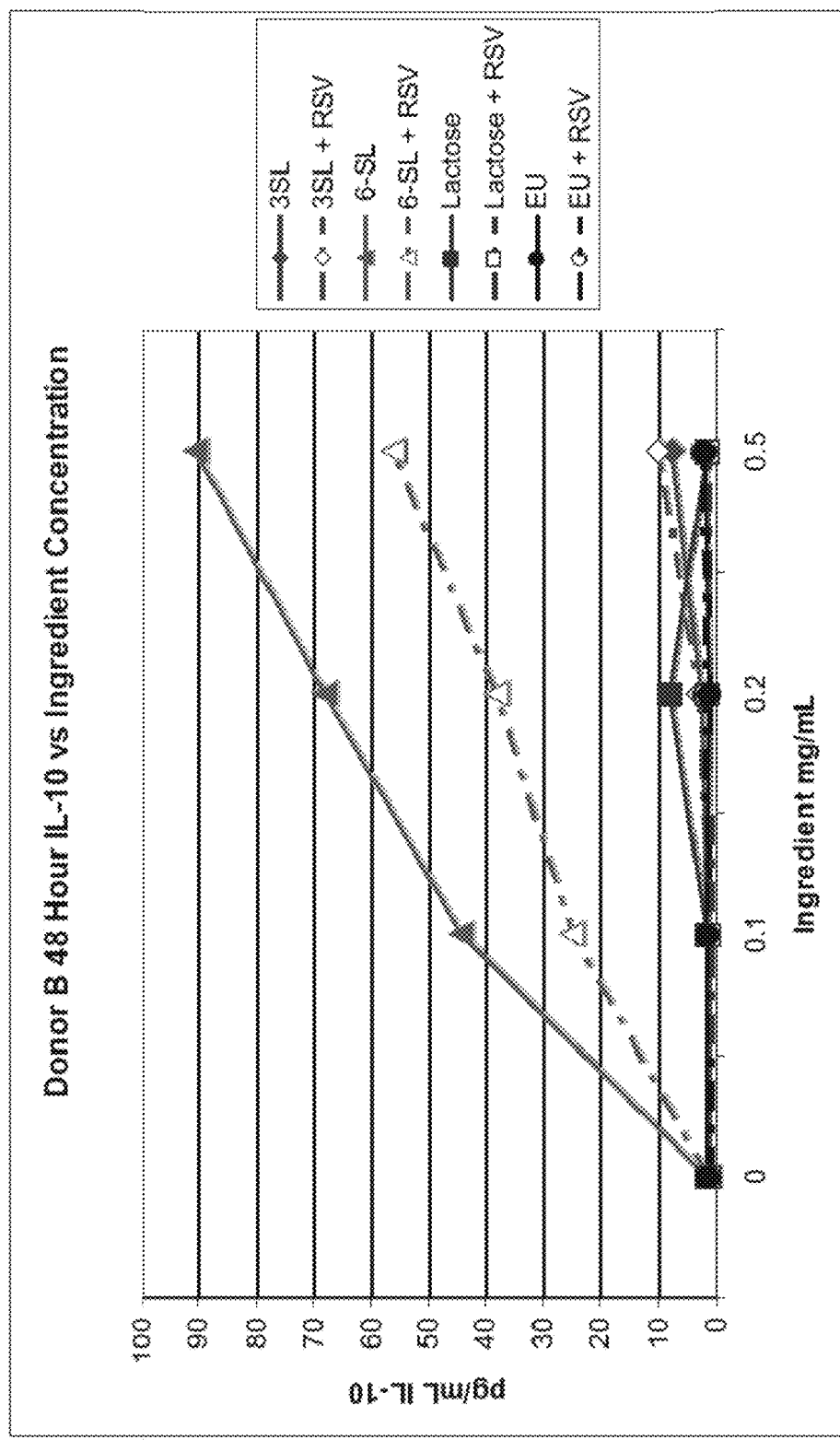
FIG. 7 is a graph depicting IL-10 levels resulting from administration of 3'SL and 6'SL as measured in Example 39.
Figure 8:
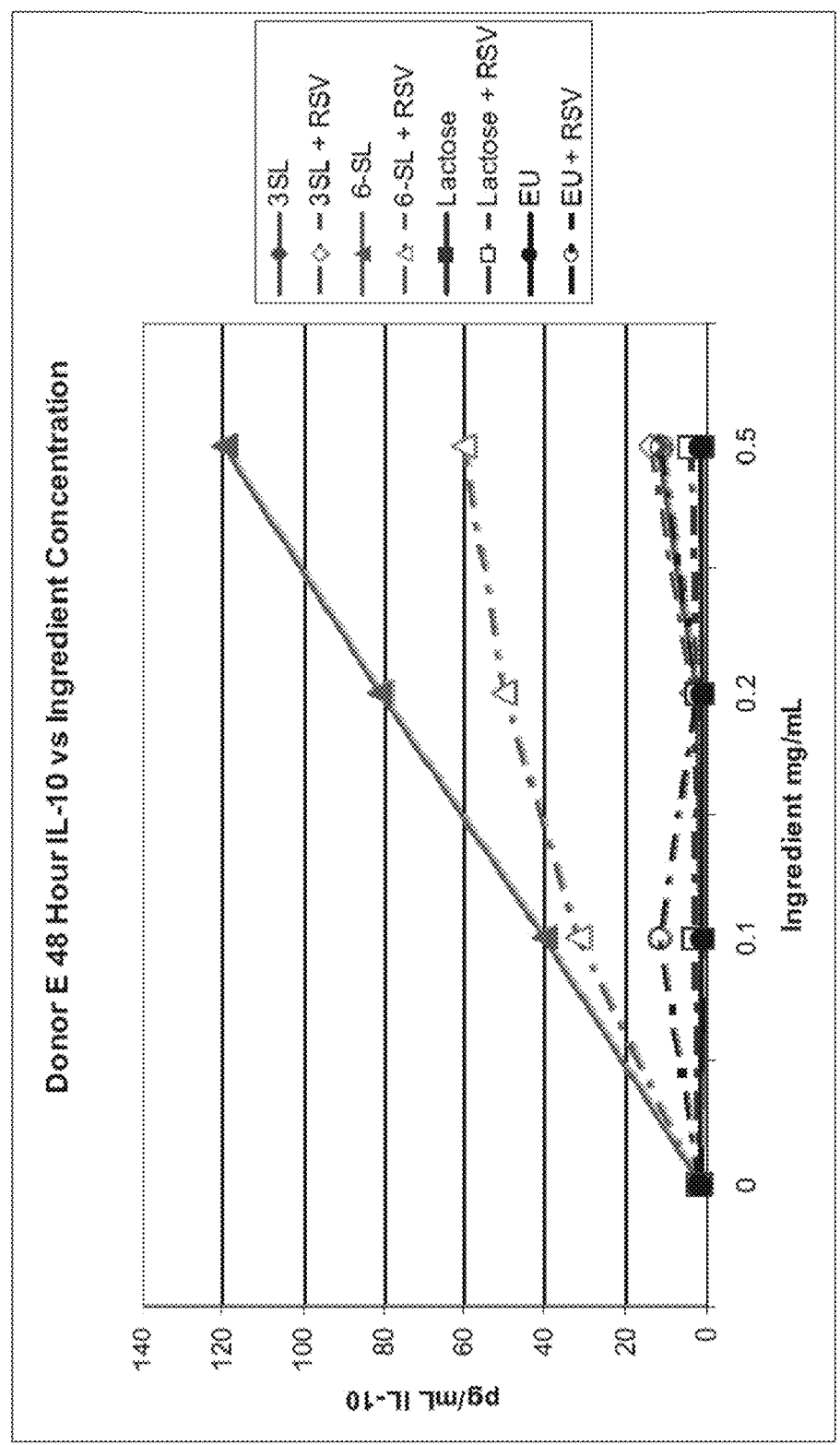
FIG. 8 is a graph depicting IL-10 levels resulting from administration of 3'SL and 6'SL as measured in Example 39.
Figure 9:
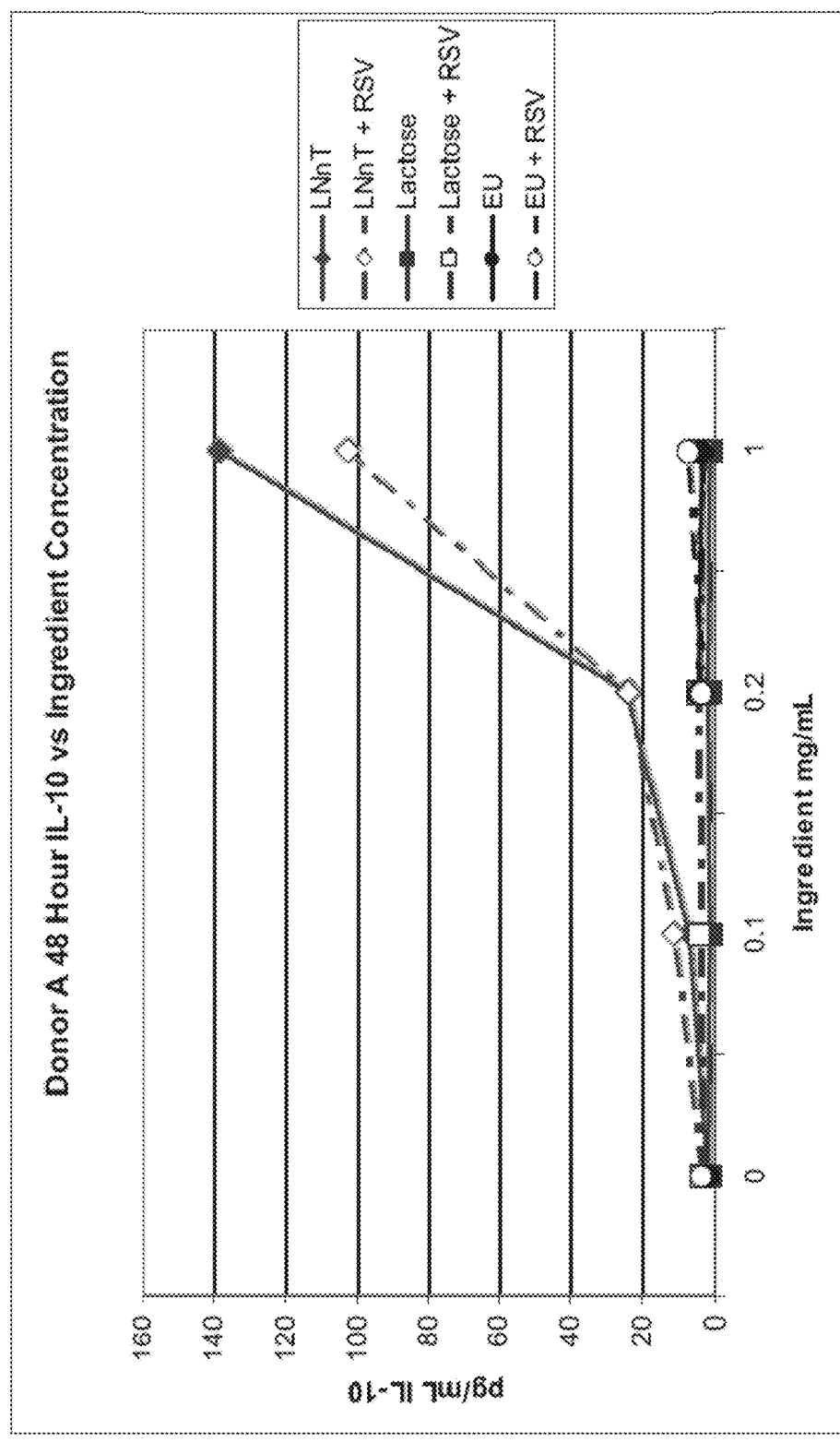
FIG. 9 is a graph depicting IL-10 levels resulting from administration of LNnT as measured in Example 39.
Figure 10:
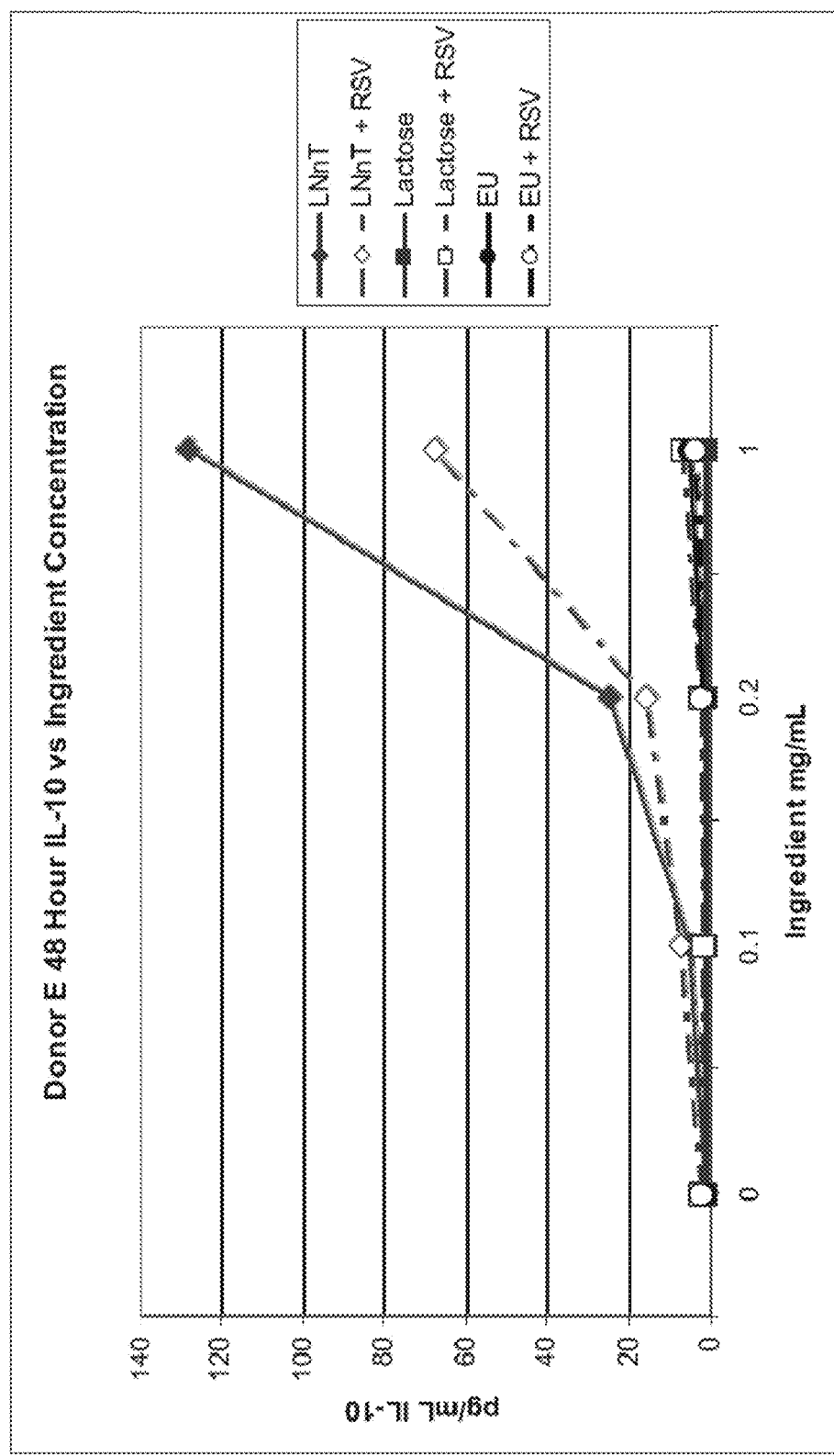
FIG. 10 is a graph depicting IL-10 levels resulting from administration of LNnT as measured in Example 39.

In FIGS. 7 and 8, cytokine results also surprisingly show 6'SL increases interleukin 10 (IL-10) concentration in a dose-dependent manner in the presence or absence of RSV. IL-10 results for LNnT are shown in FIGS. 9 and 10. Surprisingly, LNnT increases IL-10 concentration in a dose-dependent manner in the presence or absence of RSV. IL-10 is produced by activated CD8+ T-cells, by CD4+ T-cells after both antigen-specific and polyclonal activation, and by monocytes following cell activation by bacterial lipopolysaccharides. Inclusion of matched endotoxin unit concentration controls clearly differentiates that the increase in IL-10 is not due to the presence of very low levels of endotoxin in the 6'SL or the LNnT.

Surprisingly, it is found that pretreatment for 24 hours by 6'SL, 3'SL, or LNnT is effective in reducing inflammation caused by RSV. Moreover, 6'SL and LNnT are shown to be more effective than 3'SL at dampening virus-induced inflammation as measured by a decrease in IP-10. Further, it is shown that 6'SL is immunomodulatory in the absence of the virus, as the inclusion of 6'SL induces and/or modifies the production of monocyte-derived cytokines such as IL-10, MIP-1β, Interferon-γ, IL-8, IL-1α, IL-1β, and IL-1ra. Surprisingly, 3'SL is also immunomodulatory in the presence or absence of the virus, as the inclusion of 3'SL induces and/or modifies the production of monocyte-derived cytokines such as MIP-1β, Interferon-γ, IL-8, and IL-1ra. Surprisingly, LNnT is also immunomodulatory in the presence or absence of the virus, as the inclusion of LNnT induces and/or modifies the production of monocyte-derived cytokines such as IL-10, MIP-1β, Interferon-γ, IL-8, IL-1α, IL-1β, and IL-1ra.

Example 40

In this example, the ability of the combination of 2'FL and lycopene to reduce viral replication in vitro is demonstrated.

Specifically, on Day −1, Calu3 monolayers are seeded in sufficient numbers to reach 95-100% confluence in 24 well plates by Day 0. On day 0, 2'FL alone at a concentration of 0.1 μg/mL, 1 μg/mL, or 10 μg/mL or in combination with lycopene at a concentration of 0.5 μg/mL, 1 μg/mL, or 5 μg/mL or tetrahydrofuran (THF) at a concentration of 0.5 μg/mL, 1 μg/mL, or 5 μg/mL are added and incubated for approximately 24 hours at 37° C. in 5% $CO_2$. THF is a solvent used to solubilize the lycopene, and as such, is a control included to differentiate solvent effects. On day 1, the cell supernatants are removed and the monolayers are incubated with medium alone or medium plus Respiratory Syncytial Virus (RSV) for approximately 1 hour at 37° C. in 5% $CO_2$ at a multiplicity of infection (MOI) of 1. After approximately 1 hour, fresh medium alone or containing the appropriate concentrations of 2'FL and lycopene or 2'FL and THF is added to the appropriate wells, and the cells are incubated for 48 hours at 37° C. in 5% $CO_2$. On day 3, supernatants and cell lysates are collected separately, aliquotted and stored frozen at −70° C. for later analysis. Cell lysates are analyzed by TaqMan qRTPCR to assess viral replication through measurement of RSV NS1 copy numbers.

Figure 11:
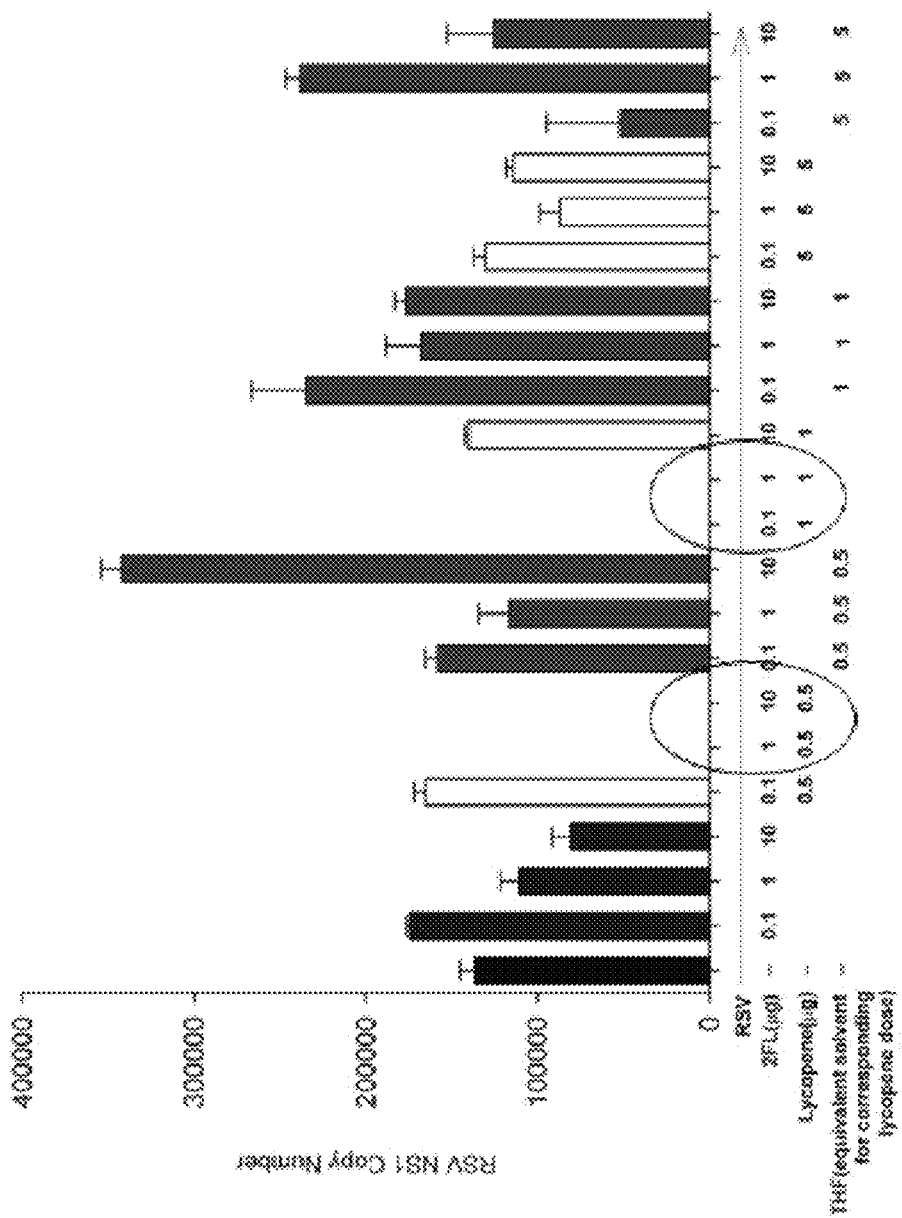
FIG. 11 is a graph depicting RSV NS1 copy levels resulting from administration of 2'FL and/or lycopene as measured in Example 40.

As shown in FIG. 11, the combination of 2'FL and lycopene at certain combinations (1 µg and 10 µg of 2'FL in combination with 0.5 µg lycopene; and 0.1 µg and 1 µg of 2'FL in combination with 1 µg lycopene) shows a synergistic effect that results in a dramatic inhibition of viral load as measured by copies of RSV NS1. Further, as can be seen in FIG. 11, 2'FL alone shows a modest concentration dependent decrease in RSV NS1. Surprisingly, the combination of 2'FL and lycopene at select concentrations can substantially inhibit RSV replication in vitro.

Example 41

In this example, the ability of the combination of 2'FL and lycopene to reduce IP-10, a marker of viral inflammation, in vitro is demonstrated.

Specifically, 2'FL at a concentration of 0.1 mg/mL, 0.2 mg/mL, or 1 mg/mL in combination with lycopene at a concentration of 0.5 µg/mL, 1.0 µg/mL, or 5.0 µg/mL or Tetrahydrofuran (THF) at a concentration of 0.5 µg/mL, 1.0 µg/mL, or 5.0 µg/mL is added to fresh human peripheral blood mononuclear cells (PBMCs) and incubated at 37° C. in 5% $CO_2$ to pretreat the cells for approximately 24 hours. THF is a solvent used to solubilize the lycopene, and as such, is a control included to differentiate solvent effects. After approximately 24 hours, some variables are then incubated with RSV at a multiplicity of infection (MOI) of 1 for approximately 1 hour at 37° C. in 5% in $CO_2$. The uninfected control variable is incubated with medium for approximately 1 hour at 37° C. in 5% $CO_2$. After approximately 1 hour, fresh medium alone or containing the appropriate concentrations of 2'FL and lycopene or 2'FL and THF is added to the appropriate variables, and the PBMCs are incubated for 48 hours at 37° C. in 5% $CO_2$. Supernatants are collected at 48 hours post-infection. Cytokines are measured in supernatants for each variable at 48 hours using Luminex human cytokine kits to assess the effects of HMOs on the early immune response to RSV.

Interferon-inducible Protein 10 (IP-10, also known as CXCL10) is a CXC chemokine that attracts, binds to and activates the CXCR3 receptor on Natural Killer Cells and Memory T cells. IP-10 is expressed by monocytes and a number of other cells, and is induced by interferon. A positive correlation exists between RSV clinical disease severity in children (as measured by: length of hospital stay, fever, and number of days supplemental $O_2$ was required) and serum IP-10. Therefore, a decrease in IP-10 may signal a decrease in severity of RSV disease experienced.

Figure 12:
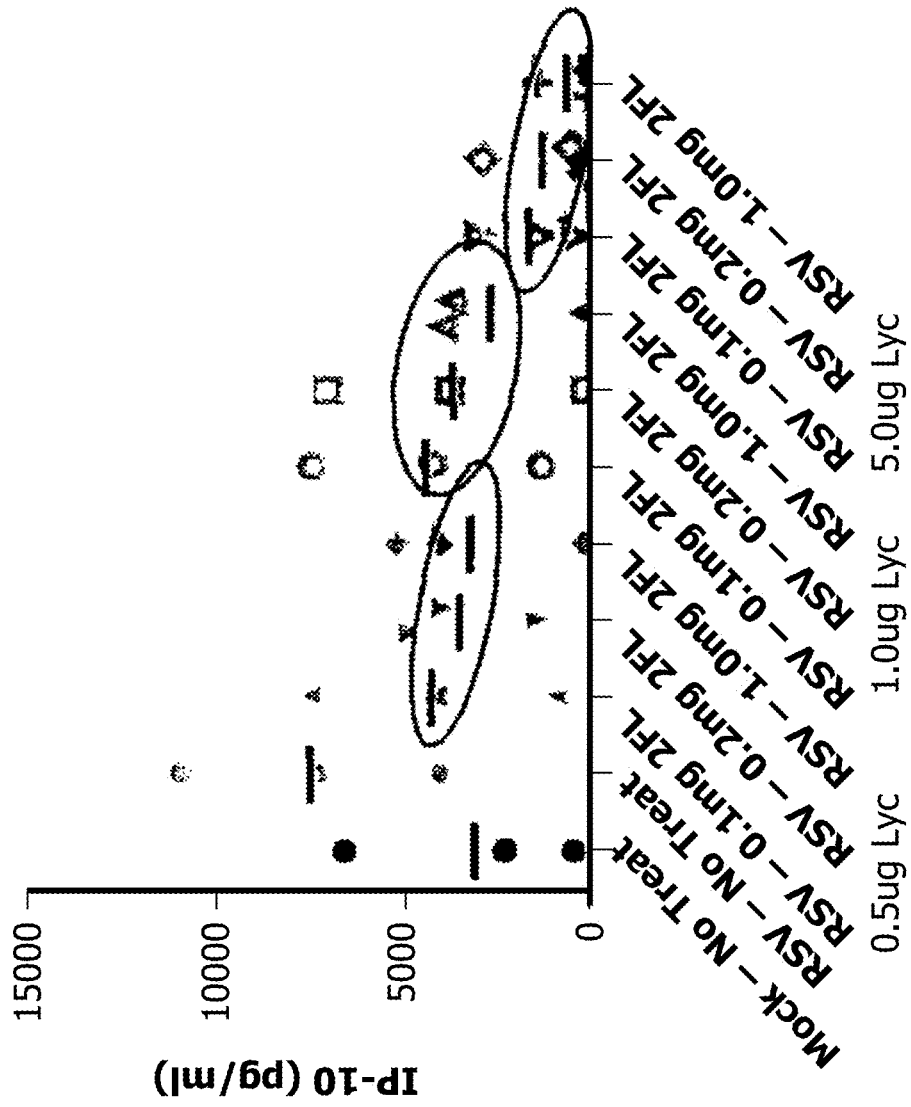
FIG. 12 is a graph depicting IP-10 levels resulting from administration of 2'FL and lycopene as measured in Example 41.

Surprisingly, as shown in FIG. 12, the combination of 2'FL and lycopene result in a stepwise concentration dependent downregulation of IP-10. Although effects are evident with 2'FL at the lower lycopene concentrations, the strongest decrease in IP-10 is seen for 2'FL at concentrations of 0.1 mg/mL, 0.2 mg/mL, or 1 mg/mL in combination with the highest lycopene concentration tested of 5.0 µg/mL tested. As such, it can be concluded that the combination of 2'FL and lycopene can decrease the severity of RSV disease experienced, especially at a lycopene concentration of 5.0 µg/mL.

Example 42

In this example, the abilities of 2'FL, LNnT and 3'SL to reduce or inhibit respiratory syncytial virus replication in lung epithelial cells in vitro are demonstrated.

Specifically, on Day −1, 16HBE cell monolayers are seeded in sufficient numbers to reach 95-100% confluence in 24 well places by Day 0. On day 0, either 2'FL (in concentrations of 1 µg/mL, 5 µg/mL, 10 µg/mL, 50 µg/mL, 100 µg/mL, 500 µg/mL, and 1000 µg/mL), LNnT (in concentrations of 10 µg/mL, 100 µg/mL, or 1000 µg/mL), or 3'SL (in concentrations of 5 µg/mL, 10 µg/mL, 50 µg/mL, 100 µg/mL, 500 µg/mL, and 1000 µg/mL) is added and incubated for approximately 24 hours at 37° C. in 5% $CO_2$. On day 1, the cell supernatants are removed and the monolayers are incubated with medium alone or medium plus Respiratory Syncytial Virus (RSV) for approximately 1 hour at 37° C. in 5% $CO_2$ at a multiplicity of infection (MOI) of 1. After approximately 1 hour, fresh medium alone or containing the appropriate concentrations of 2'FL 3'SL, or LNnT is added to the appropriate wells, and the cells are incubated for 48 hours at 37° C. in 5% $CO_2$. On day 3, supernatants and cell lysates are collected separately, aliquotted and stored frozen at −70° C. for later analysis. Cell lysates are analyzed by TaqMan qRTPCR to assess viral replication through measurement of RSV NS1 copy numbers.

Figure 13:
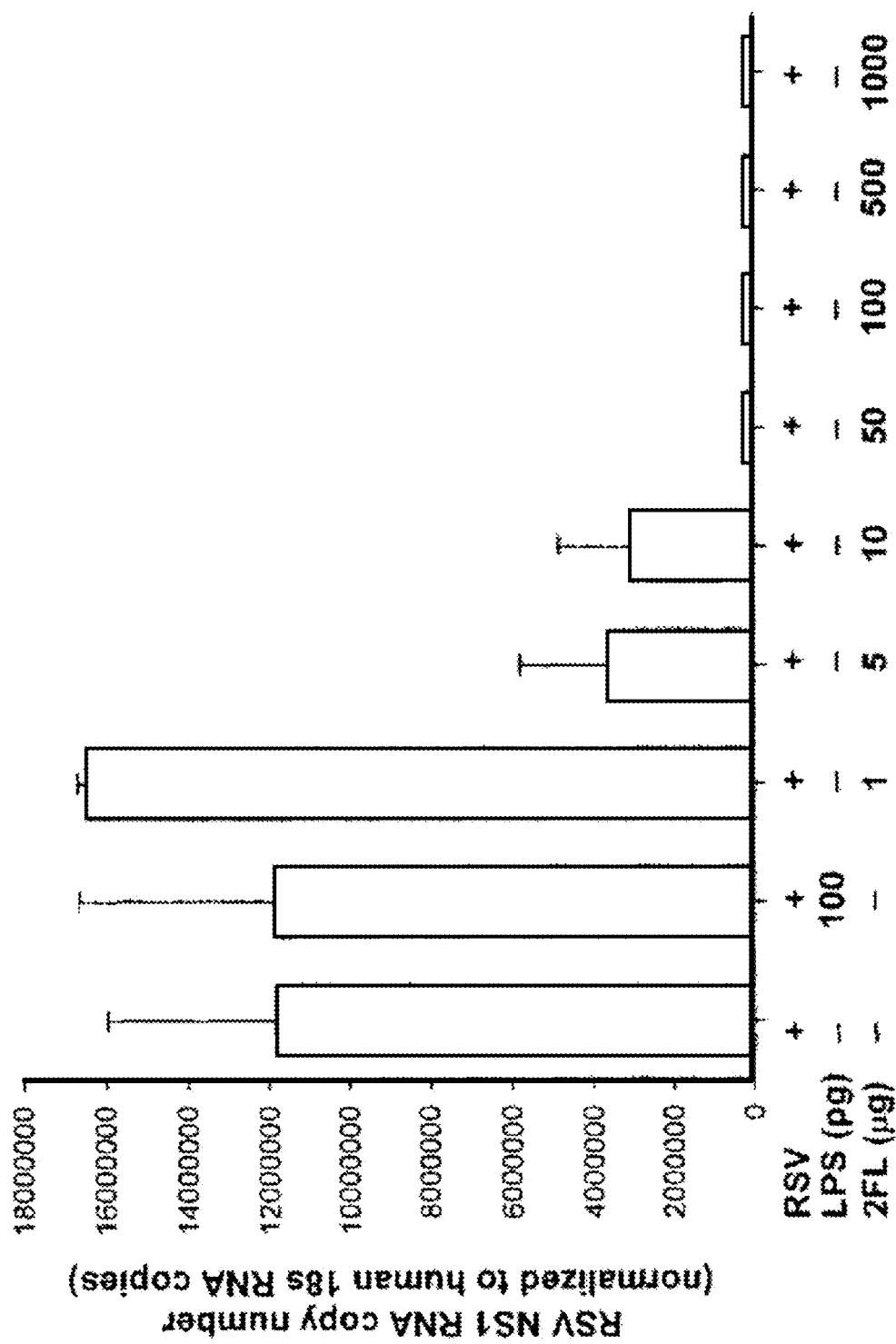
FIG. 13 is a graph depicting the RSV NS1 copy levels resulting from administration of 2'FL as measured in Example 42.
Figure 14:
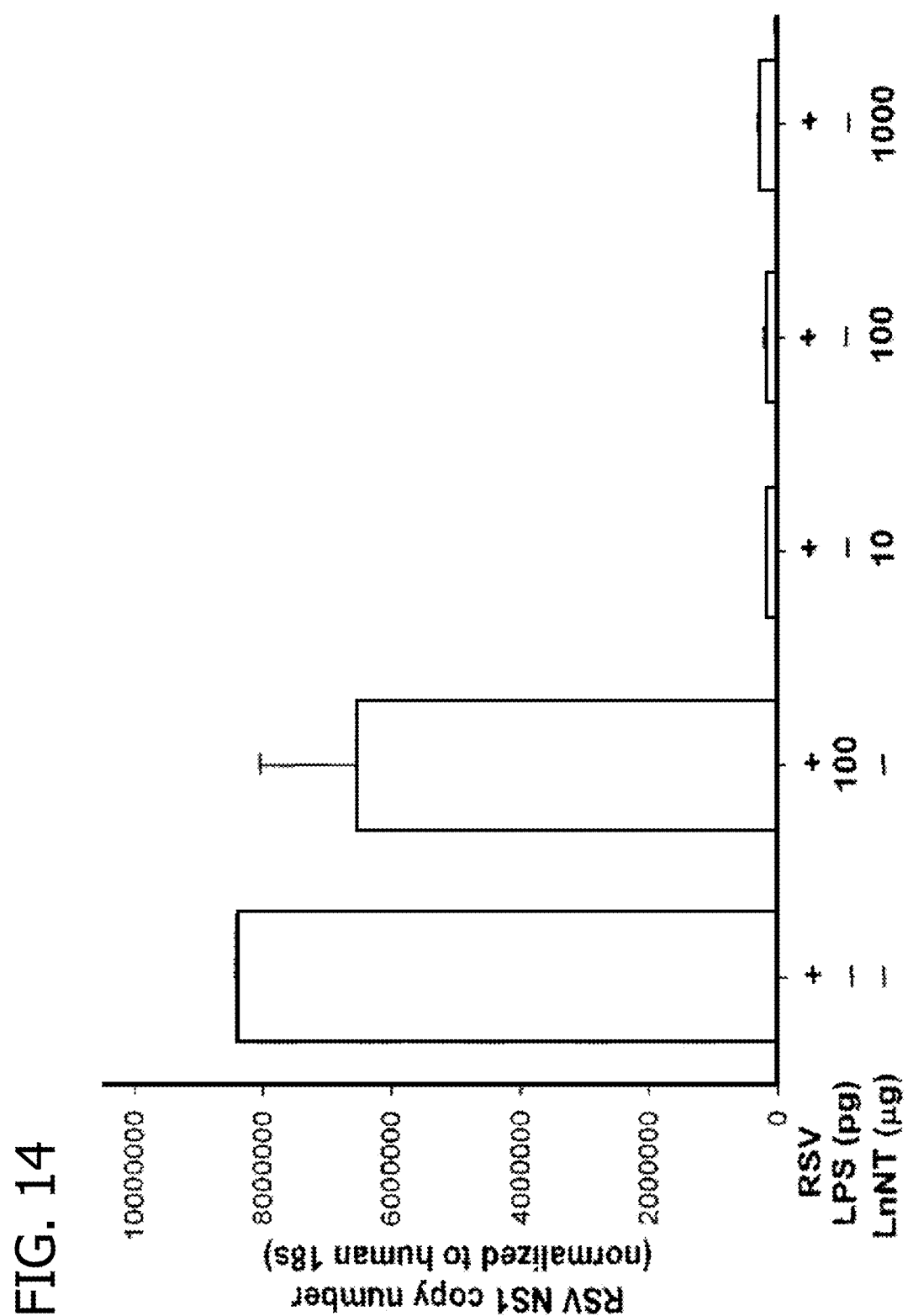
FIG. 14 is a graph depicting the RSV NS1 copy levels resulting from administration of LNnT as measured in Example 42.
Figure 15:
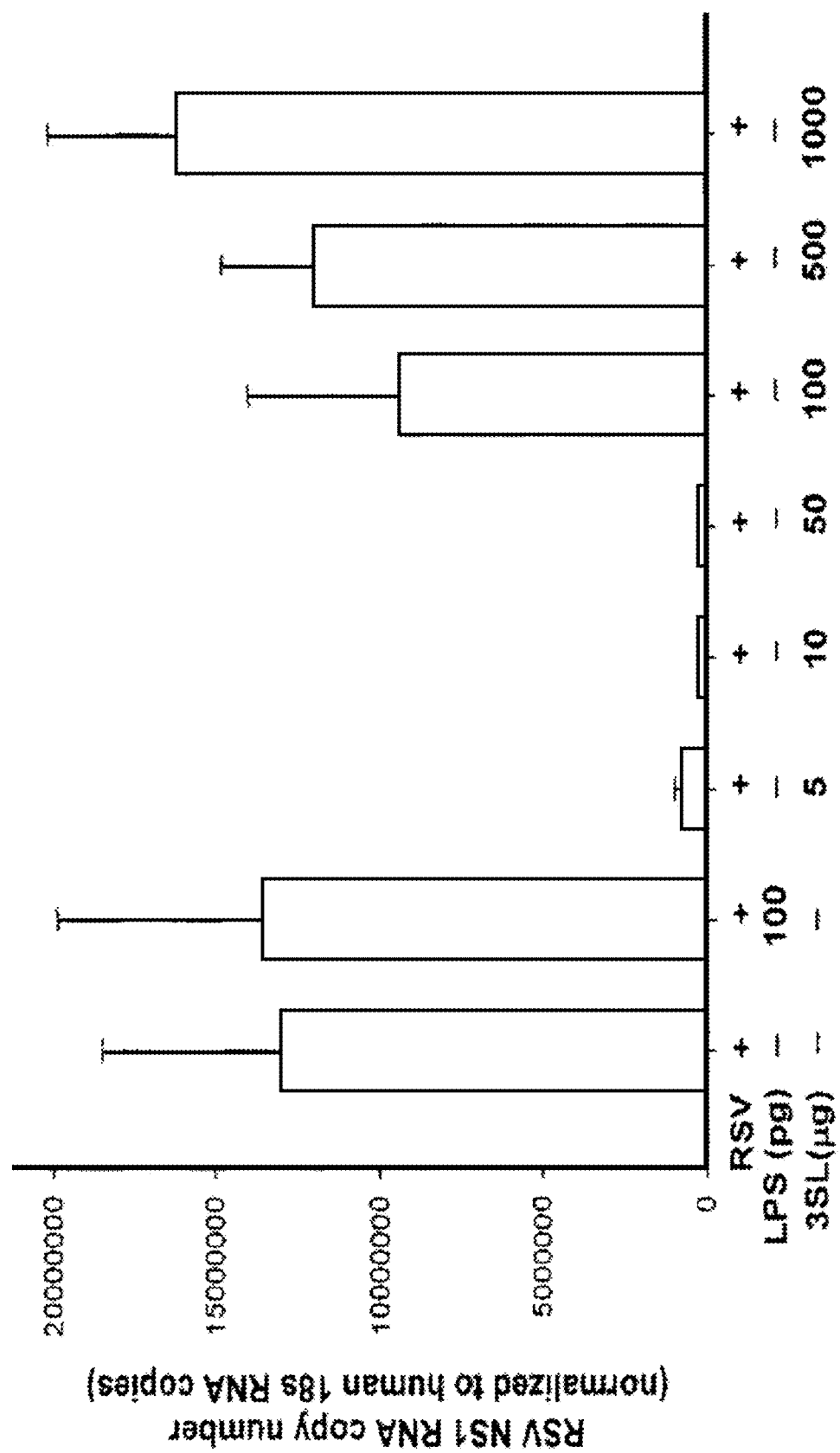
FIG. 15 is a graph depicting the RSV NS1 copy levels resulting from administration of 3'SL as measured in Example 42.

Results for 2'FL are shown in FIG. 13. Surprisingly, concentrations at or above 5 µg 2'FL/mL decrease viral load or inhibit RSV replication in 16HBE lung epithelial cells as reflected by the sharp reduction in RSV NS1 copies. Results for LNnT are shown in FIG. 14. Surprisingly, concentrations at or above 10 µg LNnT/mL decrease viral load or inhibit RSV replication in 16HBE lung epithelial cells as reflected by the sharp reduction in RSV NS1 copies. Results for 3'SL are shown in FIG. 15. Surprisingly, only concentrations of 3'SL between 5 and 50 µg 3'SL/mL decease viral load or inhibit RSV replication. Reduction of viral load or inhibition of virus replication, such as by 2'FL, LNnT, or 3'SL as shown FIGS. 13-15, may translate to a decrease in disease severity and symptoms. As such, it can be concluded that 2'FL, LNnT, and 3'SL support respiratory health by improving airway defense mechanisms against respiratory syncytial virus.

Example 43

In this example, the abilities of LNnT and 6'SL to reduce or inhibit H1N1 influenza A virus replication in lung epithelial cells in vitro are demonstrated.

Specifically, on Day −1, 16HBE or Calu3 epithelial cell monolayers are seeded in sufficient numbers to reach 95-100% confluence in 24 well plates by Day 0. On day 0, either LNnT (at concentrations of 0.1 µg/mL, 0.5 µg/mL, 1.0 µg/mL, 5.0 µg/mL, 10 µg/mL, 50 µg/mL, 100 µg/mL, 500 µg/mL, 1000 µg/mL, and 2000 µg/mL), or 6'SL (10 µg/mL, 100 µg/mL, and 1000 µg/mL) is added and incubated for approximately 24 hours at 37° C. in 5% $CO_2$. On day 1, the cell supernatants are removed and the monolayers are incubated with medium alone or medium plus H1N1 influenza A virus (IAV) for approximately 1 hour at 37° C. in 5% $CO_2$ at a multiplicity of infection (MOI) of 0.01. After approximately 1 hour, fresh medium alone or containing the appropriate concentrations of LNnT or 6'SL is added to the appropriate wells, and the cells are incubated for 48 hours at 37° C. in 5% $CO_2$. On day 3, supernatants and cell lysates are collected separately, aliquotted and stored frozen at −70° C. for later analysis. Cell lysates are analyzed by TaqMan qRTPCR to assess viral replication through measurement of IAV M gene copy numbers.

Figure 16:
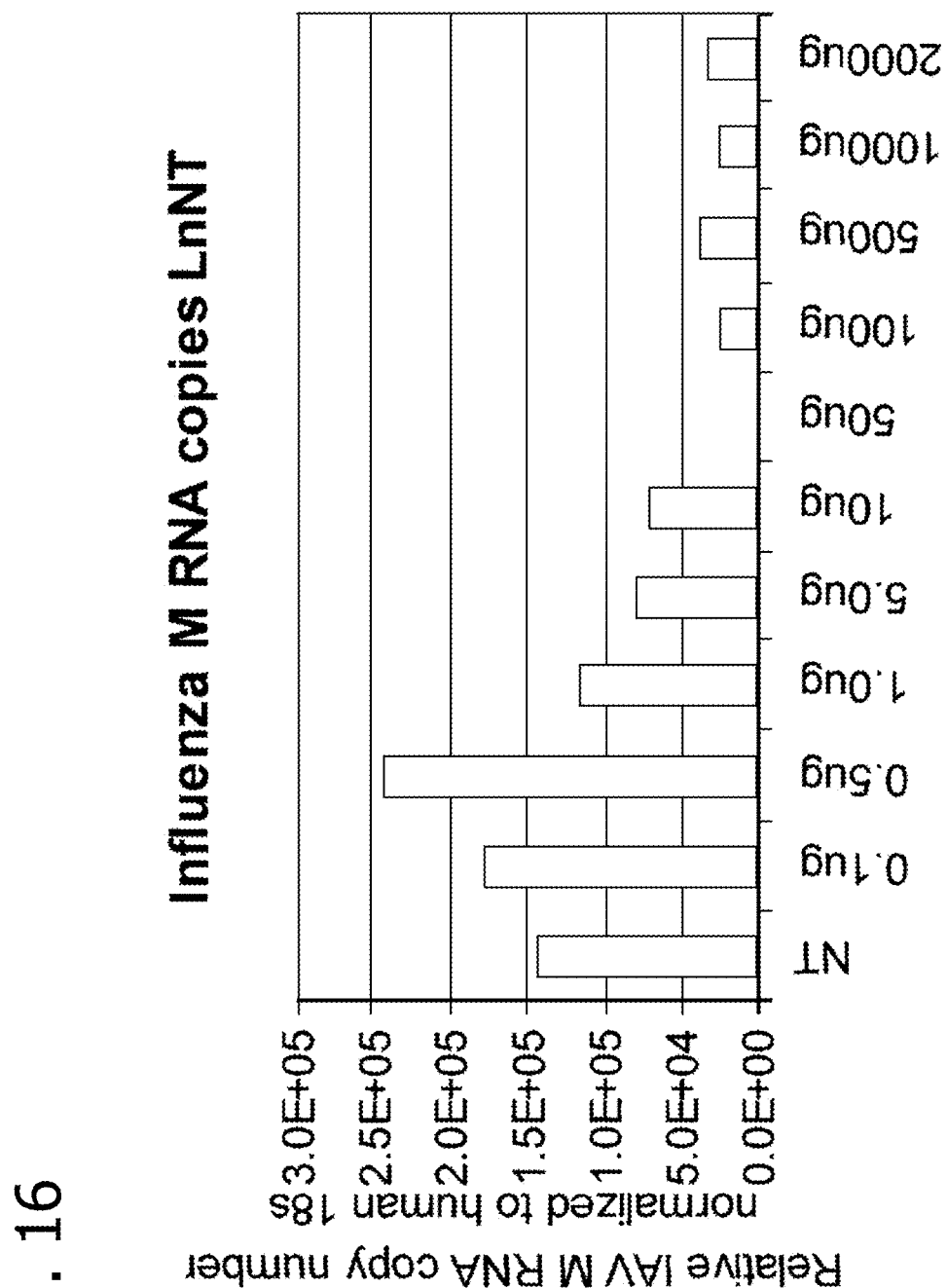
FIG. 16 is a graph depicting the IAV M gene copy levels resulting from administration of LNnT as measured in Example 43.
Figure 17:
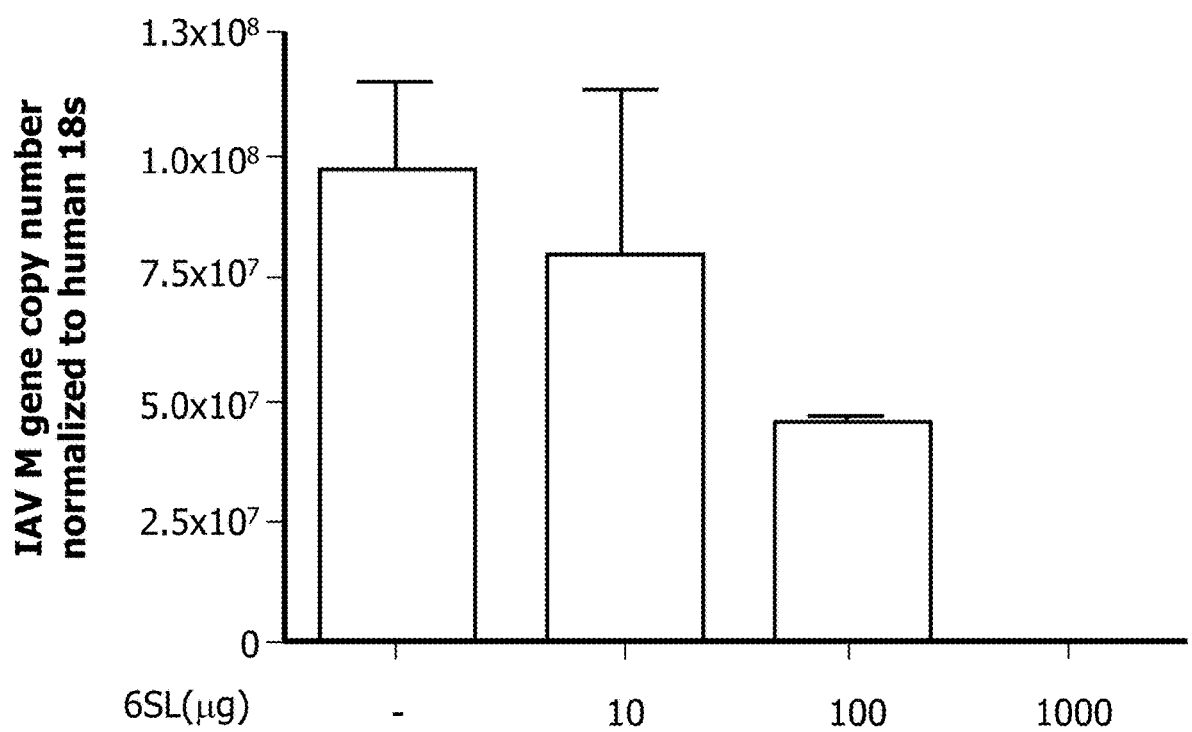
FIG. 17 is a graph depicting the IAV M gene copy levels resulting from administration of 6'SL as measured in Example 43.

Results for LNnT are shown in FIG. 16. Surprisingly, concentrations at or above 1 µg LNnT/mL decrease viral load or inhibit IAV replication in 16HBE lung epithelial cells as reflected by the sharp reduction in IAV M gene copies. Results for 6'SL are shown in FIG. 17. Surprisingly, concentrations at or above 10 μg 6'SL/mL decrease viral load or inhibit IAV replication in Calu3 lung epithelial cells as reflected by the sharp reduction in IAV M gene copies. Reduction of viral load or inhibition of virus replication may translate to a decrease in disease severity and symptoms. As such, it can be concluded that LNnT and 6'SL can support respiratory health by improving airway defense mechanisms against influenza.

Example 44

In this example, the ability of 6'SL to reduce the inflammatory cytokine IP-10 in vitro is demonstrated.

Specifically, 6'SL was added individually at concentrations of 0.1 mg/mL, 0.2 mg/mL, 0.5 mg/mL or 1.0 mg/mL to fresh peripheral blood mononuclear cells (PCMBs) and incubated at 37° C. in 5% $CO_2$ to pretreat the cells for approximately 24 hours. After approximately 24 hours, some variables are then incubated with RSV at a multiplicity of infection (MOI) of 1.0 for approximately 1 hour at 37° C. in 5% in $CO_2$. Uninfected control variables are incubated with medium for approximately 1 hour at 37° C. in 5% $CO_2$. After approximately 1 hour, fresh medium alone or containing the appropriate concentrations of 6'SL is added to the appropriate variables, and the PBMCs are incubated for 48 hours at 37° C. in 5% $CO_2$. Supernatants are collected at 48 hours post-infection. Cytokines are measured in supernatants for each variable at 48 hours to assess the effects of HMOs on the early immune response to RSV.

Interferon-inducible Protein 10 (IP-10, also known as CXCL10) is a CXC chemokine that attracts, binds to and activates the CXCR3 receptor on Natural Killer Cells and Memory T cells. IP-10 is expressed by monocytes and a number of other cells, and is induced by interferon. A positive correlation exists between RSV clinical disease severity in children (as measured by: length of hospital stay, fever, and number of days supplemental $O_2$ was required) and serum IP-10. Therefore, a decrease in IP-10 may signal a decrease in severity of RSV disease experienced.

Figure 18:
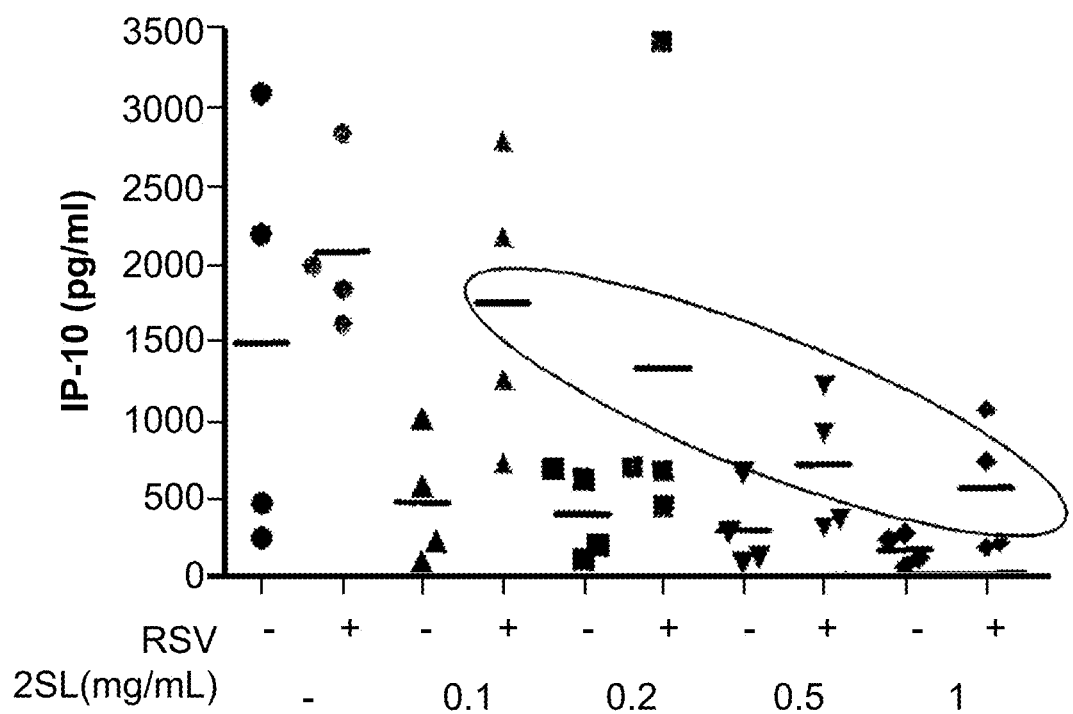
FIG. 18 is a graph depicting the IP-10 levels resulting from administration of 6'SL as measured in Example 44.

Surprisingly, as shown in FIG. 18, 6'SL (at concentrations of from 0.1 mg/mL to 1 mg/mL) demonstrates a dose-dependent downregulation of IP-10 in RSV infected PBMCs from 4 donors. As 6'SL concentration increases, there is a decrease in IP-10 in the RSV infected PBMCs. As such, it can be concluded that the administration of 6'SL may decrease the severity of RSV disease experienced.

Example 45

In this example, 6'SL (alone or in combination with 3'SL) and LNnT demonstrate a dose-dependent increase in the anti-inflammatory cytokine IL-10 in the presence or absence of RSV in peripheral blood mononuclear cells (PBMCs) in vitro.

Specifically, 3'SL and 6'SL are added individually at concentrations of 0.1 mg/mL, 0.2 mg/mL, or 0.5 mg/mL or in combination (Combo 1=1 part 3'SL to 1 part 6'SL; and Combo 2=1 part 3'SL to 2 parts 6'SL), at total concentrations of 0.2 mg/mL, 0.4 mg/mL, or 1.0 mg/mL to fresh PBMCs and incubated at 37° C. in 5% $CO_2$ to pretreat the cells for approximately 24 hours. In a separate experiment, LNnT and 2'FL are added individually at concentrations of 0.1 mg/mL, 0.2 mg/mL, 1.0 mg/mL or 2.0 mg/mL to fresh PBMCs and incubated at 37° C. in 5% $CO_2$ to pretreat the cells for approximately 24 hours. Lactose is included as a carbohydrate control. Matched endotoxin unit concentration controls are included to allow differentiation of ingredient effects from inherent low levels of endotoxin. After approximately 24 hours, some variables are then incubated with RSV at a multiplicity of infection (MOI) of 0.1 for approximately 1 hour at 37° C. in 5% in $CO_2$. Uninfected control variables are incubated with medium for approximately 1 hour at 37° C. in 5% $CO_2$. After approximately 1 hour, fresh medium alone or containing the appropriate concentrations of LNnT alone, 2'FL alone, 3'SL or 6'SL individually or in combination, lactose alone, or endotoxin alone is added to the appropriate variables, and the PBMCs were incubated for 48 hours at 37° C. in 5% CO2. Supernatants are collected at 24 and 48 hours post-infection. Cytokines are measured in supernatants for each variable at 24 and 48 hours to assess the effects of HMOs on the early immune response to RSV. Cytokines are measured using custom Bio-Plex Human cytokine kits from Bio-Rad.

Figure 19A:
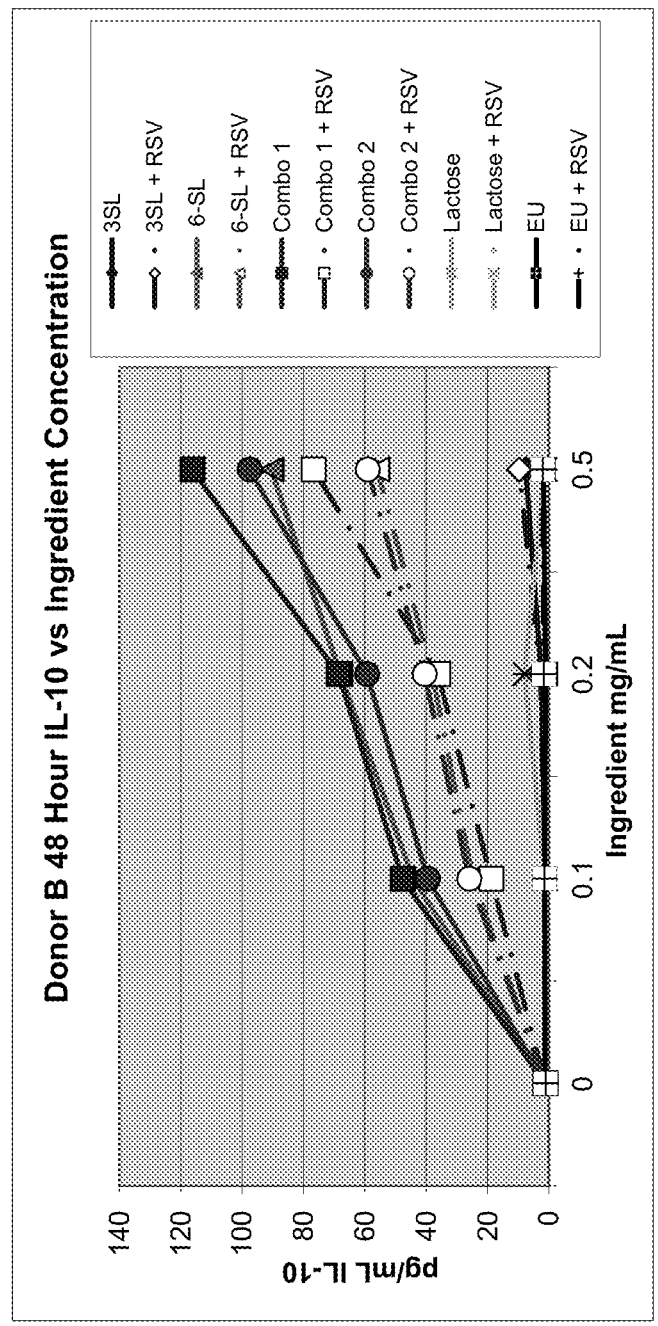
FIGS. 19A and 19B are graphs depicting the IL-10 levels resulting from administration of 6'SL alone or in combination with 3'SL as measured in Example 45.
Figure 19B:
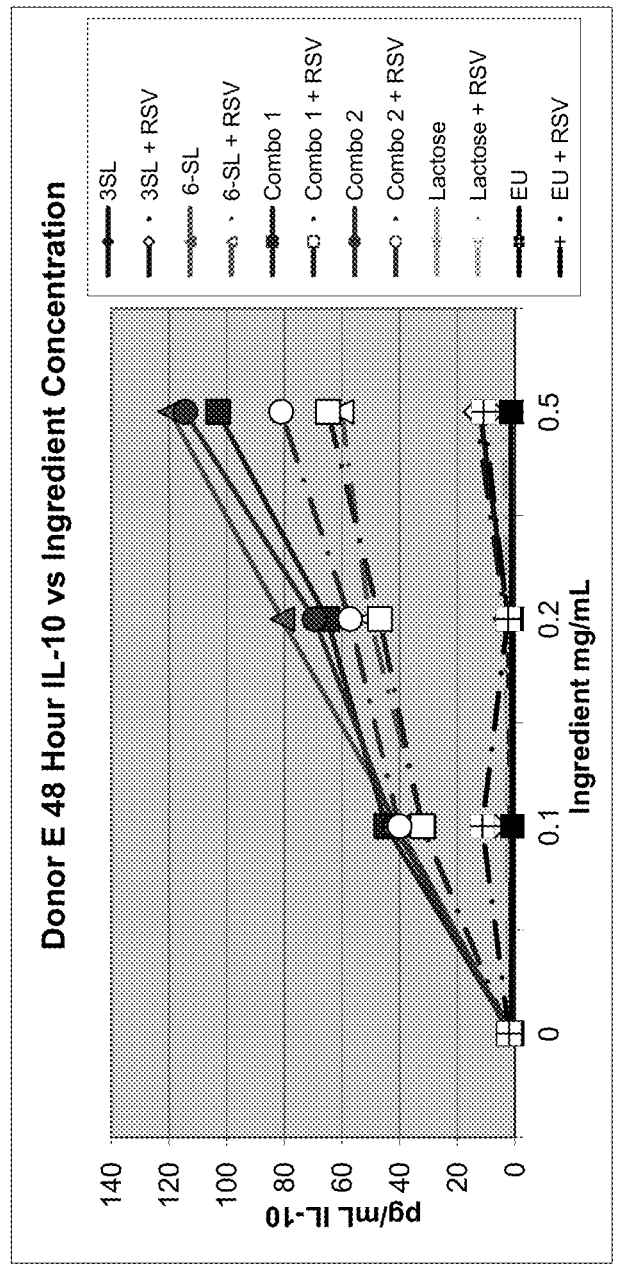

The influence of 3'SL and/or 6'SL on production of Interleukin 10 (IL-10) for PBMCs from Donor B and Donor E are shown in FIG. 19A and FIG. 19B. Surprisingly, increasing concentrations of 6'SL alone or in combination with 3'SL demonstrate a clear dose-dependent increase in IL-10 response in the presence or absence of RSV. 3'SL alone, the lactose control, and the endotoxin control do not increase IL-10.

Figure 20A:
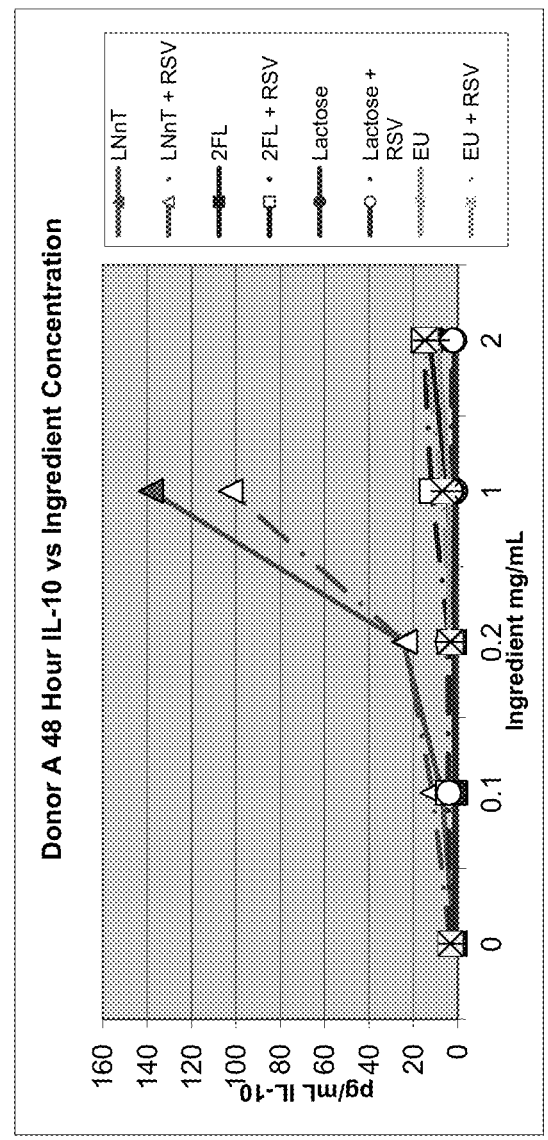
FIGS. 20A and 20B are graphs depicting the IL-10 levels resulting from administration of LNnT or 2'FL as measured in Example 45.
Figure 20B:
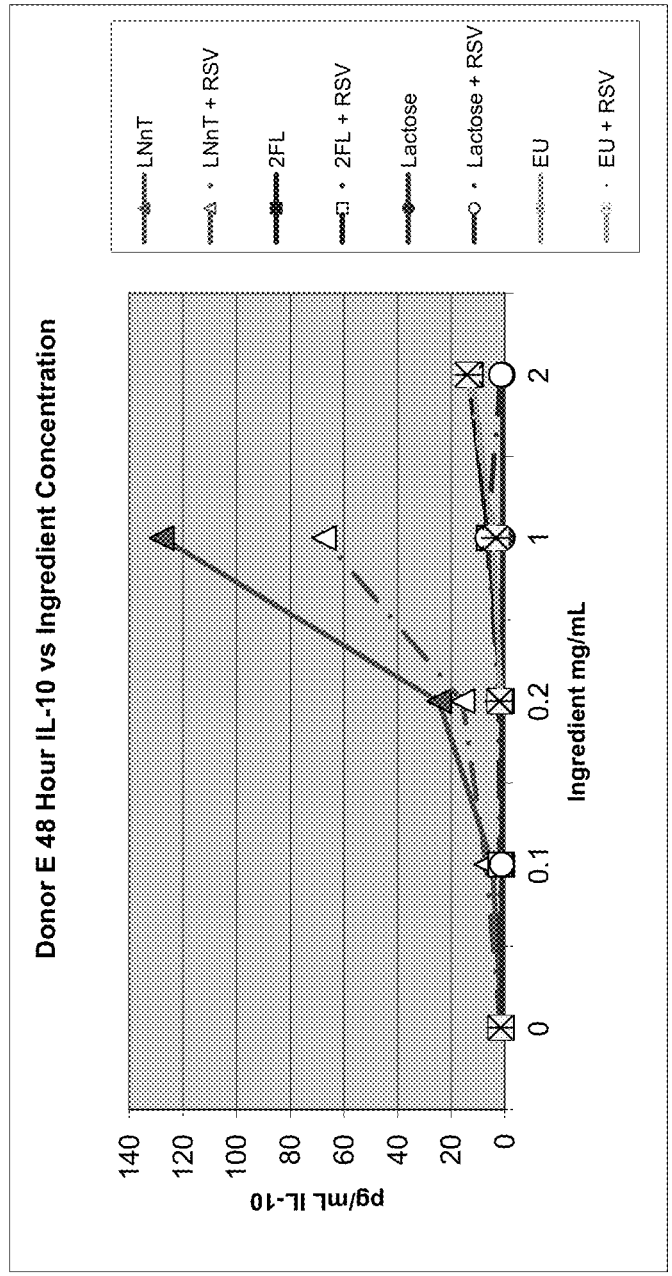

The influence of LNnT or 2'FL on production of IL-10 for PBMCs from Donor A and Donor E are shown in FIGS. 20A and 20B. Surprisingly, increasing concentrations of LNnT show a clear dose-dependent increase in IL-10 response in the presence or absence of RSV. 2'FL alone, the lactose control, and the endotoxin control do not increase IL-10. IL-10 is an anti-inflammatory cytokine that has pleiotropic effects on immunoregulation and inflammation. It suppresses expression of MHC Class II molecules and pro-inflammatory cytokines TNF-alpha, IL-6 and IL-1 as well as enhances B cell survival, proliferation and antibody production. Increasing levels of IL-10 should decrease inflammation and support a healthy adaptive immune system.

Example 46

In this example, the ability of the combination of 2'FL and 6'SL to reduce IP-10, a marker of viral inflammation in vitro is demonstrated.

Specifically, on day 0, fresh human peripheral blood mononuclear cells (PBMCs) are isolated from whole blood. 2'FL (at concentrations of 0.1 mg/mL, 0.2 mg/mL, 0.5 mg/mL or 1 mg/mL) alone or in combination with 6'SL (at concentrations of 0.05 mg/mL, 0.1 mg/mL, 0.2 mg/mL or 1 mg/mL) is added to the PBMCs and incubated for approximately 24 hours at 37° C. in 5% $CO_2$. On day 1, the cell supernatants are removed and the PBMCs are incubated with medium alone or medium plus Respiratory Syncytial Virus (RSV) for approximately 1 hour at 37° C. in 5% $CO_2$ at a multiplicity of infection (MOI) of 1. After approximately 1 hour, fresh medium alone or containing the appropriate concentration of 2'FL and or 6'SL is added to the appropriate tubes, and the cells are incubated for 48 hours at 37° C. in 5% $CO_2$. On day 3, supernatants are collected (48 hours post-infection). Cytokines are measured in supernatants for each variable at 48 hours using Luminex human cytokine kits to assess the effects of HMOs on the early immune response to RSV.

Figure 21:
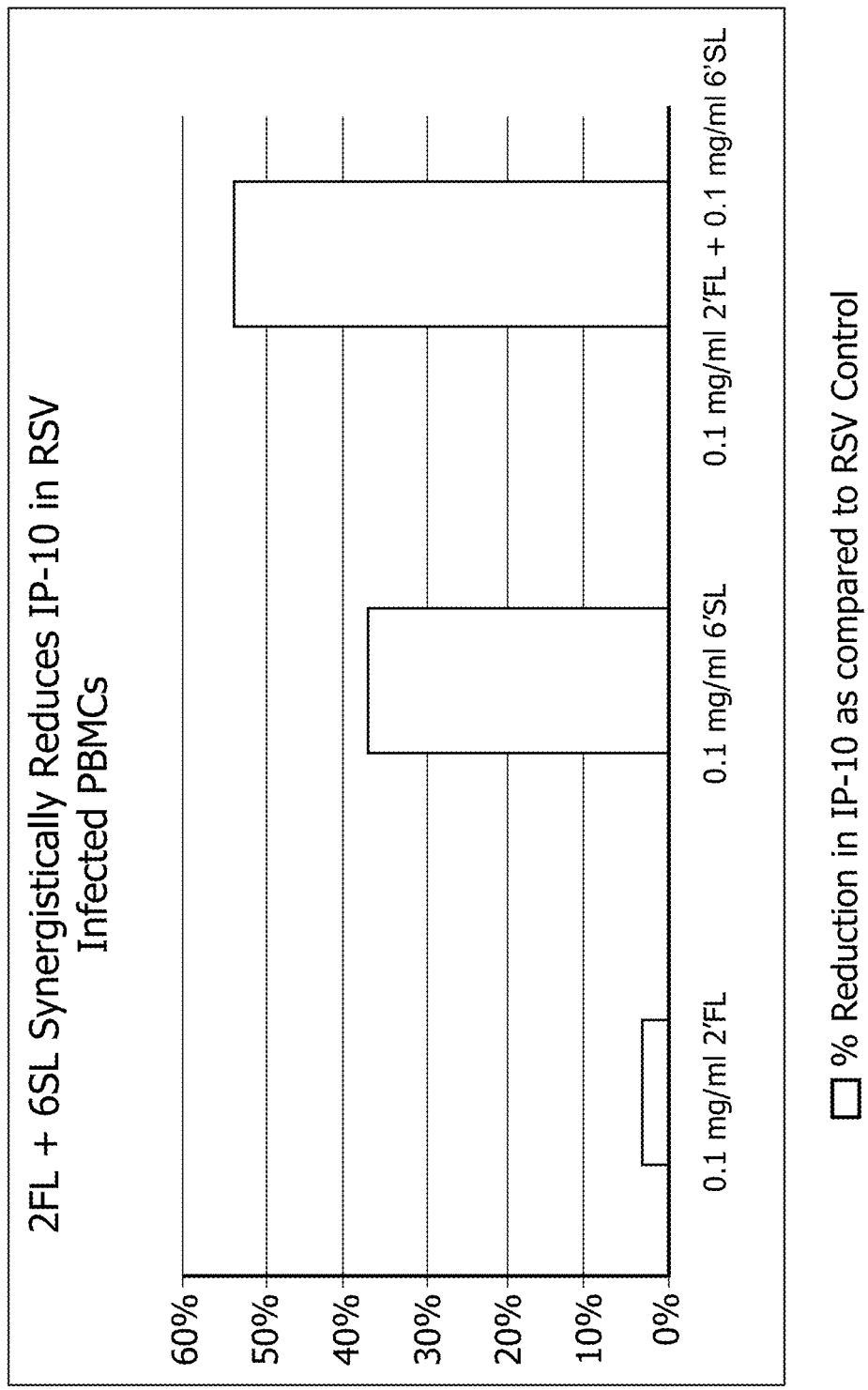
FIG. 21 is a graph depicting the percent reduction in IP-10 resulting from administration of 2'FL and 6'SL alone or in combination as measured in Example 46.
Figure 22:
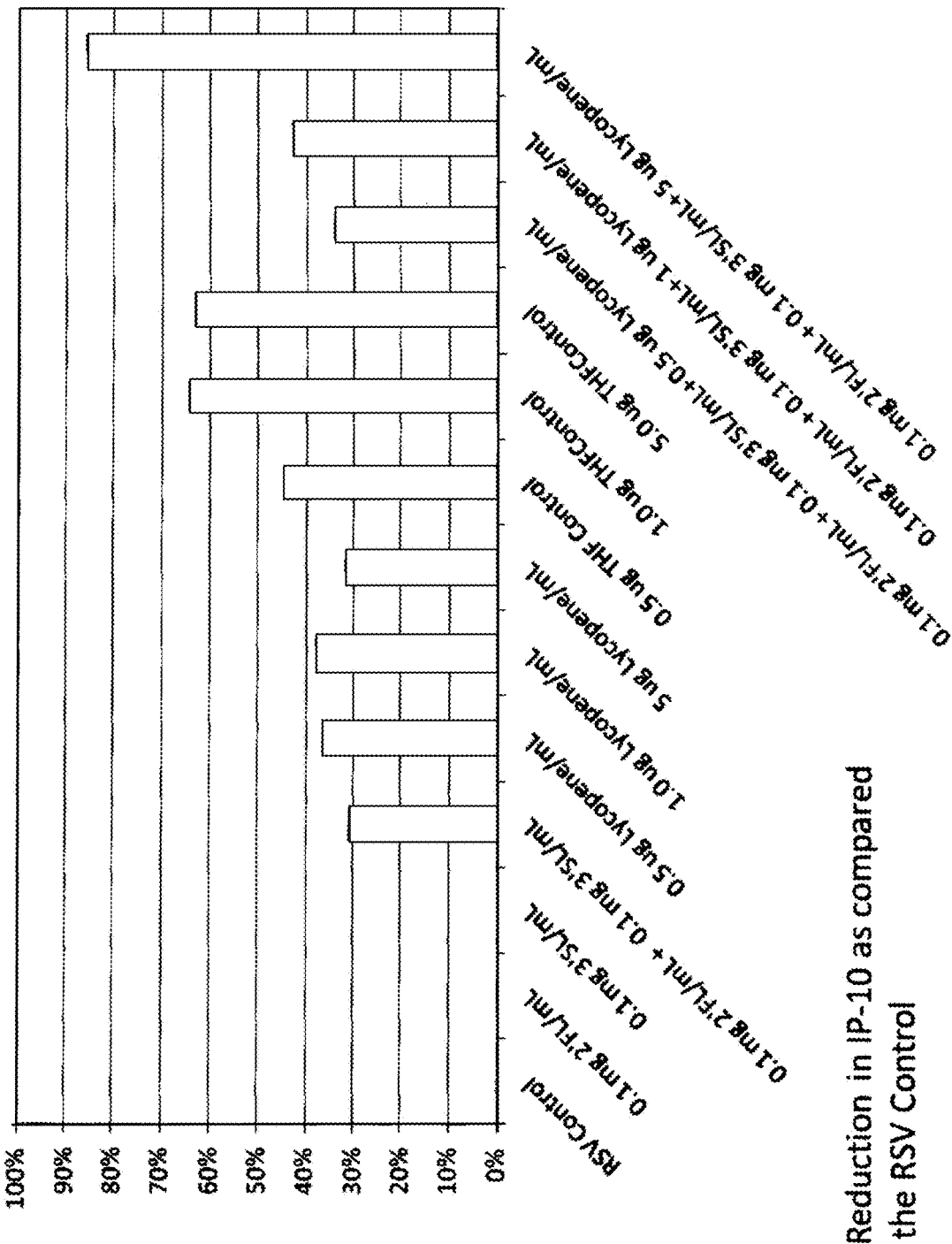
FIG. 22 is a graph depicting the percent reduction in IP-10 resulting from the administration of 2'FL, 3'SL, and lycopene individually or in combination as measured in Example 47.

Surprisingly, as shown in FIG. 21, the combination of 2'FL and 6'SL synergistically reduces production of IP-10 by 54%. Interferon-inducible Protein 10 (IP-10, also known as CXCL10) is a CXC chemokine that attracts, binds to and activates the CXCR3 receptor on Natural Killer Cells and Memory T cells. IP-10 is expressed by monocytes and a number of other cells, and is induced by interferon. A positive correlation exists between RSV clinical disease severity in children (as measured by: length of hospital stay, fever, and number of days supplemental $O_2$ was required) and serum IP-10. Therefore, a decrease in IP-10 may signal a decrease in severity of RSV disease experienced. As such, it can be concluded from the results that by administering the combination of 2'FL and 6'SL, the severity of RSV disease experienced may be reduced.

Example 47

In this example, the ability of the combination of 2'FL, 3'SL, and lycopene to reduce IP-10, a marker of viral inflammation, in vitro is demonstrated.

Specifically, 2'FL (at a concentration of 0.1 mg/mL), 3'SL (at a concentration of 0.1 mg/mL), and lycopene (at concentrations of 0.5 μg/mL, 1.0 μg/mL, or 5 μg/mL) or tetrahydrofuran (THF) (at concentrations of 0.5 μg/mL, 1.0 μg/mL, or 5 μg/mL) alone or in combinations (as shown in FIG. 22) are added to fresh human peripheral blood mononuclear cells (PBMCs) and incubated at 37° C. in 5% $CO_2$ to pretreat the cells for approximately 24 hours. THF is a solvent used to solubilize the lycopene, and as such, a THF concentration control is included to differentiate solvent effects. After approximately 24 hours, some variables are then incubated with RSV at a multiplicity of infection (MOI) of 1 for approximately 1 hour at 37° C. in 5% in $CO_2$. The uninfected control variable is incubated with medium for approximately 1 hour at 37° C. in 5% $CO_2$. After approximately 1 hour, fresh medium alone or containing the appropriate concentrations of 2'FL, 3'SL, and lycopene; 2'FL; 3'SL; 2'FL and 3'SL; lycopene; or THF is added to the appropriate variables, and the PBMCs are incubated for 48 hours at 37° C. in 5% $CO_2$. Supernatants are collected at 48 hours post-infection. Cytokines are measured in supernatants for each variable at 48 hours using Luminex human cytokine kits to assess the effects of HMOs on the early immune response to RSV.

Interferon-inducible Protein 10 (IP-10, also known as CXCL10) is a CXC chemokine that attracts, binds to and activates the CXCR3 receptor on Natural Killer Cells and Memory T cells. IP-10 is expressed by monocytes and a number of other cells, and is induced by interferon. A positive correlation exists between RSV clinical disease severity in children (as measured by: length of hospital stay, fever, and number of days supplemental $O_2$ was required) and serum IP-10. Therefore, a decrease in IP-10 may signal a decrease in severity of RSV disease experienced.

Surprisingly, the combination of 2'FL, 3'SL, and lycopene results in a downregulation of IP-10 that increases with increasing dose of lycopene (See FIG. 22). The synergistic decrease (86% decrease) in IP-10 for 2'FL, 3'SL, and lycopene is seen with the highest lycopene concentration (5.0 μg/mL) tested. As such, it can be concluded that the combination of 2'FL, 3'SL, and lycopene may have a synergistic effect in decreasing the severity of RSV disease experienced.

What is claimed is:

1. A method of dampening inflammation associated with a viral infection in an infected individual, the method comprising administering to the individual a nutritional composition comprising a carotenoid in an amount of 0.1 μg/mL to 10 μg/mL and at least one of the human milk oligosaccharides 2'-fucosyllactose and lacto-N-neotetraose; whereby inflammation in the individual is dampened.

2. A method of dampening inflammation associated with a viral infection in an infected individual, the method comprising administering to the individual a nutritional composition comprising a carotenoid in an amount of 0.1 μg/mL to 10 μg/mL and lacto-N-neotetraose, wherein the nutritional composition is free of other human milk oligosaccharides.

3. The method of claim 1, wherein the individual is infected with a respiratory virus.

4. The method of claim 3, wherein the respiratory virus is a virus selected from the group consisting of respiratory syncytial virus, human parainfluenza virus, and influenza A virus.

5. The method of claim 1, wherein dampening inflammation associated with a viral infection decreases the severity of the viral infection.

6. The method of claim 1, wherein dampening inflammation associated with a viral infection comprises increasing the speed of recovery from the viral infection.

7. The method of claim 1, comprising administering a nutritional composition having an amount of the human milk oligosaccharide effective to dampen an immune system response which contributes to increased severity of a viral infection.

8. The method of claim 1, wherein the nutritional composition comprises at least about 0.2 mg/ml of lacto-N-neotetraose, at least about 0.1 mg/ml of 2'-fucosyllactose, or both.

9. The method of claim 8, wherein the nutritional composition comprises at least about 0.1 mg/ml of 2'-fucosyllactose.

10. The method of claim 1, wherein the nutritional composition further comprises an acidic human milk oligosaccharide.

11. The method of claim 8, wherein the nutritional composition comprises at least about 0.2 mg/ml of lacto-N-neotetraose.

12. The method of claim 8, wherein the nutritional composition comprises at least about 1 mg/mL of lacto-N-neotetraose, at least about 2 mg/mL of 2'-fucosyllactose, or both.

13. The method of claim 1, wherein the individual is susceptible to infection-mediated inflammatory disease.

14. The method of claim 1, wherein the individual has an immature immune system.

15. The method of claim 1, wherein the individual is an infant, toddler, or child.

* * * * *